United States Patent
Kilinc et al.

(10) Patent No.: US 11,273,454 B2
(45) Date of Patent: Mar. 15, 2022

(54) OPTICAL DETECTION BASED ON NON-LINEAR MAGNETOPHORETIC TRANSPORT OF MAGNETIC PARTICLE FOR PARTICLE AND BIOLOGICAL SENSING AND SEPARATION

(71) Applicant: University College Dublin, National University of Ireland, Dublin, Dublin (IE)

(72) Inventors: Devrim Kilinc, Dublin (IE); Peng Li, Dublin (IE); Gil Lee, Dublin (IE); Dhruv Ghandi, Dublin (IE); Stefano Rampini, Dublin (IE)

(73) Assignee: University College Dublin, National University of Ireland, Dublin, Dublin (IE)

( * ) Notice: Subject to any disclaimer, the term of this patent is extended or adjusted under 35 U.S.C. 154(b) by 455 days.

(21) Appl. No.: 15/741,472

(22) PCT Filed: Jul. 4, 2016

(86) PCT No.: PCT/EP2016/065731
§ 371 (c)(1),
(2) Date: Jan. 2, 2018

(87) PCT Pub. No.: WO2017/001705
PCT Pub. Date: Jan. 5, 2017

(65) Prior Publication Data
US 2018/0361396 A1  Dec. 20, 2018

(30) Foreign Application Priority Data
Jul. 2, 2015  (GB) ..................................... 1511615

(51) Int. Cl.
| | |
|---|---|
| *G01R 33/3873* | (2006.01) |
| *B03C 1/24* | (2006.01) |
| *B03C 1/28* | (2006.01) |
| *G01N 27/74* | (2006.01) |
| *G01N 33/543* | (2006.01) |

(52) U.S. Cl.
CPC ............. *B03C 1/24* (2013.01); *B03C 1/288* (2013.01); *G01N 27/745* (2013.01); *G01N 33/54333* (2013.01); *B03C 2201/26* (2013.01)

(58) Field of Classification Search
None
See application file for complete search history.

(56) References Cited

U.S. PATENT DOCUMENTS

| | | | |
|---|---|---|---|
| 9,421,555 B2 * | 8/2016 | Lee ................. | G01N 27/44756 |
| 2002/0135772 A1 * | 9/2002 | Bornhop ............... | G01N 21/41 356/450 |
| 2008/0124779 A1 | 5/2008 | Oh et al. | |
| 2010/0279887 A1 * | 11/2010 | Lee ...................... | G01N 27/745 506/9 |
| 2012/0135494 A1 * | 5/2012 | Murthy ................. | C12M 47/10 435/173.9 |
| 2012/0187938 A1 * | 7/2012 | Bar .................... | B01L 3/502761 324/204 |
| 2012/0322683 A1 | 12/2012 | Liu et al. | |
| 2014/0045701 A1 * | 2/2014 | Esfandyarpour .... | C12Q 1/6874 506/2 |
| 2014/0227679 A1 | 8/2014 | Lee et al. | |
| 2015/0125873 A1 * | 5/2015 | Newman .............. | G01N 27/745 435/7.1 |
| 2016/0209406 A1 * | 7/2016 | Aojula .................... | B01L 3/502 |

FOREIGN PATENT DOCUMENTS

| | | | |
|---|---|---|---|
| WO | 02/093125 A2 | 11/2002 | |
| WO | WO2008156688 | * 12/2008 | ......... G01R 33/3873 |
| WO | 2010/076337 A1 | 7/2010 | |
| WO | 2012004363 A2 | 1/2012 | |

OTHER PUBLICATIONS

International Search Report and Written Opinion for corresponding application PCT/EP2016/065731, European Patent Office, dated Oct. 14, 2016.
Combined Search and Examination Report for corresponding application GB1511615.5 Intellectual Property Office (UK), dated Dec. 22, 2015.

* cited by examiner

*Primary Examiner* — Ann Y Lam
(74) *Attorney, Agent, or Firm* — Holzer Patel Drennan

(57) ABSTRACT

There is provided system and a separation substrate device for use with an NLM separator in separating and/or detecting at least one target analyte in a sample, the substrate comprising a micromagnet array of a plurality of micromagnets, the micromagnet array comprising a first capture region, a second focusing region, and, a third detection region, the focusing region comprising a converging and/or diverging micromagnet array region. Also provided is a method for separating and detecting at least one target analyte in a sample. The method including: contacting a plurality of magnetic beads with a sample, the magnetic beads functionalized for binding with one or more target analytes in a sample to form aggregates; providing the sample including magnetic beads and aggregates to a separating substrate comprising a micromagnet array of a plurality of micromagnets; transporting the magnetic beads and aggregates relative to the micromagnet array to provide separation and enable detection of the magnetic beads and aggregates; detecting motion of the beads or aggregates of the sample on the array in response to the applied magnetic field and/or detecting beads or aggregates of the sample on the array at a detection region of the array.

20 Claims, 34 Drawing Sheets

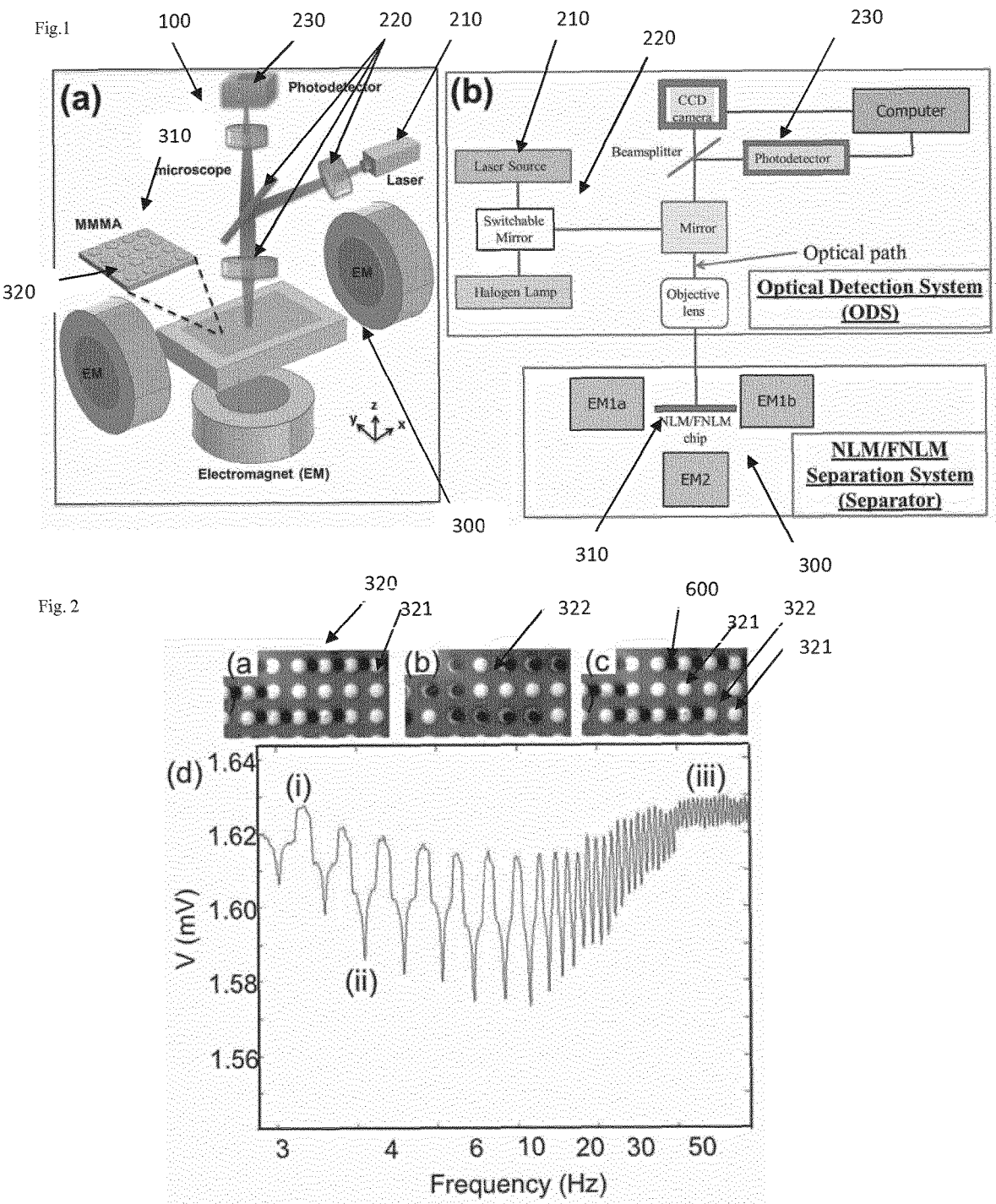

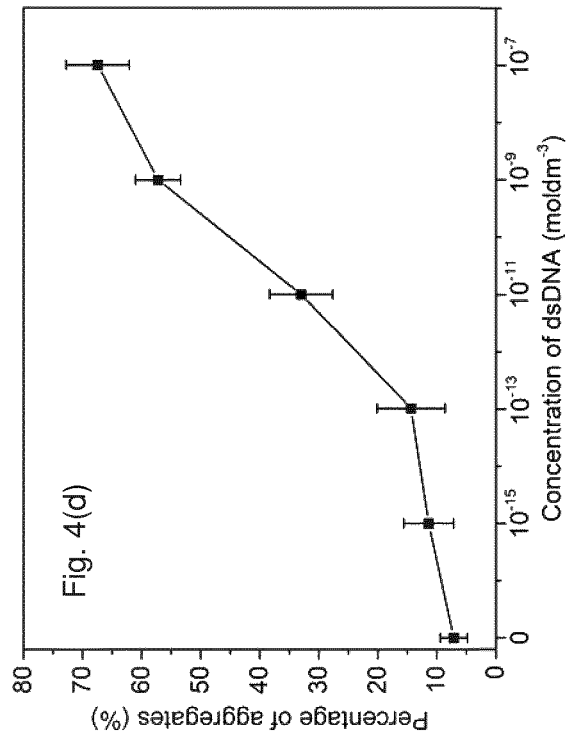
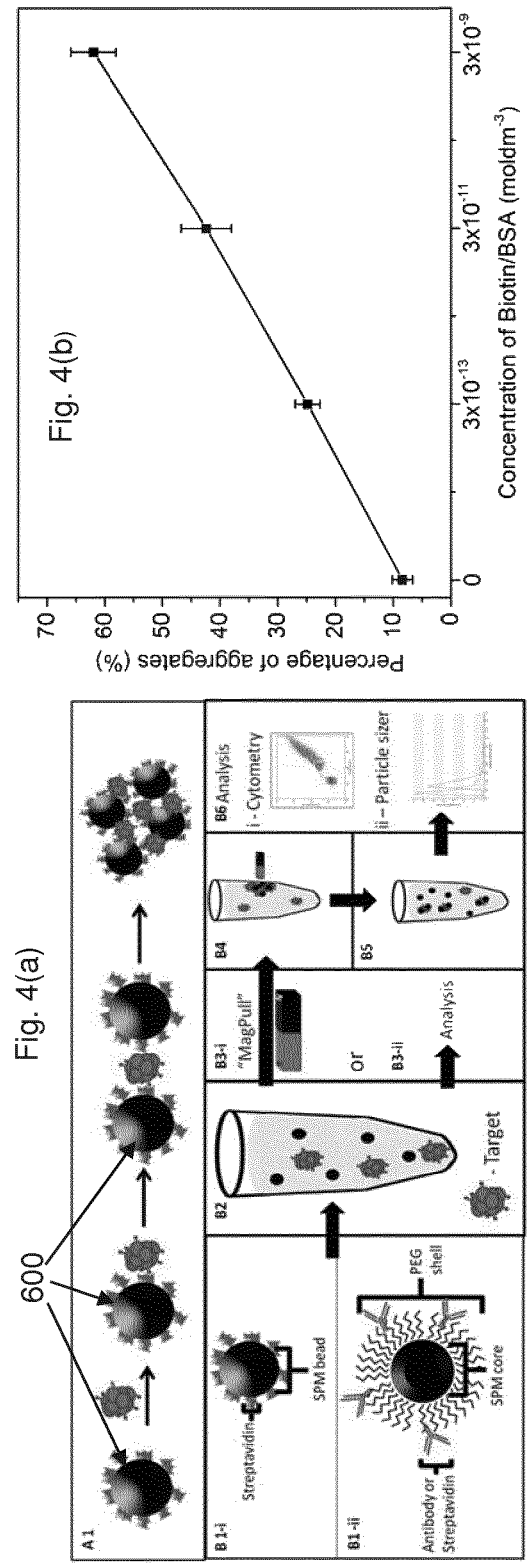
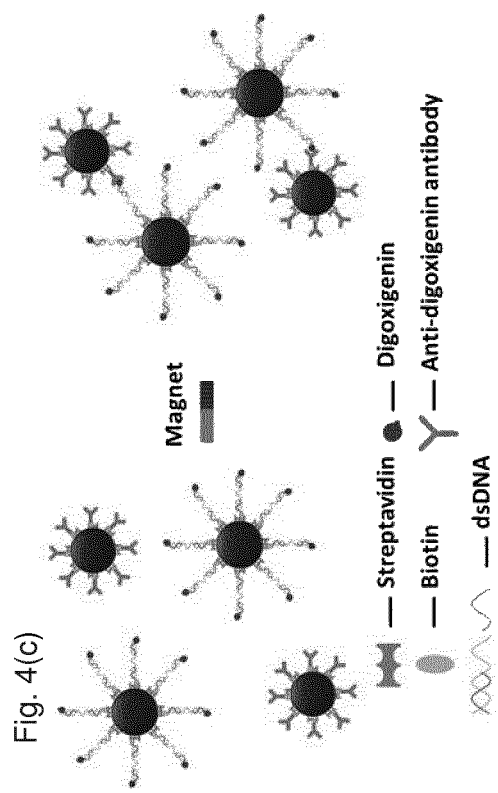

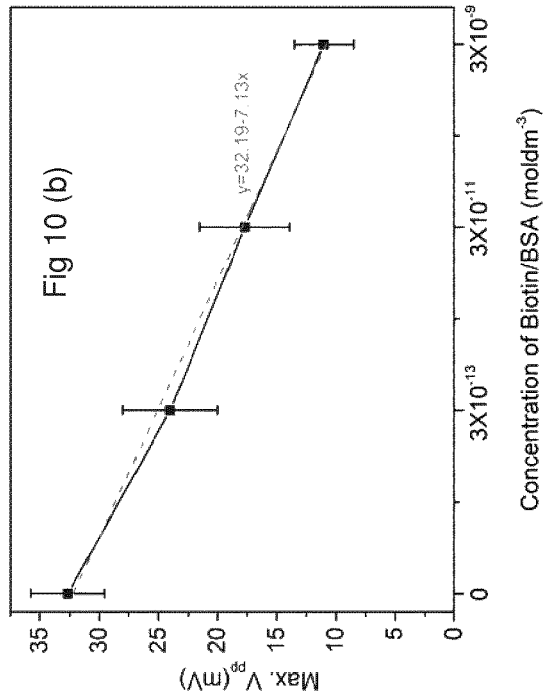
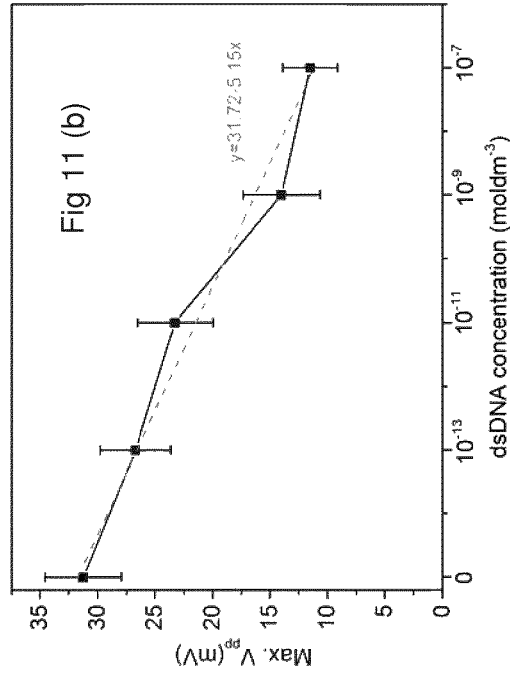
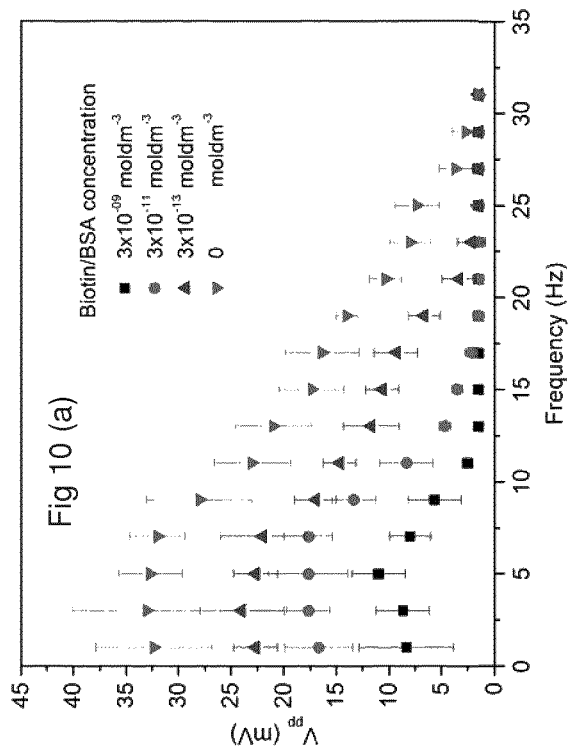
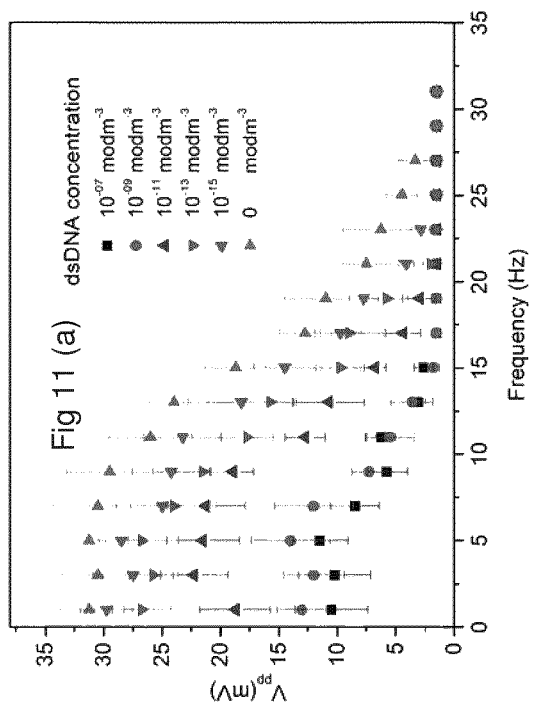

520

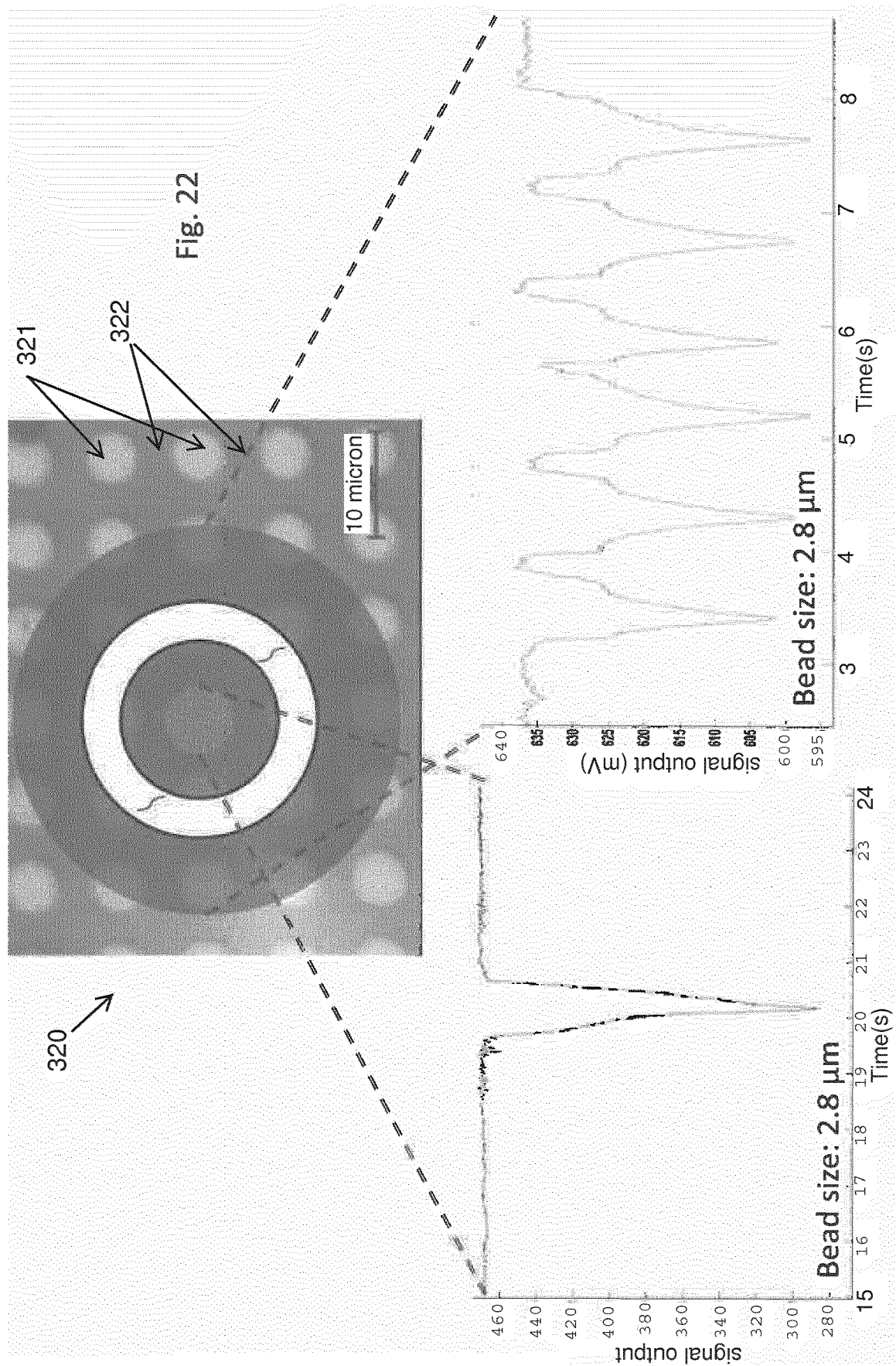

✓ Different signal for different size of the beads
✓ Different signal for monomers and dimers of the same sized beads

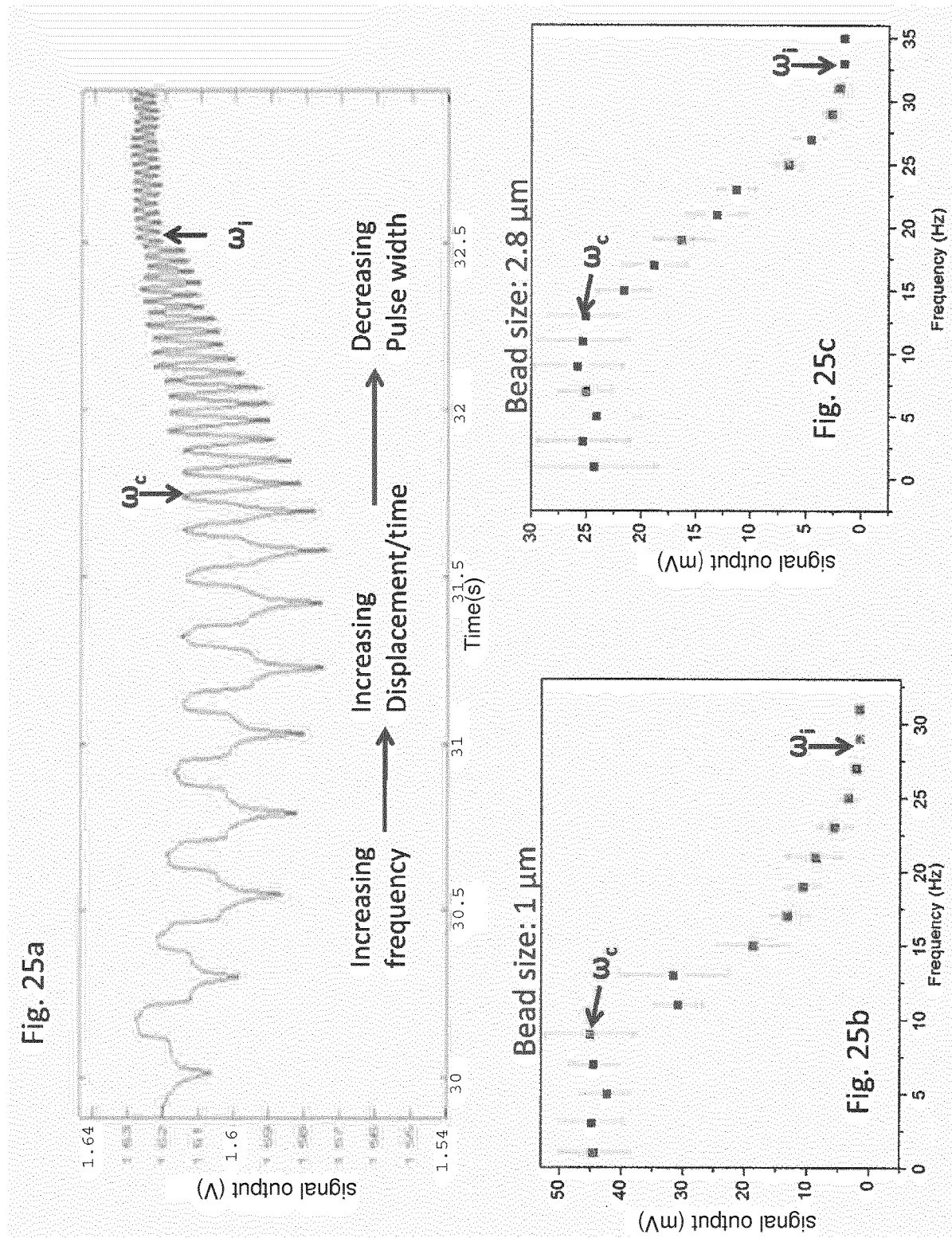

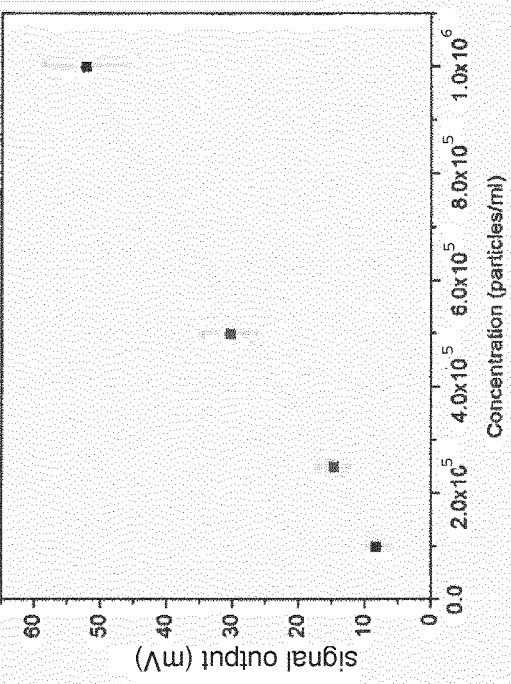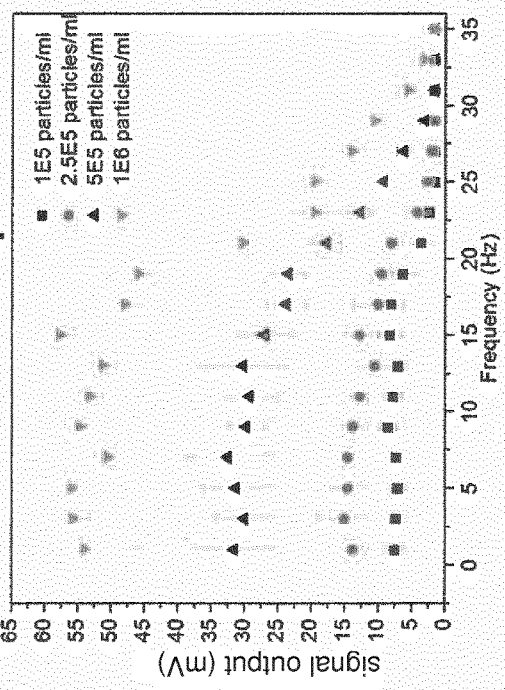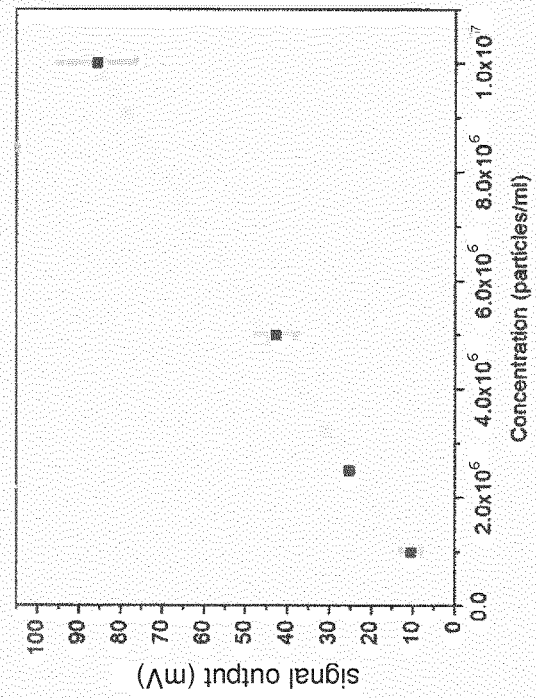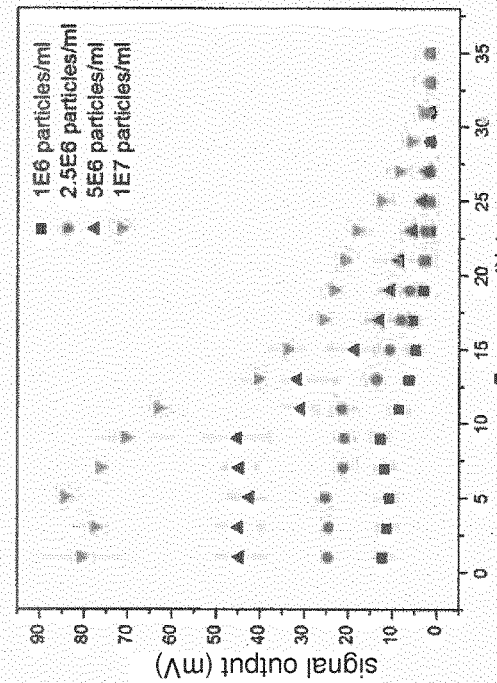

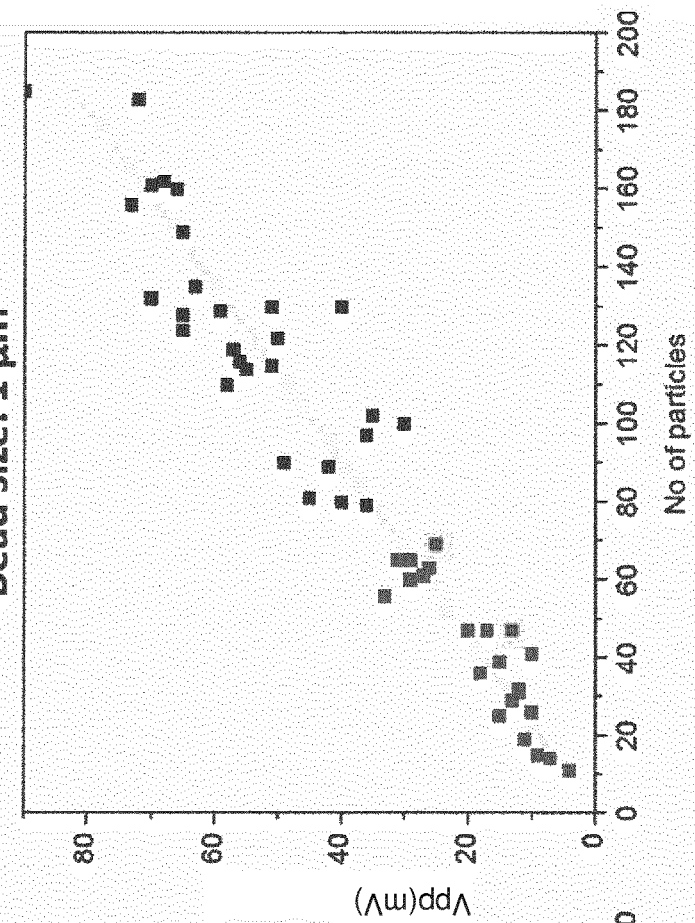
Fig. 28b — Bead size: 1 μm
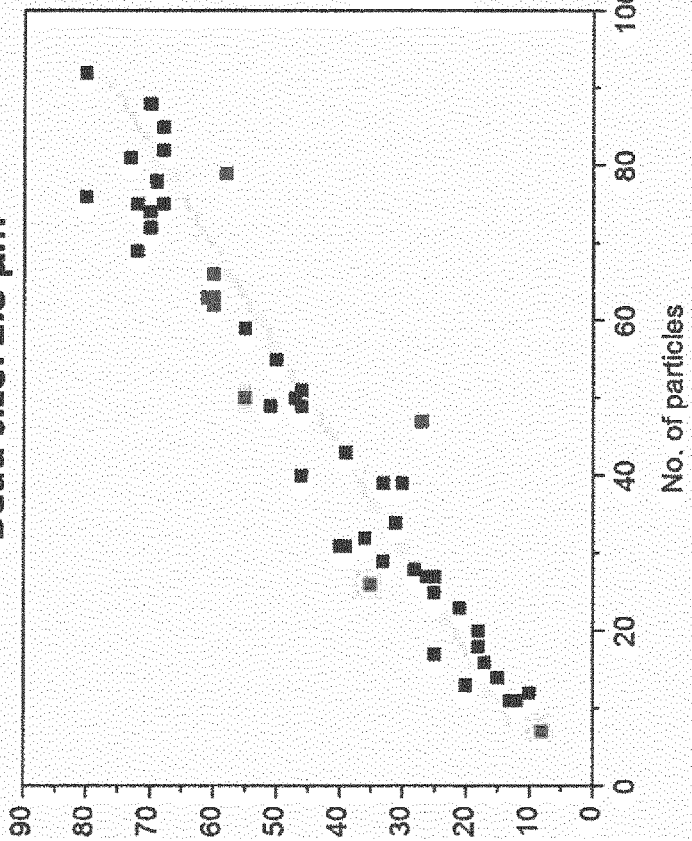
Fig. 28a — Bead size: 2.8 μm
✓ Clear Linear relationship for the optical signal vs number of particles passing through the laser spot
✓ Calibration curves can be used for optical signal data evaluation

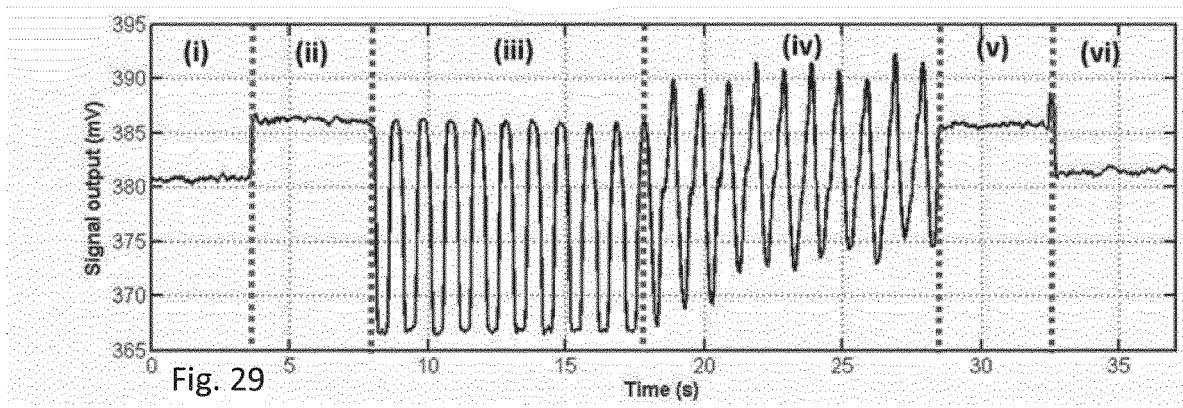
Fig. 29
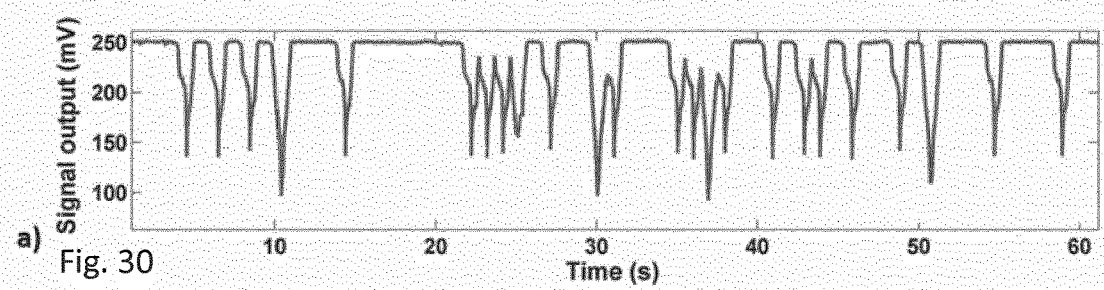
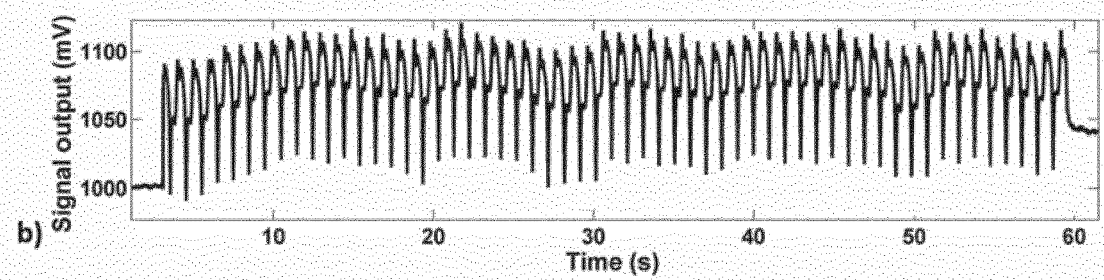
Fig. 30
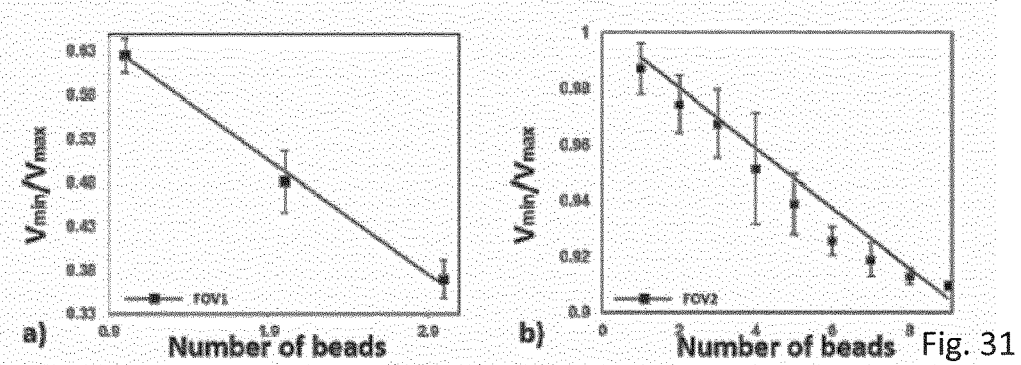
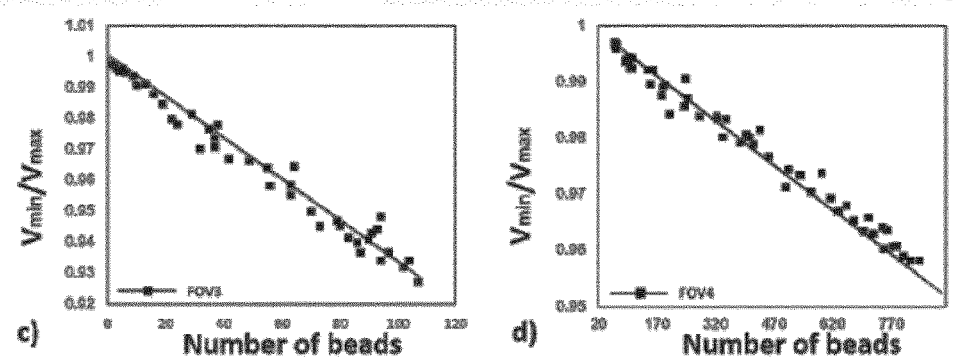
Fig. 31

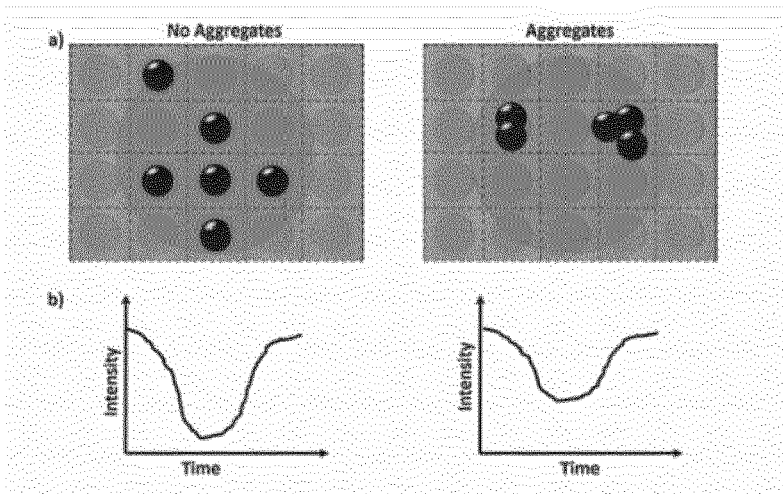
Fig. 39
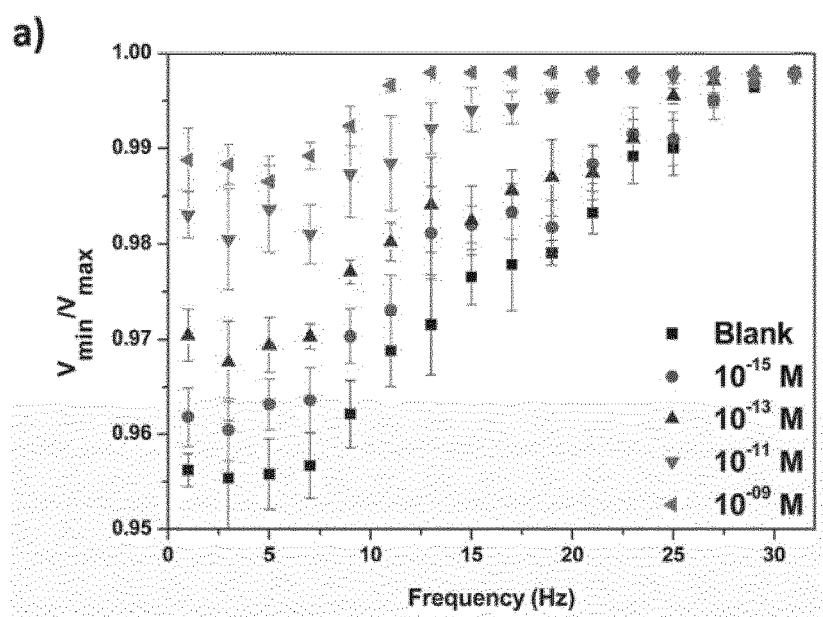
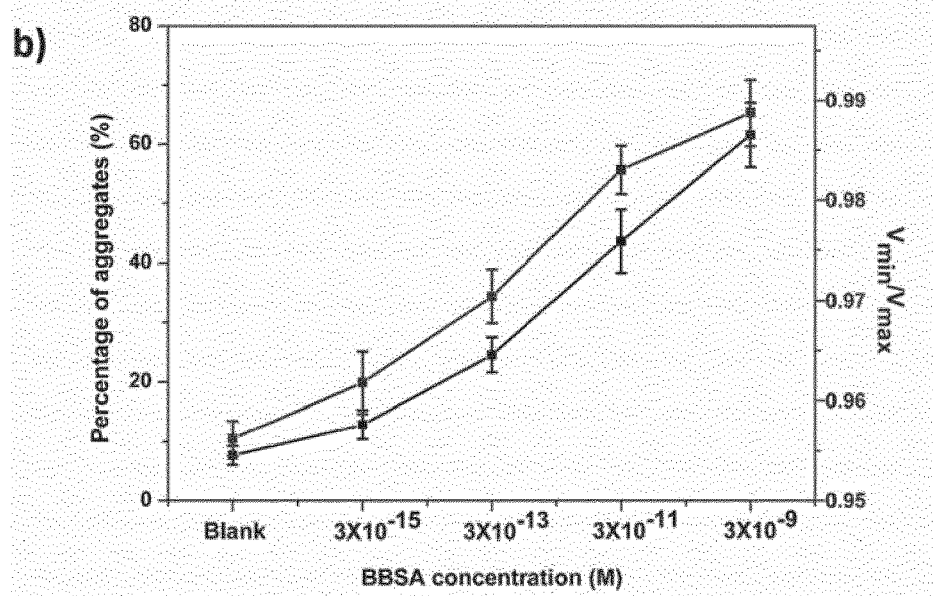
Fig. 40

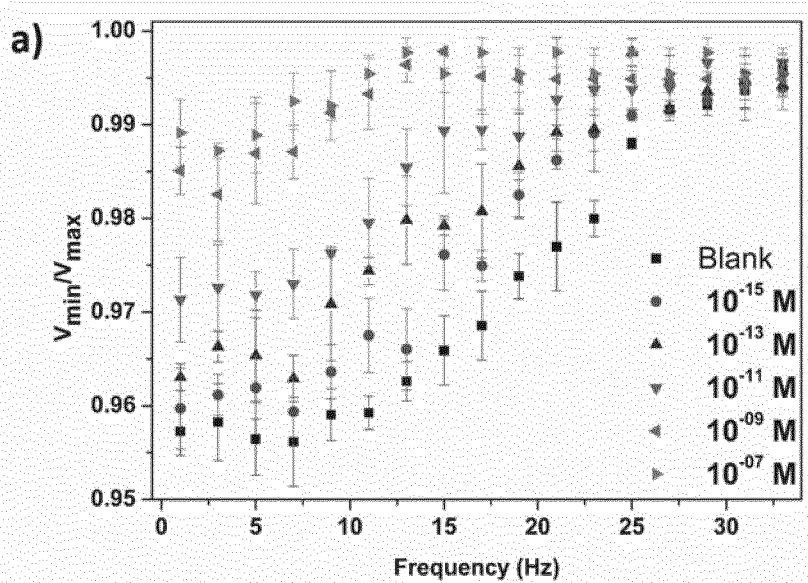
Fig. 41
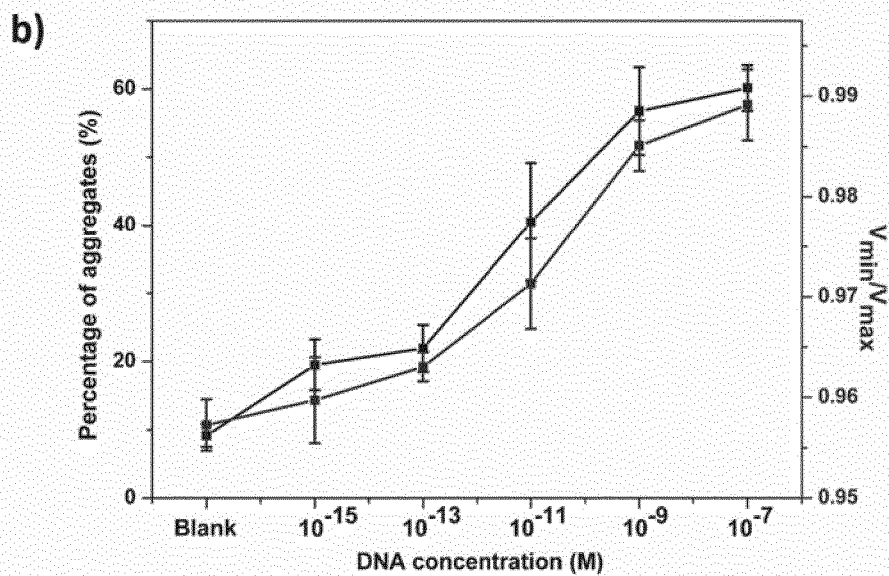
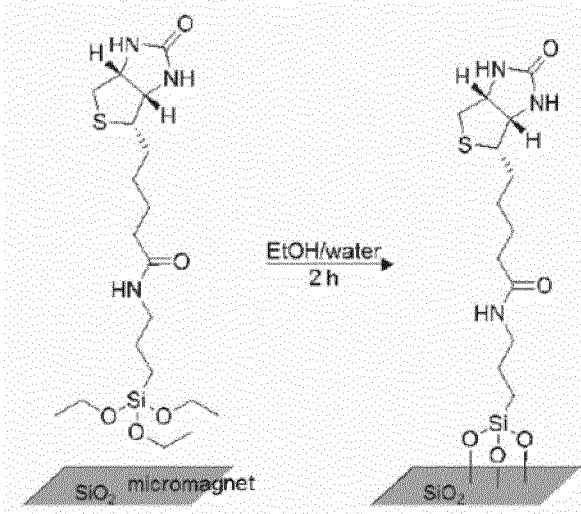
Fig. 42

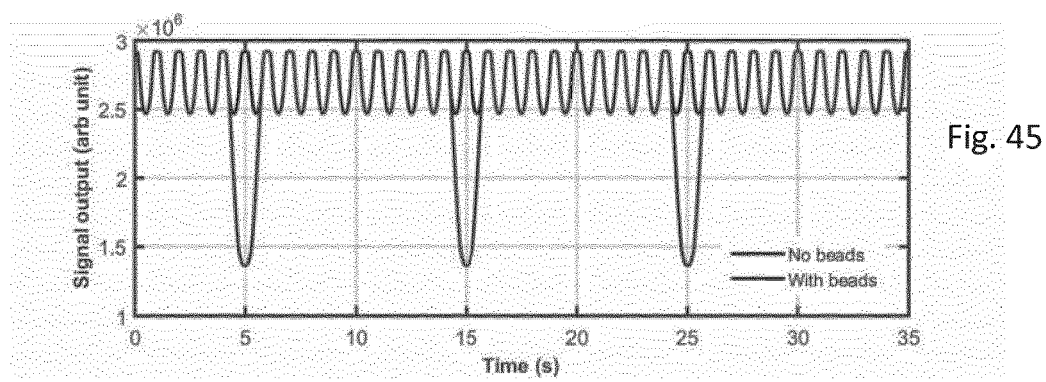
Fig. 45
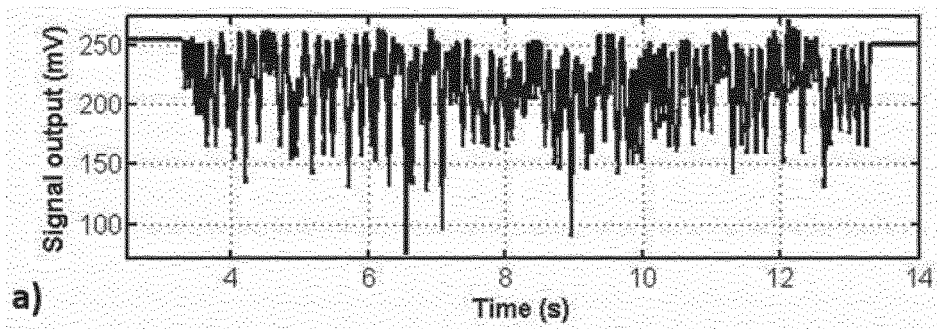
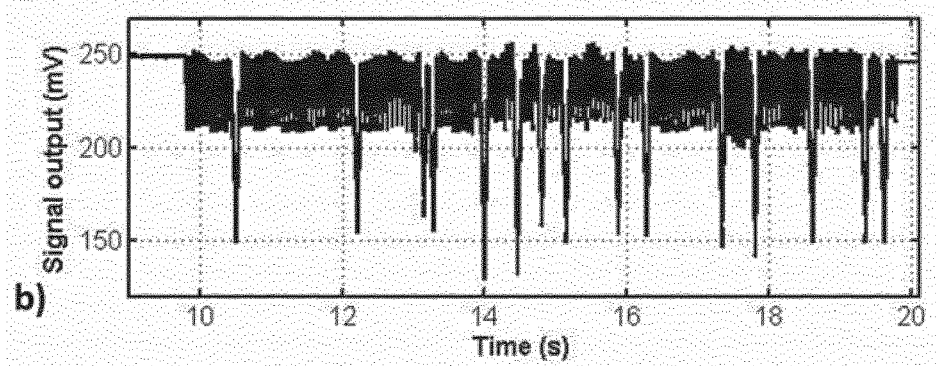
Fig. 46
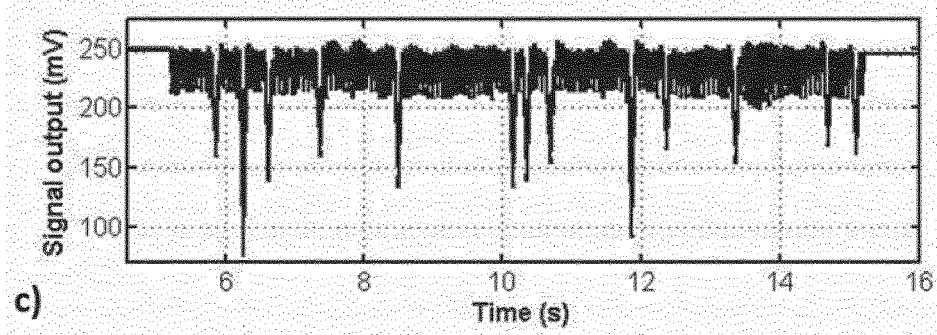
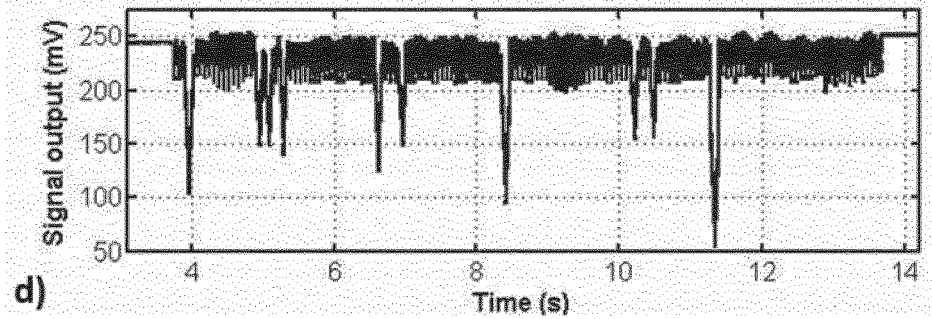

OPTICAL DETECTION BASED ON NON-LINEAR MAGNETOPHORETIC TRANSPORT OF MAGNETIC PARTICLE FOR PARTICLE AND BIOLOGICAL SENSING AND SEPARATION

The present specification relates generally to methods and materials for biological sensing and separation. More specifically, it relates to an integrated optical detection and sensing system combined with a non-linear magnetophoretic separation system, and separation of superparamagnetic (SPM) micro-particles and attached biological materials in complex environments.

BACKGROUND

There are increasing demands for portable, economical, and user friendly diagnostic instruments, which can perform fast and precise sensing of biological analytes and also can be mass fabricated in production.

Based on microelectromechanical system (MEMS) technology and micro-fluidics, the lab-on-a-chip (LOC) system has been developed and provided a strategy for such demands. As a result, various micro-sensors and micro-actuators have been developed.

Optical micro-particle detector has been used in airborne and microfluidic micron or nano-sized particles detection due to advantages, such as speed, sensitivity, and it provides a non-contact, bio-compatible approach. Among this field, flow cytometry has been used to detect the particles and biological analytes, such as cells, DNA, bacteria, e.g. in laboratory applications. However, there are still challenges with such systems including limited resolution, difficulties for particles focusing, and limited detection volume of particles.

The present application aims to address such problems and to find provide an improved detection system including to provide an improved lab-on-a-chip detection system The present application further aims to address the problems of limited detection volume, limited resolution and problems associated with particle focusing.

Bio-separation describes techniques used for determining the molecular state of a cell, or whole organism. Currently, bio-separation is often performed using liquid chromatography, electrophoresis or centrifugation, which achieves separation by transporting an analyte relative to a stationary phase based on a physical or chemical property, such as surface chemistry, size, charge, or mass density. Although these techniques separate analytes with a relatively high resolution they are recognized to have the problems of being slow and often difficult to implement. Another bio-separation technique is magnetophoresis. In this technique a very strong magnetic field and field gradient are typically applied to effect separation. However, in known linear magnetophoresis, the magnetic particles often coagulate to form undetectable complexes such as chains, which can make it difficult to perform multiple separations on different particles.

There is therefore a need to address these and other problems and limitations of prior art separation devices and methods. There is a need to provide an improved separation and detection system and method.

BRIEF DESCRIPTION OF THE DRAWINGS

FIG. 1(a) shows an illustration of a NLM/FNLM separator with an optical detector ONLM above it for SPM particles detection of an exemplary arrangement according to the present specification. The detector is integrated with NLM/FNLM separator to perform particles/biological analytes sensing and separation simultaneously.

FIG. 1(b) shows schematics of configuration and diagram of detection system for NLM/FNLM system. In the exemplary arrangement, the NLM/FNLM separator is a micro fabricated chip with transparent window, through which the light can illuminate the chip surface and the light can also be reflected to the detector, as shown in FIG. 1(b). A programmable rotating magnetic field created by two sets of electromagnets (EM1 and EM2) surrounds the chip for separation control. The separator is operable to manipulate and separate the introduced sample particles. As shown in FIG. 1(b), detector is aligned above with the transparent window of NLM/FNLM chip for optical detection and sensing of sample particles, which are controlled by separator. The core components of the detection system include an objective, reflective and switchable mirrors/prisms, an adjustable portable laser source, a photodetector, and data acquisition and processing computer and software. Additionally, to visualize the separation process, a CCD camera, halogen light, switchable mirror, and an optical beamsplitter are also used as optional components. FIG. 1(b) illustrates the transport of magnetic particles in NLM/FNLM chip while the ONLM is sensing the magnetic particles and their biological attachments.

FIGS. 2(a)-2(c) show NLM transport of SPM particles on micro-magnets array (MMA) at different phases of an exemplary arrangement according to an arrangement of the specification. FIGS. 2(a) and 2(b) show the SPM particles transport at relatively low rotation frequency of rotating magnetic field. At this stage, the particles move stably and their moving speed is proportionally to the rotation frequency. FIG. 2(c) shows the SPM are immobilized on the MMA at high rotation frequency of rotating magnetic field. The circular micro-magnets are coated with Chromium, which are very good reflectors compared with silicon substrate beneath them. The SPM particles are optically black. When the laser incidence to the MMA from the ONLM is above it, the reflective light is modulated by the movement of SPM particles as they periodically travel along the MMA.

FIG. 2(d) shows the signal output of photodetector in ONLM to the reflective light as the SPM particles traveling on MMA at different rotation frequencies of rotating magnetic field. As shown in FIG. 2(a), when SPM particles move to the locations between adjacent micro-magnets and leave all metal micro-magnets as clear reflectors to the laser, the total intensity of reflective light from micro-magnets comprising for example Chromium is the strongest, which correspond to the peak points, such as point "(i)" in FIG. 2(d). When the SPM particles travel to the locations directly on metal micro-magnets and block the metal reflectors, the signal outputs of photodetector in ONLM becomes to the weakest, as shown in valley points, such as point "(ii)" in FIG. 2(d), correspondingly. As a result, when the SPM particles stably move across the periodic MMA surface, the ONLM output will periodically change and the stable $V_{pp}$ signal of ONLM outputs can be maintained. But at very high rotation frequency, due to the partially or all SPM particles are immobilized on MMA, as shown in FIG. 2(c), the $V_{pp}$ signal of ONLM outputs start to decrease until they reach to minimums, as shown in point "(iii)" in FIG. 2(d). Therefore, by analyzing the ONLM outputs, including their shapes, frequency, intensity, etc. obtained by optical properties of particles can be known.

FIG. 3b) In the configuration shown, operative during separation particles travel from left to right by following the micro-magnets lines and are focused at the front-end of the focusing MMA; FIG. 3c) Multiple focusing micro-magnets lines composed a focusing MMA to allow large number of particles focusing on-chip; FIG. 3d) The focusing MMA with a tree-like hierarchical structure is composed of multiple focusing MMAs for multi-step focusing.

FIG. 4(a) shows the concept and process to use target biological species to form micro-particles aggregates and the form process. FIG. 4(b) shows fraction of aggregates Biotin/BDA linked SPM particles in presence of different concentration of Biotin/BSA measured by using flow cytometry. It is shown that the aggregate proportion increases as the Biotin/BSA concentration increase from 0 to $10^{-9}$ moldm$^{-3}$. Based on this curve, the ratio between aggregates and mono-dispersed particles can be obtained for known concentration of SPM particles and Biotin/BSA. FIG. 4(c) shows the formation of sandwich structures (aggregates) in presence of dsDNA and antibodies on functionalized magnetic particles. By using "magpull" process, the functionalized particles can form certain amount of sandwich structures for ONLM detection on NLM/FNLM chip. FIG. 4 (d) shows the fraction of aggregates formed by dsDNA coated particles. It also shows that the increased concentration of dsDNA increase the percentage of aggregates in the suspension as expected.

FIG. 5(a). Sensing of one type of bio-materials on SPM particles by detect the signal difference of ONLM between functionalized areas (areas F) and non-functionalized areas (areas N). The mobility of functionalized particles on areas F and areas N are different. By scanning the areas and comparing the signal differences, detection of presence of bio-materials can be achieved. For instance, in FIG. 5(a), the dispensed particles on areas N move in y and induce ONLM signal while the particles on areas F are specifically stuck by bio-materials, in the case of presence of bio-materials affinity on the particles, and produce relative low ONLM signal due to low immobility of particles. FIG. 5(b) shows a concept for detection of multiplex bio-materials on SPM particles by using multiple functionalized particles and patterned affinity bio-materials coatings on surface of MMA. For instance, three different types of bio-materials coatings patterned on the MMA surface and three different types of SPM particles, which are coated with affinity bio-materials correspondingly, can specifically bond to corresponding bio-materials, are used for detection. In external rotating magnetic field, the particles move to x direction. In presence of specific bonding between corresponding particles and patterned coatings, the particles can be immobilized on patterned coatings. By scanning the whole MMA surface and comparing the signal different in specific moment and locations, the bio-materials on the particles can be detected.

FIG. 10(a) shows measured $V_{pp}$ signal output of ONLM for the samples with different concentrations of BBSA vs. rotation frequency of external rotating magnetic field on NLM/FNLM chip. FIG. 10(b) shows the maximum output signal of ONLM vs. concentration of Biotin/BSA. It shows the significant signal difference between different concentrations of Biotin/BSA. It suggested that the ONLM is capable of sensing of biological species with high sensitivity;

FIG. 11(a) shows measured Vpp signal output of ONLM for the samples with different concentrations of dsDNA vs. rotation frequency of external rotating magnetic field on NLM/FNLM chip. FIG. 11(b) shows the maximum output signal of ONLM vs. concentration of dsDNA. It shows the significant signal difference between different concentrations of dsDNA. It suggested that the ONLM is capable of sensing of dsDNA with high sensitivity;

FIG. 12d shows particles focused in the central region of the array;

(FIG. 14a) Design A consists of a continuous array of 5 μm circular micromagnets (region 1), followed by parallel lines of magnets tilted by ±7° with respect to the horizontal axis of the chip (region 2). (FIGS. 14b-d) Microscope images of the focusing process in design A (images correspond to the boxed areas in (FIG. 14a)). The inset in (FIG. 14d) shows the diamond junction between the tilted lines and the central row of magnets (magnified 4×). (FIG. 14e) Simulation of the potential energy at a diamond junction for different angles of the applied field, and the corresponding expected positions of a travelling magnetic bead (black circles). The arrow indicates the predicted direction of bead motion. (FIG. 14f) Simulation of the potential energy along the central row of magnets (boxed area in (FIG. 14d) along the green dashed line). The simulations were performed by imposing a micromagnet magnetisation of 80 kA/m and an external field with a flux density of 30 G. (FIG. 14g) Design B consists of a continuous array of 5 μm circular micromagnets, followed by a tree-like structure. (FIGS. 14h-i) Focusing process on design B with the beads (arrows) leaving region 1 (FIG. 14h), travelling along the tilted lines of magnets (FIG. 14i), and crossing a focusing junction (FIG. 14j). The inset in (FIG. 14j) shows a tri-magnet focusing junction (magnified 1.5×). (FIG. 14k) Simulation of the potential energy at a tri magnet junction for different angles of the applied field, and the corresponding expected positions of a travelling magnetic bead (black circles). The arrow indicates the anticipated direction of bead motion. (FIG. 14l) Simulation of the potential energy across a focusing junction (boxed area in (FIG. 14j) along the green dashed line). The magnitude of the potential energy minimum increased towards the tri-magnet junction and remained constant as it followed the periodicity of the array. Scale bars=50 μm;

(FIG. 15a) For negative α, the beads travel from the bottom of a micromagnet to the top of the adjacent one and, therefore, approach the junction from the top. For low α values (−30°), the beads continue to travel along the +direction. ((FIG. 15b) For positive α, the beads travel from the top of a micromagnet to the bottom of the adjacent one and, therefore, approach the junction from the bottom. For low α values (+30°), the beads continue to travel along the −direction. ((FIG. 15c) For α=−65°, the beads move onto the −direction, after crossing the junction. ((FIG. 15d) For α=+65°, the beads move onto the +direction, after crossing the junction. Scale bar=20 μm;

(FIG. 16a, b) Simulated potential energy landscape of 2.8 μm beads evaluated along the two possible trajectories, $\vec{r}_1$ and $\vec{r}_2$, for α=−30° and for α=−65°. These simulations were performed at the centre of the bead, i.e., in a plane Δz=2 μm above the micromagnets, for a micromagnet magnetisation of 80 kA/m and an external field with a flux density of 30 G. For α=−30°, the beads encountered a lower potential energy minimum along $\vec{r}_1$, and travelled along that direction (+). For high α=65°, the beads encountered a deeper and closer potential energy minimum along $i_2$, and therefore chose the −direction, provided that they had sufficient kinetic energy to overcome the potential energy barrier at 1.5 μm. (c) Percentage of 2.8 μm beads travelling along the +(light grey) and −(dark grey) directions for different magnetisation angles. The external driving frequency was 1 Hz. For negative α, the percentage of beads turning to the +direction increased until −45°. From α=−45° to −65° the beads started to select the micromagnets in the −direction. For α<−65° all beads moved onto the −direction after crossing the junction. The symmetric behaviour was observed for positively increasing a.

(FIG. 17a) Finite element calculations as a function of $\vartheta_{xz}$ showing the evolution of the potential energy at a tri-magnet junction (z-plane=2 μm above the MMA) for χ=0.17. The micrographs show the motion of a 2.8 μm SPM bead across the array as a function of $\vartheta_{xz}$. The bead was observed to travel along the +direction after crossing the tri-magnet junction, due to the lower potential energy minimum along this direction. (FIG. 17b) Finite element calculations showing the evolution of the potential energy at a tri-magnet junction (z-plane=3.35 μm above the MMA), and micrographs showing the motion of 5.5 and 2.8 μm SPM beads. The 5.5 μm bead travelled along the −direction after crossing the tri-magnet junction while the 2.8 μm bead continued to travel along the +direction. (FIG. 17c) Potential energy landscape calculated for the 2.8 μm beads along the $\vec{r}_1$ and $\vec{r}_2$ directions at the critical $\vartheta_{xz}$=−357.5°. The beads encounter an energy barrier along $\vec{r}_2$ at 1.5 μm that does not exist along the $\vec{r}_1$ trajectory. Thus, the 2.8 μm beads travel along the $\vec{r}_1$ trajectory although the potential energy landscape is relatively flat between 0.5 and 3 μm. (FIG. 17d) Potential energy landscape for the 5.5 μm beads evaluated along the two possible directions $\vec{r}_1$ and $\vec{r}_2$. The beads encounter a lower potential energy minimum along $\vec{r}_2$ and thus travel along that trajectory. (FIG. 17e) Fractions of 2.8 μm and 5.5 μm beads turning to the +direction for different magnetisation angles. *p<0.05; N. S. not significant (t-test). Error bars represent the standard error of the mean. Scale bars=20 μm;

(FIG. 18a) Schematic of the experiment in which the MDA-MB-231 cell was first focused and then guided back through a series of switches. (FIGS. 18b-d) The cell (thick arrow) labelled with magnetic beads moves in the positive x-direction and crosses a focusing junction. (FIGS. 18d-f) The orientation of the rotating external magnetic field is reversed to drive the cell backward. The cell chooses the −direction when crossing the junction for the second time, since the magnets were magnetised at α=30°. Scale bar=50 μm;

FIG. 22. The pulse width is remains constant for each particular frequency while peak to peak value of a signal represents the number of beads or size of the beads passing through the laser spot. In the case of smaller spot size, the peak to peak signal represents the size of the bead travelling across the magnet. In the case of larger spot size, if the number of beads passing through the laser spot are less than the number of micromagnets exposed in the field of view, the peak to peak value of a signal is less as compared to the more number of beads passing through the laser spot;

FIG. 27 Larger spot size: Comparison of beads with different magnetization;

FIG. 28 Larger spot size: Calibration curves.

FIG. 29: Signal output of photodetector using FOV3 (exemplary field of view 3) configuration for multiple 2.8 micron SPM beads emphasizing transport behavior in the presence of (i) and (v) no field, (ii) permanent external magnetic field with the magnetic flux density in xy plane as a function of external magnetic field frequency phase angles, θx=180 degrees, (iii) one-dimensional flipping external magnetic field in xy plane with phase angle θx, and (iv) two-dimensional rotating external magnetic field in xy plane around x-axis with phase angle θxz at 1 Hz.

FIG. 30: Signal output for different optical configurations at 1 Hz frequency of external rotating magnetic field. a) when one magnet is illuminated (FOV1) and b) when multiple magnets are illuminated (e.g. FOV3).

FIG. 31 Experimental measurements of the normalized optical signal for different populations of 2.8 micron beads for a) FOV1, b) FOV2, c) FOV3 and d) FOV4. The red lines present the theoretical prediction on the sensitivity based on equation 4.4. Approximately 50 beads were measured for each FOV.

FIG. 39 is a schematic diagram of an aggregation assay

FIG. 40 Detection of bBSA using opto-magnetophoretic system: a) Normalized amplitude at varying frequencies, b) comparison with flow cytometer.

FIG. 41 Detection of dsDNA using opto-magnetophoretic system: a) Normalized amplitude at varying frequencies, b) comparison with flow cytometer.

FIG. 42 Covalent functionalization of Silanized-biotin on MMA chip.

FIG. 45 Numerical simulations of equation in Matlab showing the numerical signal output from MMA in the absence of beads and 5.6 m beads captured on micromagnets using parameters. Bead velocity is considered to be 8 m/s with RP=0.15.

FIG. 46 Signal output of photodetector for heterogeneous assay specificity analysis. a) Streptavidin beads, b) carboxylated beads b) anti-rat antibody functionalized beads, and d) anti-rabbit antibody functionalized beads. Scanning is performed at 120 m/s.

SUMMARY

Figure 3:
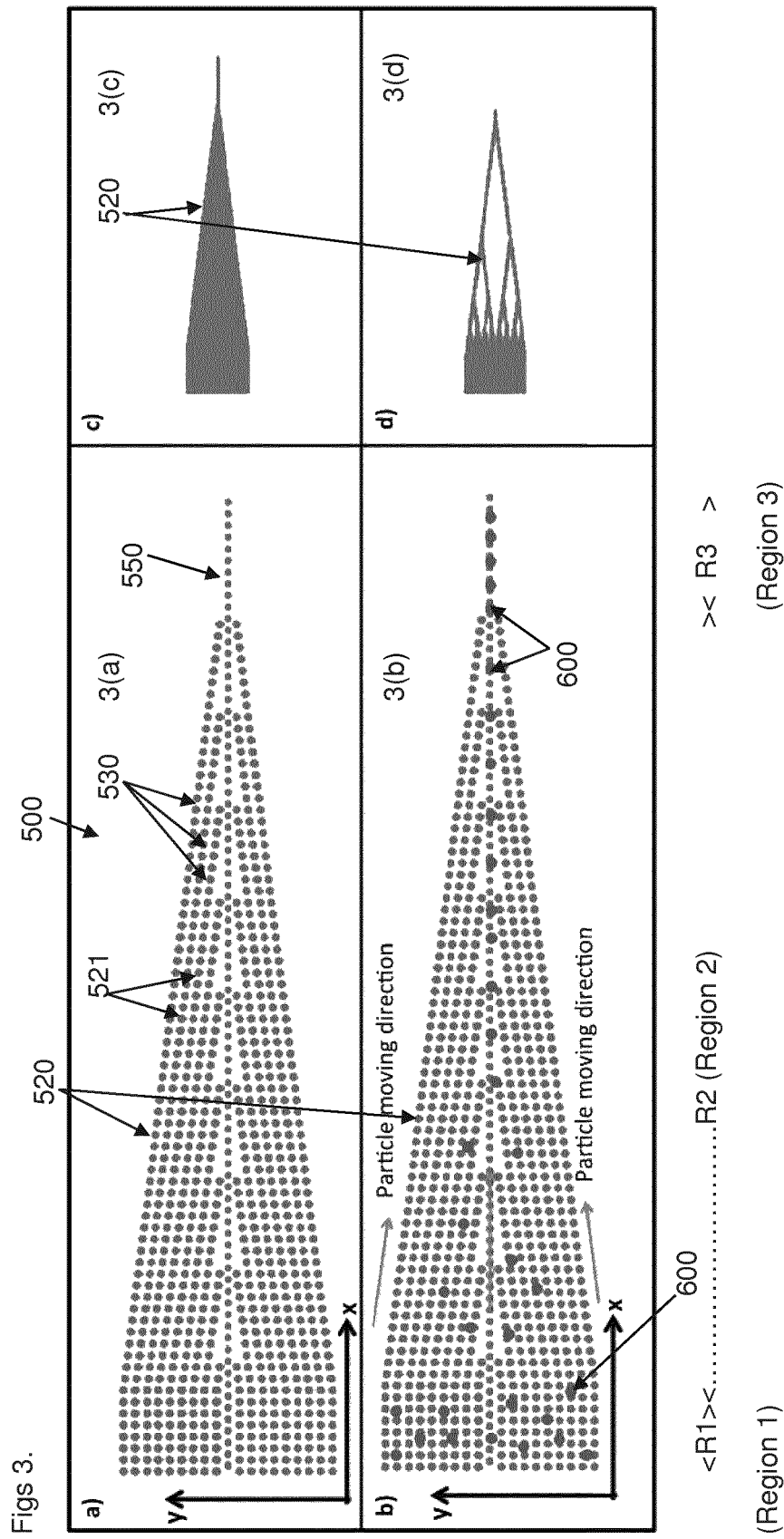
FIG. 3. Show focusing micro-magnets array arrangements according to the present specification FIG. 3a) The focusing MMA is composed of multiple micro-magnets lines that are arranged at an angle with the x-direction. External magnetic field drives SPM particles in the x-direction.

The present specification provides a method, system and substrate or chip for the separation and detection of at least one target analyte in a fluid sample, for example, a biological sample. The method and system are based on non-linear magnetophoresis and the chip or substrate is configured for use with such a system.

In one arrangement the specification provides a separation substrate device for use with an NLM separator in separating and/or detecting at least one target analyte in a sample, the substrate comprising a micromagnet array of a plurality of micromagnets, the micromagnet array comprising a first capture region, a second focusing region, and, a third detection region, the focusing region comprising a converging and/or diverging micromagnet array region, as provided in claim 1.

The array is described as converging or diverging in that the micromagnets or lines of micromagnets may be arranged to bring a sample to a particular area or target region. For example parallel lines of the array may be arranged to converge to a common target region relative to the input. The convergence or divergence may be to a common and relatively smaller detection region or target region smaller in area relative to a wider input region of the array.

The present specification in an exemplary arrangement provides a separation substrate or chip device for use with an NLM separator in separating and/or detecting at least one target analyte in a sample, the substrate comprising a micromagnet array of a plurality of micromagnets. The micromagnets define micro-mirrors. The micro-magnets have reflective properties. The micro-magnets are comprised of a metal. In a preferred arrangement the micro-magnets comprise Chromium. The micro-magnets may be comprised Cobalt with a layer of Chromium provided on the Cobalt. The micromagnet array may include a plurality of micromagnets in a rectilinear arrangement.

Further features are provided in accordance with dependent claims 2 to 29.

The present specification provides improved chip or substrate devices for use in the separation and detection of magnetic particles and target analytes in a sample, in particular a biological sample. In one arrangement the substrate is advantageously configured to provide the transport of particles or beads or aggregates of different type to different locations of the substrate. In one arrangement the substrate is advantageously configured to provide the separation and detection of the controlled transport or motion of particles.

A method is provided in accordance with claims 30 to 37. The method provides for controlled separation and transport of particles or beads or aggregates of different type for example to different locations of the substrate.

Systems in accordance with claims 38 and 39 are provided. Further features are set out in the dependent claims 40 to 91.

According to a further aspect a method for separation and detection of a target analyte is provided in accordance with claim 92. Further advantageous features are set out in dependent claims 93 to 104.

DETAILED DESCRIPTION

The separation and detection system 100 of the present specification is based on non-linear magnetophoretic (NLM) and or flow enhanced non-linear magnetophoretic (FNLM) transport of magnetic particles or magnetic micro-particles P the system 100 further including an integrated optical detector. To effect separation and detection, the magnetic particles, at least some of which are bound to a biological substance, are provided adjacent a plurality of micro-magnets provided on a substrate and an external travelling magnetic field is applied thereto. The micro-particles are translated over the surface of the substrate under the dual influences of the travelling magnetic field and the fixed micro-magnets of the arrays. Non-linear magnetophoresis (NLM) and its enhanced version, flow enhanced NLM (FNLM) use travelling magnetic field waves created by combination of periodic micro-magnets array (MMA) and external rotating magnetic field, has been shown to provide very high sensitivity for the separation of magnetic micro-particles and biological analytes.

In the specification, the terms micro-particles P or 600, magnetic micro-particles, superparamagnetic (SPM) particles or SPM beads are variously used to describe the particles which are provided, functionalized to bind with specific analytes, and added to a sample and aggregates which are formed in the presence biological materials. The samples used with the presently described systems and methods include biological samples labelled with SPM beads. In the specification, the terms array, micro-magnet array MMA, chip and focusing micro-magnet array MMA/FMMA have variously been used to describe the micro magnet arrays used for separation.

A micromagnet array typically comprises a group or a plurality of spaced apart micro-magnets. The MMA is composed of periodic magnetic lattice or structures with micro-sized individual micro-magnets. Ferromagnetic materials are used to construct the micro-magnets in order to achieve stable and strong local magnetic field. The MMA is configured for manipulation and separation of a range of SPM particles in a highly controlled manner. In the arrangements described the micromagnets, are circular and have a diameter of the order of 5 micron. The diameter is selected to be comparable with the sizes of the particles to be separated or detected. While in the arrangements described the micromagnets are of circular form it will be appreciated that other suitable forms may also be used. It will be appreciated that the diameter or dimensions may be varied, as required. To maximize the reflection from the MMA to photodetector, the micro-magnets may be fabricated with a highly reflective metal to create micro-sized mirrors on the substrate. The substrate is selected to have relatively low reflectivity compared with metal micro-magnets to create a maximized modulated signal in ONLM in the presence of SPM particles.

The system 100 provides for the separation of a sample to which micro-particles have been added and for detection of aggregates and analytes in the sample. The system 100 comprises a separation and detection system 100 based on non-linear magnetophoretic separation. In the exemplary arrangement of FIG. 1 the detection system in an optical detection system and the arrangement is referred to herein as Opto-Non-Linear Magnetophoresis (ONLM) device. The system 100 comprises in an integrated device an optical detector 200 an NLM/FNLM separator 300 to perform sensing of SPM particles simultaneously while the NLM/FNLM separator separates the SPM particles. A chip or substrate 310 comprising a micromagnet array 320 is provided for use with the separator and detector system 100. In operation, the substrate is loaded into the separator and detector system 100 and a sample is introduced to the substrate. More details about an NLM/FNLMs chip and external magnetic field set-ups can be found for example in WO2012/004363.

Referring to FIG. 1(a), an exemplary arrangement of an integrated detection and separation system (ONLM) 100 according to the present specification is described. The system 100 comprises an NLM or FNLM separator 300. The separator 300 may comprise an NLM separator or a flow enhanced NLM separator. The separator is configured to receive a separation chip or substrate comprising a micromagnet array comprising a plurality of micro-magnets provided on the chip and an external travelling magnetic field is applied thereto. The micro-particles are translated over the surface of the substrate under the dual influences of the travelling magnetic field and the fixed micro-magnets of the arrays. The system 100 further comprises a light source 210. In a preferred arrangement the light source 210 is a laser source and optical components 220 to direct the light to the substrate or chip. In one arrangement, the optical components 220 comprise a dichroic mirror 221, lenses 222. The system 100 further comprises a detector 230. In the exemplary arrangement, the detector comprises a photodetector 230.

The separator 300 comprises an NLM or FNLM separator. An NLM/FNLM chip 310 is provided comprising micromagnet array (MMA) 320. In the exemplary arrangement the MMA 320 is comprised of micro-magnets 321 defining an array. Spaces 322 or gaps 322 are provided between the adjacent micro-magnets. The micro-magnets 321 comprise metal micro magnets. The metal micro-magnets 321 provide a local magnetic field to drive the magnetic particles P to be separated and detected. The micro-magnets 321 of the MMA 320 further are arranged and configured as micro-mirrors 323 to reflect the incident light (from the light source 210) from the chip or substrate to detector 230. The micro-magnets 321 are configured to be reflective by the selection of a metal having high reflectivity. In the exemplary arrangement, magnets 321 may be comprised of a Cobalt material coated with Chromium. A high transparency layer 324 for example, of Silicon dioxide or polymer material is provided on top of micro-magnets 321. In a further arrangement the surface of micro-magnets 321 of an array 320 may further be functionalized for binding with a selected target analyte for example a biomaterial.

In operation, the incident light from light source 110 of the optical detection system 100 is focused on the micromagnet array MMA 320 and is reflected back to photodetector 230 of the system 100. The magnetic micro-particles P appear optically black in comparison with the micro magnet array MMA 320.

In the system of the present specification the microparticles P comprise superparamagnetic particles. In the presence of SPM particles P on top of micro-magnets 321, the incident light from incidence laser 110 is scattered and absorbed. Accordingly, the reflectivity of MMA 310 is changed by the presence of the SPM particles P in comparison compared with the bare MMA 310 (having no SPM particles or beads).

Effectively the present specification in an exemplary arrangement provides a separation substrate or chip device for use with an NLM separator in separating and/or detecting at least one target analyte in a sample, the substrate comprising a micromagnet array of a plurality of micromagnets. The micro-magnets define micro-mirrors. The micromagnets have reflective properties. The micro-magnets are comprised of a metal. In a preferred arrangement the micromagnets comprise Chromium. The micro-magnets may be comprised Cobalt with a layer of Chromium provided on the Cobalt. The micromagnet array may include a plurality of micromagnets in a rectilinear arrangement.

The detector 130 detects light reflected from array 310 before the particles P are introduced and during separation. The initial reflected light signal $S_{Initial}$ is detected before the sample is provided to the array and reflected light signals $S_{Separation}$ are detected during the course of the separation. By detecting the difference of reflective light signal without and with micro-particles P on MMA 320, then information about the particles P is obtained. The intensity of light reflected from the chip or substrate to the photodetector 130 is dependent on MMA 320 surface properties, fluid, and number of micro-particles P, dimension of particles, and optical properties of the particles. By virtue of the integration of the detection system 100 with the NLM/FNLM separator 300, the SPM particles P can be manipulated and moved on MMA 320 in controlled manner by controlled application of different rotation frequencies of rotating magnetic field. As SPM particles P move across on MMA 320, they periodically modulate the reflective light from the micro-magnets/micro-mirrors 321. Therefore the output signal of the detector 130 is modulated by the motion of SPM particles on MMA 320 by controlling of rotation frequency of rotating magnetic field.

For example, when SPM particles P move to the gaps 312 between adjacent micro-mirrors 311, as shown in FIG. 2(a), the intensity of reflective light from MMA is at a maximum. But when particles P move directly over or onto the top of micro-mirrors 321 as the phase of rotating magnetic field is varied, as shown in FIG. 2(b), the intensity of reflective or reflected light is decreased to minimum. As a result, when particles move from one micro-mirror 321a to another micro-mirror 321b as driven or controlled by external rotating magnetic field, the output of detector 130 periodically changes, as shown in FIG. 2(d).

The difference or change of peak-to-peak voltage ($V_{pp}$) output of signal of photodetector 130 on the ONLM system 100 reflects the quantity, dimensions, and optical properties of particles P at particular selected moving speed of particles on the MMA 320. The frequency of the detected signal is related to and dependent on the rotation frequency of external magnetic field, as well as the moving speed of particles P. The moving speed and immobility of particles/SPM particles can be controlled by rotation frequency which is controlled for the particles of interest.

Considering the example of a sample including particle type 1 and particle type 2, at low rotation frequency, the particles move at a speed proportional to the rotation frequency. As the rotation frequency increases to a rotation frequency greater than the critical frequency of a particle type 1, the particles type 1 start to decrease their speed and the proportion of particles which are immobilized also increases, until the immobilization frequency is reached, at which frequency all particles type 1 are completely immobilized on MMA and no longer move, as shown in FIG. 2(c). As a result, the $V_{pp}$ output of photodetector 130 of the ONLM system 100 starts to decrease from the critical frequency to a minimum at a rotation frequency higher than the immobilization frequency, due to all particles are immobilized between the gaps of micro-magnets, as shown in FIG. 2(d) (iii). Based on the fact that different SPM particles or magnetic objects have different critical frequency, immobilization frequency, and immobilization fraction at certain frequency, the properties of SPM particles and objects in a sample can be recognized by analyzing the frequency response of output signal of the ONLM system 100.

The system 100 and method provide for the sensing of SPM particles and for detection of information about the particles, such as, quantity, dimensions, and optical properties. The system also provides for differentiating of different SPM particles (with or without biological bond), while separating them in NLM/FNLM separator 100 simultaneously.

The photodetector 130 may in an exemplary arrangement be located above the MMA in order to detect the reflective lights and to acquire modulated signals. Alternatively, the photodetector may in an exemplary arrangement be located beneath the MMA, for example in case of using of a transparent MMA chip 310'. The transparent MMA chip 310' comprises a transparent substrate 325, of a material such as glass, and MMA 310', is similar to chip 310 as described above. The optical path is changed as required to accommodate the photodetector beneath the MMA 310'.

In this arrangement, the motion of magnetic micro-particles P affects or modulates the transmitted light from light source 110 to the photodetector 130 as compared with that of the reflected light in the arrangement as described above. In the system 100, the transmitted light intensity is modulated by motion of SPM particles. As described above the modulation is controlled as appropriate for detection of particular particles and analytes, as required. The optical detection system is sensitive to SPM particle properties and their motion on NLM/FNLM chip, which is driven by the NLM or FNLM separator. By analyzing the output signal response of photodetector to the chip surface's condition, particles properties, and motion of particles, which is associated with particles magnetic properties and hydrodynamic drag factors in term of rotation frequency, the information about particles dimension, optical properties, quantity, and as well can intrinsic NLM property be obtained. To detect the biological species, the particles may be functionalized with biological attachments, thus the changes of reflective light may be detected by the mean of changes of dimensions, optical properties, and magnetic properties in presence of biological species. Furthermore, the detection may be carried out in real time with the separation process by NLM/FNLM separator 100.

The opto-magnetophoretic system is presented that is capable of quantitative detection of SPM beads traveling on a MMA chip with high sensitivity and a wide dynamic range. The SPM beads, phase-locked with the external rotating magnetic_field, to traverse synchronously across the MMA chip producing a unique periodic change in the photodetector signal based on their size, optical and magnetic properties. The system was used to detect single beads and population of beads at different external magnetic field and rotation frequencies rotation frequencies. This system was able to characterize bead movement across the full-range of NLM transport behavior. Further examples are provided in the specification.

Precise sensing and separation on multiplex magnetic micro-particles or biological species simultaneously is a challenge for conventional lab-on-a-chip technology. For example, a lab-on-a-chip based optical particle detector for micro-fluidic application typically would require precise hydrodynamic particle focusing, which is still a challenge for fast and large amount of particle detection. In contrast, the system and method of the present specification provides an effective tool to detect and separate multiplex magnetic micro-particles and biological materials simultaneously with high precision. Furthermore, the system and method of the present specification delivers a sensitive method to separate and detect the micro-particles by using very simple and easy construction of instrument without requiring an expensive optical sensor needed. It also provides an efficient approach for development of inexpensive, portable, multiplex separation and detection, and high resolution lab-on-a-chip instrument for point-of-care diagnosis and analytical applications.

While in FIG. 1 and in the earlier related applications various forms of regular for example rectilinear lattice form arrays are provided, the present specification further provides a converging array 500 described for example, with reference to FIGS. 3, 12 and 13, 14a, 14g and 18. The present specification further provides an alternative form of micro-magnet array for use in the systems and methods of the present specification.

The substrate 500 comprises an array 501 of FIG. 3 comprising a focusing or converging array. The array 501 is formed to achieve on-chip particle focusing to provide an improved detection of a large amount of particles. The array 500 of the exemplary arrangement of FIG. 3 comprises micro-magnets 502 arranged on micro-magnet lines 503, the lines 503 have an angular alignment so that they converge, or, in other words are focused to a sensing area 510.

In this approach, the optical detector is focused on a fixed sensing area 510 of the array and the particles are moved and focused to this sensing area 510 such that they are detected by optical detector. Without the requirement of hydrodynamic flow or any other changes in the optics and the external magnetic field, the optical detection is carried out as described above, for the regular periodic MMA. The focusing of particles P allows more particles to be detected in the sensing area within a limited period of time without moving the optical detector or the MMA chip 500. Thus, improved efficiency of detection of the particles is provided. The on-chip travelling magnetic wave focusing is based on the NLM transport of SPM particles on micro-magnets lines 503 that have and angular alignment relative the major axis in the exemplary arrangement of the drawings to the longitudinal axis (designated X axis) of the array 501 so that they converge, hence be "focused" to detection area 510. As shown in FIG. 3 (a), the micro-magnets lines have been arranged with a certain angle with the x-direction (Assuming in the regular lattice-like MMA, the SPM particles travel in x-direction under control of the external field) to allow them to be focused in one direction. On these converging micromagnets lines 503, the rotating magnetic field transports the SPM particles P 600 in the same fashion as on a regular lattice form or rectilinear MMA, as described above. When SPM particles P are driven forward in x-direction, they are driven to follow the micro-magnets lines 503 instead of moving straight in the longitudinal direction (X-axis) of the chip, as the array is configured such that for a particle at micro-magnet 502A then micro-magnet 502B located on the same line is the nearest micro-magnet. As a result, the SPM particles can be focused from the back-end to the front-end of the converging MMA, as shown in FIG. 3 (b). As described previously, in the presence of the external rotating magnetic field, SPM particles tend to be trapped inside of potential wells which are created by the MMA and the external magnetic field. When a travelling magnetic field wave is generated by the rotating field, SPM particles start to follow the nearest potential well, which travel as waves on the MMA, and move across the MMA. In the converging micro-magnets line 503 arrangement, the nearest moving potential well for a particle is located on adjacent micromagnets 502A and 502B in the same micro-magnets line 503, due to the closer distance between two micro-magnets in same line compared to the distance between two micromagnets in different lines. Thus, SPM particles always tend to move on the same micro-magnets lines instead of jumping over to adjacent lines while travelling with the magnetic field wave on the MMA. Multiple angularly-aligned micro-magnets lines arranged in a large area can be used to achieve an efficient on-chip particle focusing. Different arrangement of micro-magnet lines can be used to form a large focusing MMA. In a first exemplary arrangement, the MMA is simply composed of multiple micro-magnets lines aligned with a specific angle in a large area, as shown in FIG. 3 (c). The second exemplary arrangement uses a tree-like hierarchical arrangement of multiple micro-magnets lines, as shown in FIG. 3(d). Referring to FIG. 3(d) multiple MMAs are arranged in a tree structure to allow multi-step focusing. In both arrangements, the particles are dispensed from the left-end of MMA and are focused towards the right-end of MMA as a result of the rotating magnetic field.

Referring to FIGS. 14a and g two schematics that show two exemplary converging micromagnet array arrangements according to the present specification are described. Each of the MMAs 520 is comprised of three regions: Region 1 is configured, and in operation is used, to capture beads of a sample and comprises an MMA of rectilinear form. Region 1 comprises a capture region. The MMA in the exemplary arrangement is comprised of 5 μm-diameter circular magnets with 8 μm centre-to-centre distance; Region 2 is configured, and in operation is used, to focus the beads of a sample.

Region 2 is a focusing region and comprises lines 530 of magnets 521 arranged at an angle to the x-axis of the MMA and converging to a sensing region of the MMA. The lines 530 may for example be arranged at an angle of the order of 5-15° to the x-axis. In an exemplary arrangement the lines 530 may be arranged at substantially ±7° with respect to the x-axis. The lines 530 converge into a single line 550 of micromagnets. The MMA further comprises a third sensing region—region 3. The sensing region 550 is comprised of a single or line row of magnets 531 and ideally is the location where an optical sensor would be placed. In the exemplary arrangement of FIG. 14a, region 2 is comprised of densely packed lines of magnets (FIG. 14a); whereas in the exemplary arrangement of FIG. 14g, region 2 is comprised of a tree-like structure in which the focusing process takes place in consecutive steps (FIG. 14g).

Size and magnetisation-based separation can be achieved by increasing the frequency of the travelling magnetic field to a speed where the hydrodynamic force exceeds the magnetic force. A critical frequency, $\omega_c$, exists for a SPM bead $$\omega_c = \frac{\chi \mu_0 \sigma_0 (H_{ext})}{18 \eta} (2\pi\beta)^2 e^{-2\pi\beta},$$

where $\sigma_0$ is the effective magnetic moment of the micromagnets, $\eta$ is the viscosity of the surrounding medium, and $\beta$ is the ratio between the bead's radius, r, and the centre-to-centre distance between adjacent magnets, d. The critical frequency is the frequency at which the average velocity of the beads starts to differ from the average velocity of the translating magnetic field, $\omega d/2\pi$. The advantages of the NLM separation technique are four-fold: high-resolution separation, parallel separation on the ca. $10^5$ micromagnets per cm², no fluid consumption, and the capacity to work with high bead densities. The combination of MMA and rotating fields has been used for on-chip cell manipulation. Using engineered microstructures, the controlled transport, assembly, and isolation of both labelled and non-labelled cells have been recently demonstrated. Bead trajectories can be tuned by properly adjusting the design of the MMA or the orientation of the applied rotating field. The capabilities of this separation technique, in terms of resolution, efficiency, and potential for multiplexing, make it an attractive option for bead-based LOC devices.

The $V_{pp}$ voltage output of detector/photodetector 130 on ONLM 100 associated with intensity of reflective light in the case of without particles can be defined as $I_o$. For certain number, N, of SPM particles with radius, a, on MMA, The signal with the particles directly on top of metal micro-mirrors is defined as $I_1$. The signal with the particles on the gaps between adjacent micro-mirrors is defined as $I_2$. At low rotation frequency, all the particles are movable, therefore the actual output of ONLM fluctuate between $I_1$ to $I_2$. Assuming the signal created by reflective light from particles and silicon substrate can be neglected, due to low reflective light from them, then $I_1=I_o-N\pi a^2$, $I_2=I_o$. So, the peak, as indicated as (i) in FIG. 2(d), and valley, as indicated as (ii) in FIG. 2(d), in the periodic output signal of photo-detector on ONLM, as shown in FIG. 2(d) represent the $I_1$ and $I_2$, respectively.

With calibrated signal, the quantity and dimension of SPM particles can be measured by ONLM at certain low rotation frequency of rotating field.

At increased rotation frequency, the proportion of immobilized SPM particles increases and all particles are completely immobilized on MMA at their immobilization frequency. In term of $V_{pp}$ output of ONLM, output is decreased as the quantity of particles immobilized between gaps of micro-mirrors is increased as rotation frequency increased. For different SPM particles, the immobilization frequency, $f_i$, which corresponds the minimum $V_{pp}$ output of ONLM, as defined as background signal, Vo, is different. Furthermore, the signal amplitude for different micro-particles decreases at different decreasing rate.

The present specification presents an optical detection system 100, arrangement integral with an NLM or FNLM separator 200, configured and operable to sense an optical signature produced by the SPM particles on NLM/FNLM chip 210.

The NLM/FNLM chip 210 has periodic array of micro-mirrors 211, which also play role as micro-magnets array (MMA) to create a travelling magnetic wave on the chip surface.

The magnetic SPM particles can be moved on NLM/FNLM surface in controlled manner by external rotating magnetic field. The optical detection system incidence laser to the surface of MMA and detect the reflective light back to photodetector. The optical detection system is sensitive to SPM particle properties and their motion on NLM/FNLM chip, which is driven by the NLM/FNLM separator. By analyzing the output signal response of photodetector to the chip surface's condition, particles properties, and motion of particles, which is associated with particles magnetic properties and hydrodynamic drag factors in term of rotation frequency, the information about particles dimension, optical properties, quantity, and as well as intrinsic NLM properties can be obtained. To detect the biological species, the particles may be functionalized with biological attachments, thus the changes of reflective light may be detected by the mean of changes of dimensions, optical properties, and magnetic properties in presence of biological species. Furthermore, the detection can be carried out in real time with the separation process by NLM/FNLM separator 100.

The present specification presents the structure of an optical detection system 100, which is composed of: at least one light source 110 to illuminate the MMA 320 or 520 on NLM/FNLM separator 200, a periodic micro-magnets array 320/520 (micro-mirrors) on NLM/FNLM chip 310/510, at least one photodetector 110 to sense the reflective light from micro-mirrors surface, suitable optical parts, such as mirrors, objectives, to align and aid the light path, and suitable signal acquisition and processing electronics and software. The effective detection should be incorporated with suitable NLM/FNLM separation system, which is described in reference herein referred.

The present specification also provides detection of SPM particles and their aggregates which are formed in presence of inter-particles biological materials. It also presents biological sensing of functionalized bio-materials on the MMA surface by using the detected difference of ONLM signals for functionalized areas, in where the SPM particles are specifically bonded to the areas, and non-functionalized areas, in where the SPM particles are movable.

The schematic of configuration of present invention is illustrated in FIG. 1. The Optical detection system 100 is a portable integrated device incorporated with NLM/FNLM separator to perform SPM particle sensing while the NLM/FNLM separator separates or focuses (when using the focusing MMA) the SPM particles simultaneously. The ONLM is aligned with optical window of NLM/FNLM separator, which will be described further herein below. To construct an effective ONLM, which is integrated with NLM/FNLM separator, at least one laser light source is required to illuminate the MMA and create the reflective light as well. At least a photodetector is required to detect the reflective light from the MMA. The optical lenses are used to focus the laser to the MMA and collect the reflective light to photodetector. A dichroic mirror is mounted in the light pass of laser and photodetector to allow the laser incidence to the MMA and reflective light from MMA to go to photodetector without interference of incidence laser. For multiplex sensing, more than one laser and photodetector can be used. The fluorescence labeled particles are also can be used for this purpose. In the case of multiplex sensing, the suitable beamsplitters and filters may be used to guide different light from laser to MMA or from MMA to photodetector. Alternatively, the CCD camera other light source with suitable mirrors in light path can be used for imaging and visualization of particles and MMA surface. An automated x-y stage or positioning stage may also be provided to incorporate the separator and optical detection system. This arrangement supports automated scanning of whole MMA surface for large scale sensing. It also provides a way to differentiate the local difference of reflective light outputs on MMA. That will be used for potential multiplex sensing, if MMA is functionalized by multiple bio-layers. If the on-chip focusing MMA is used instead of regular lattice MMA, the position of the optical detector can simply be fixed such that it is focused on the sensing area on the MMA, where the focused particles are located. Exemplary arrangements will be further described below.

To minimize the interference of ambient light, a suitable light shield may be applied. Various details of a structure and set-up of NLM/FNLM separator and system according to arrangements of the present specification are described herein below.

Example 1

Example 1. Exemplary Arrangement of an ONLM System of an Arrangement According to the Present Specification An ONLM system is provided in accordance with the exemplary arrangement as illustrated in FIG. 1(*b*). A 635 nm laser source installed on a laser mount which is operated with 10 mW power by a laser diode driver, providing the incidence light through an objective above the NLM/FNLM separator. A photodetector with built-in transimpedance amplifier and switchable gain settings is used to detect the reflective light from MMA of NLM/FNLM separator. The photodetector is sensitive to wavelength from 300 nm to 1100 nm. Laser and photodetector are mounted orthogonally in light path. A dichroic mirror is mounted in the light pass of laser and photodetector to allow the laser incidence to the MMA and reflective light from MMA to go to photodetector without interference of incidence laser. Alternatively, a CCD camera and a halogen light source (100 W in power) are also mounted through a 50/50 beamsplitter and switching mirror in light path for imaging and visualization particles and MMA surface. The output of photodetector is recorded and monitored in real time with sampling rate of 625 kSa/s and a built-in low pass filter. Software is provided and used to process and analyze the output data. In additional, imaging software is used for imaging processing. Ambient light interference is minimized.

Example 1: Arrangement of the Micro-Magnets Array (MMA), NLM/FNLM Separator, and the Focusing MMA According to an Arrangement of the Present Specification The MMA and NLM/FNLM chip 310 is configured to provide control of motion of magnetic micro-particles in rotating magnetic field. The MMA is composed of periodic magnetic lattice or structures with micro-sized individual micro-magnets. Ferromagnetic materials are used to construct the micro-magnets in order to achieve stable and strong local magnetic field. The MMA is configured for manipulation and separation of a range of SPM particles in a highly controlled manner. To maximize the reflection from the MMA to photodetector, the micro-magnets are fabricated with high reflective metal to create micro-sized mirrors on substrate. The substrate is selected to have relatively low reflectivity compared with metal micro-magnets to create a maximized modulated signal in ONLM in the presence of SPM particles. The top layer on the MMA, which acts as protection layer and adjusting layer for local magnetic field for MMA may be selected to be optically transparent and chemically inert. Further to provide a FNLM chip according to an arrangement of the present specification and to introduce the flow onto MMA, a transparent flow chamber may be provided to enclose the MMA. The flow inlets and outlets are drilled on the chip. Other shapes of MMA, such as square, rectangular, triangle, and lines, etc. can be used to transport the SPM particles and produce modulated reflective light to ONLM for detection. In the case of using the optical detector with the focusing MMA, a converging MMA 520 is provided. A single area converging MMA may be used for single-step focusing and a tree-like structure of angularly-aligned MMAs may be used for multi-step focusing, as shown in the exemplary arrangements of FIGS. 3(*c*) and (*d*). The properties and structures of micro-magnets are similar to those in the regular lattice-like MMA.

Example 2. Fabrication of the Micro-Magnets Array, Separator, and the Focusing MMA According to an Exemplary Arrangement of the Present Specification An MMA may be fabricated by using conventional photolithographic lift-off process. The micro-magnets were circular cobalt domains of the order of 5 μm in diameter. Two 10 nm thick chromium layers were deposited underneath and above the cobalt domains as adhesion layer and protection layer, respectively. For lattice-like MMA (without focusing functionality), the magnets were spaced with 3 μm (8 μm from center-to-center) in a rectangular array to form the magnets array on silicon substrate. The magnets were spaced with 3 μm (8 μm from center-to-center) in a rectangular array to form the magnets array on silicon substrate. A 600 nm thick silicon dioxide is coated on to the magnets array by plasma enhanced chemical vapor deposition. The layer of silicon dioxide will create a flat and uniform surface of magnets array and decrease the adhesion of magnetic particles on surface. To build a FNLM chip, a transparent flow chamber may be provided to enclose the MMA. The flow inlets and outlet may be drilled on the chip by mechanical means. Furthermore, micro-magnets with shapes of square, rectangular, triangle, and lines, etc. may be fabricated by using the same technology on silicon, glass, or plastic substrate. For the focusing MMA of an exemplary arrangement according to the present specification the micro-magnets lines are tilted in the order of 7° with respect to the major axis direction (x-direction in FIG. 3). The dimensions of micro-magnets are similar to those in the lattice-like MMA. The center-to-center distances between adjacent micro-magnets in the same line and between adjacent micro-magnets in different lines are of the order of 8 μm. While in the above noted example, it is provided that the micro-magnet lines are arranged at an angle of the order of 7 degrees with respect to the major or longitudinal axis of the chip, it will be appreciated that the lines may also be arranged at other suitable angles.

Example 3. Enhanced Signal to Noise (S/N) Ratio of ONLM by Using MMA with Improved Optical Reflectivity, According to an Exemplary Arrangement of the Present Specification As described previously, the micro-mirrors 321, 521 on MMA 320, 520 are configured to reflect the light back to the photodetector in the ONLM system while the substrate 310, 510 supporting the array or micro-mirrors may be relatively less reflective compared with micro-mirrors. Thus, the effect of interference by substrate can be reduced as the SPM particles move on the micro-mirrors or on the array. To enhance S/N ratio of ONLM system, the substrate 310, 510 of the MMA 320, 520 may be fabricated by using less reflective materials rather than silicon, which is more reflective. Alternatively, anti-reflective coatings may be deposited on the substrate to reduce the intrinsic reflective light from substrate. The S/N ratio is accordingly increased by using more highly reflective materials for micro-reflectors (MMA) and less reflective materials for the background or substrate.

Sensing Process According to an Exemplary Arrangement of the Present Specification Referring for example to FIG. 4*a* SPM particles P or their aggregates may be prepared prior to introducing into separator/detector 100. After introducing the SPM particles into NLM/FNLM chip, the external rotating magnetic field is applied to control movement of specific target particles. The rotation frequency is swept from low to high and the output signal of the ONLM detector system is recorded in real time. In terms of separation of SPM particles in real time, the rotation frequency also can be swept from high to low.

On-Chip Focusing Process: According to an Exemplary Arrangement of the Present Specification In the case of using the focusing MMA 520, SPM particles are dispensed onto the back-end of the focusing MMA. This can be achieved by using a long focusing MMA design. Then the rotating magnetic field is applied at a frequency lower than a particles' critical frequency. This drives the particles to move along the focusing MMA and the particles are thereby focused towards the front-end of the focusing MMA, where the optical detector is aligned.

Discrimination of Different Types of SPM Particles: According to an Exemplary Arrangement of the Present Specification Based on differences of their dimensions, optical properties, and NLM transport, mixture of different SPM particles may be detected by the ONLM system based on the arrangement that the frequency response of ONLM is different between different particles. Furthermore, fluorescent labels may be used to label different particles and allow multiplex detection due to different signal response in specific light spectrum by mean of using multiple wave length sensitive photodetectors and multiple lasers in ONLM.

SPM particles have been used for detection. The SPM particles used in the methods and system of the present specification may have various properties and dimensions. To achieve sensitive detection, the diameters of SPM particles need to be comparable with the size of the micro-magnets used. The magnetic properties of particles are also optimized to achieve stable NLM transport and high efficiency of separation. To effectively detect the biological species, the SPM particles are typically functionalized by target biological analytes to change their NLM fingerprints by means of for example changing dimension or magnetic properties. The target biological analytes also can form inter-particle linkers between particles and create a certain number of the chains or aggregates in suspension in presence of external magnetic field. The NLM transport of particles suspended with different ratios of aggregates can be discriminated according their different group immobility on MMA.

An application of the arrangements of the present specification includes a sensing device for sensing of target biological materials. The system provides discrimination of the presence of target biological materials from background noise by exploiting the transport mechanism of arrangements of the present specification as described above and analyzing the frequency and intensity spectrum of output signal of ONLM in order to differentiate the target biological materials attached to the SPM particles in suspension. Generally, there are two ways that target biological materials can change the NLM transport and magnetic mobility of the particles, i.e., the attached biological materials changes the dimension of the particles and inter-particles biological linkers create the magnetic chains or aggregates, which have different magnetic moment and dimensions compared with single particles. When the dimensions of particles changed, the optical properties of particles are also changed therefore, the reflective light intensity from MMA to ONLM is changed as well. Thus the output of ONLM system 100 can be changed in the frequency spectrum. Therefore, the frequency response of output signal of ONLM can also be changed due to different immobility of samples with different proportion of aggregates. The efficient NLM/FNLM separator underneath the ONLM makes sensing of biological species more accurate and efficient by mean of putting target biological materials attached SPM particles and un-attached SPM particles into optical sensing area in sequence by using separation. Accordingly, the output signal of ONLM for biological materials attached SPM particles and un-attached SPM particles can be differentiate to achieve sensing of biological species quantitatively. The quantity of biological species can be detected in well calibrated measurement.

The alternative approaches can be used by the arrangements of the present specification for detection of bio-materials, specifically functionalized on the SPM particles and in patterns on the surface of MMA on NLM/FNLM separator. The concept of detection is based on the specific affinity bonding between bio-materials on the MMA surface and functionalized SPM particles, e.g., the functionalized SPM particles can be specifically captured by the area functionalized with targeted bio-materials while non-functionalized area on the chip don't have specific bonding with functionalized SPM particles leaving movable particles in this area. The capturing of particles is considered to be relatively strong and provides that particles may be captured on the functionalized surface even in the rotating magnetic field, further the particles still may be manipulated by NLM transport in presence of rotating magnetic field on the MMA surface where no target bio-materials are coated. In the presence of an external rotating magnetic field, this creates the patterned areas on the MMA surface, e.g., the areas coated with bio-materials have captured particles while the areas without the bio-materials have moving particles. The ONLM system may be used to scan the whole area in controlled manner by moving ONLM or MMA with programmed motorized stage. The signal differences of ONLM detection corresponding to those patterned areas are compared in order to sense the specific bonding of the particles to bio-materials. In this way, the bio-materials may be easily detected using the ONLM system 100. This approach may also be used detect more than one bio-materials at same time, by using multiple functionalized particles and patterning multiple bio-materials on an MMA. Each type of bio-materials is specifically bound to designate particles in this case.

Example 4. SPM Particles and Assembly of Magnetic Aggregates, According to an Exemplary Arrangement of the Present Specification To demonstrate a system and method according to an exemplary arrangement of the present specification, SPM particles of 2.8 µm and 1.0 µm diameter (Dynabeads M270 Streptavidin coated and dynabeads MyOne streptavidin coated, Invitrogen, Carlsbad Calif., USA) were used. The coefficients of variation (CV) of diameters are less than 3%. Measured susceptibility of particles was about 0.17 and 0.3 for 2.8 µm and 1.0 µm, respectively. The particles were dispensed into 1 mM phosphate buffered saline (PBS) with 0.1% Tween 20 (PBST) with particle concentration of $10^7$/ml. To effectively detect the biological materials, the SPM particles have been incubated with Biotin/BSA at different concentration. The volume of Biotin/BSA in PBST and volume of particles in PBST suspension are the same in the preparation process. The detail of process is described as following as shown in FIG. 4(a): Mix 100 µl streptavidin coated dynabeads M270 particles ($10^7$/ml in PBS (0.1% Tween) with 100 µl Biotin/BSA (in PBST) with desired concentration of Biotin/BSA in a centrifuge tube. Then the mixture was rotated for 10 minutes on rotatory wheel. After rotation, permanent magnet was used to attract the magnetic particles in mixture on the side wall of tube. This step was used to make the particles contact thoroughly with each other. Then the mixture was vortexed to allow the particles re-dispense in the solution. The steps of applying magnet and vortex were repeated two times to complete the preparation of aggregates formation. The made suspension was vortexed before using for detection. In presence of external magnetic field, the Biotin/BSA form inter-particle linkers to link the streptavidin particles. Depending on the number of particles and concentration of Biotin/BSA in suspension, certain percentage of aggregates of magnetic particles is created in suspension. The ratio between aggregates to mono-dispersed particles (monomers) was measured by using flow cytometer (Accuri C6, BD). The results are showed in FIG. 4(b). For constant total number of particles, it can be seen that the aggregate proportion increases as the Biotin/BSA concentration increase. Based on this curve, the ratio between aggregates and mono-dispersed particles can be obtained for known concentration of SPM particles and Biotin/BSA. For concentration of $3 \times 10^{-9}$, $3 \times 10^{-11}$, $3 \times 10^{-13}$ moldm$^{-3}$, and background (without Biotin/BSA) samples, the percentage of aggregates were measured to be about 62.0%, 42.4%, 24.8%, and 8.4%, respectively.

Example 5: Synthesis of Double Strand DNA (dsDNA) and Functionalization of Magnetic Particles for sdDNA Sensing According to an Exemplary Arrangement of the Present Specification To demonstrate the sensing of DNA by ONLM, double strand DNA have been synthesized and the SPM particles were functionalized with antibodies, which can be specifically bond to dsDNA in order to form magnetic sandwich structures, which can be treated as aggregates and have different NLM transport compared with individual particles, in which no dsDNA have been captured by the particles. Two types of modification of 25-mer DNA probes were used in this exemplary arrangement: one was modified with biotin on 3' and another one had digoxigenin on 5'. Both DNA probes were complementary to different sites of a 75-mer ssDNA. Double-Stranded DNA was prepared by mixing the two probes (1 nmole) and the 75-mer ssDNA (1 nmole) in 100 µL annealing buffer (10 mM Tris-HCl, 1 mM EDTA, 100 mM NaCl, pH 7.5) for 10 min at 85° C. The mixture was then allowed to cool down to room temperature slowly in an isolation box. After hybridization, dsDNA were stored in annealing buffer at 4° C.

Prior to the immobilization of antibody on the streptavidin beads, the particles were washed with PBST and resuspended in PBST buffer. The anti-digoxigenin functionalized SPM were prepared by reacting the biotinylated antibody (30 µg) with the Streptavidin beads (1 mg) in 1 mL PBS buffer for 30 min on a rotating wheel at room temperature. The antibody coated beads were then washed with PBST buffer and incubated with 0.05% biotin in 1 mL PBST buffer for 30 min at room temperature. After washing with PBST buffer, the beads were stored in 1 mL PBST buffer containing 0.1% BSA at 4° C.

Samples of dsDNA were prepared by dilution at the concentration of $10^{-7}$, $10^{-9}$, $10^{-11}$ and $10^{-13}$ mol/L of TPT buffer (5 mM Tris-HCl, 0.5 mM EDTA, 5 mM phosphate buffer, 1 M NaCl, 0.05% Teen 20, pH 7.5). Streptavidin beads were added to the solution containing the target dsDNA, and the mixture was incubated at room temperature on a rotating wheel for 30 min. The dsDNA coated beads were then washed with TPT buffer and reacted with biotin (0.5%) in 1 mL of TPT buffer for half an hour. After washing with TPT buffer, the beads were incubated with anti-digoxigenin functionalized SPM for 30 min on a rotating wheel. The sample containing SPMs was placed next to an NdBFe magnet with a field strength of 2.5 kGauss until the majority of the beads came out of solution. Once the SPMs were collected the tube was rotated 90 degrees in the magnetic field. This allowed the SPM beads to roll over each other on the side of the container.

The process of formation of magnetic sandwich structures (aggregates) in presence of dsDNA and antibodies on functionalized particles is showed in FIG. 4(c). After formation of dsDNA-particles aggregates, the percentage of aggregates was detected by using flow cytometer for different concentrations of dsDNA and results are showed in FIG. 4(d). For concentration of $10^{-7}$, $10^{-9}$, $10^{-11}$, $10^{-13}$, $10^{-15}$ moldm$^{-3}$, and background (without dsDNA) samples, the percentage of aggregates were measured to be about 67.4%, 57.2%, 33.0%, 14.4%, 11.4%, and 7.1%, respectively.

Figure 5:
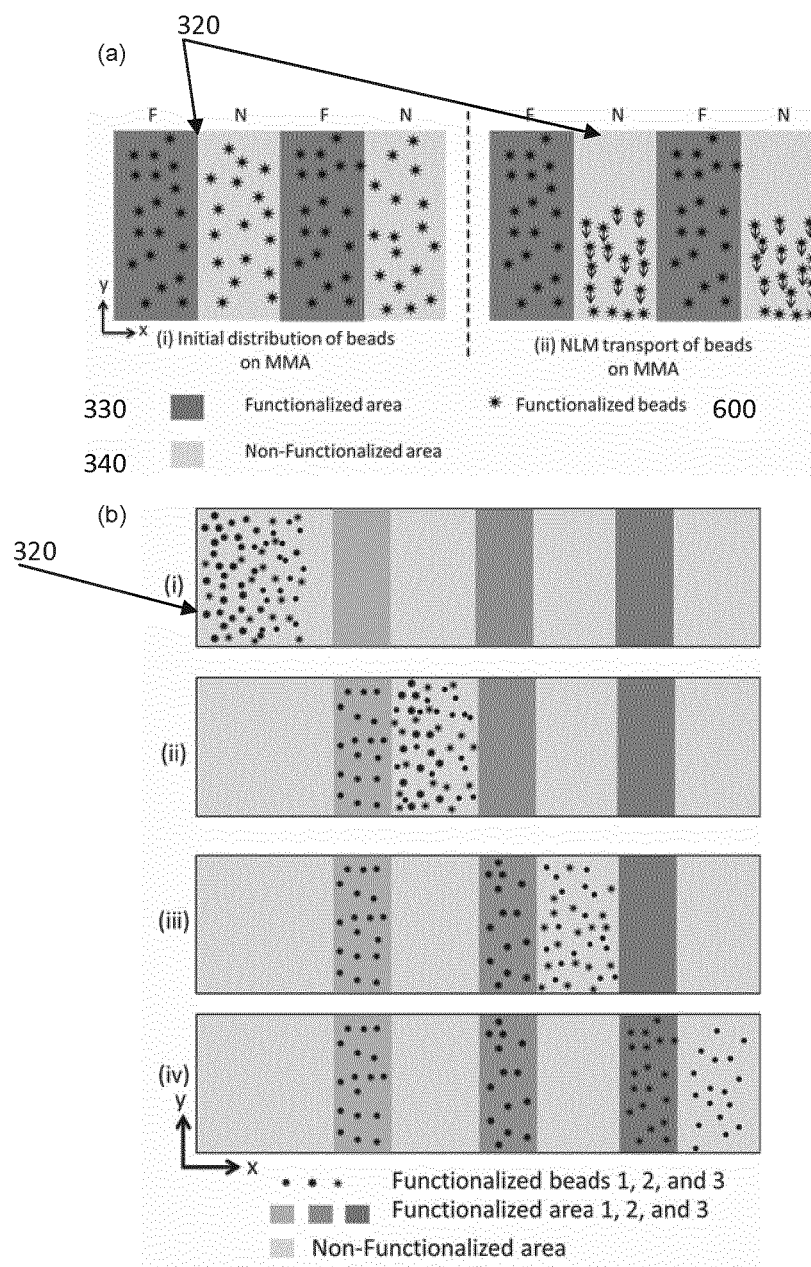
FIG. 5 Sensing of bio-materials by using patterned bio-materials on surface of MMA.

Example 6: Sensing of Bio-Materials by Using Patterned Bio-Materials on MMA Surface Based on ONLM Detection: According to an Exemplary Arrangement of the Present Specification The MMA surface can be coated by bio-materials in pattern and functionalized SPM particles can be specifically bound to the patterned bio-materials. The ONLM can be used on such configuration to perform easy and quick bio-materials detection. The concept of sensing is illustrated in FIG. 5. As shown in FIG. 5(a), a type of bio-material may be patterned on surface of MMA. The pattern process may be made by using methods such as, direct print or writing, soft-print, and self-assembly, etc. This creates a chemical/biological patterned MMA surface, i.e., some areas are coated and functionalized with target bio-materials and other areas are not coated with target bio-materials, but the chemicals may need to functionalize the whole area to reduce the non-specific adhesion to SPM particles. The functionalized areas coated with target bio-materials (as labeled as areas F in the FIG. 5(a)) can specifically bond and immobilize the functionalized SPM particles while the particles are freely movable and can be manipulated in way of NLM transport on non-functionalized, i.e., without target bio-materials (as labeled as area N in the FIG. 5(a)). The different immobility of particles on different areas can induce different ONLM output. By scanning the whole MMA area by ONLM photodetector (by moving chips or detector and optical path) and comparing the signal difference between areas of F and N, the bio-materials on SPM particles can be detected. Alternatively, multiplex detection of bio-materials can also be achieved by using multiple target bio-materials patterned MMA and multiple functionalized SPM particles. FIG. 5(b) shows a concept to detect multiplex bio-materials by using multiple patterned bio-materials on MMA surface with using similar principle. As shown in FIG. 5(b), multiple bio-functionalized particles travel across the whole MMA surface, which is pattered with different bio-materials. The specific bond between corresponding particles and bio-materials coatings allow the particles being immobilized on specific patterned areas while the other particles can still move across the areas. By scanning the whole area by ONLM and comparing the signal difference at each moment in rotating magnetic field, the multiplex detection can be quickly achieved.

Example 7: Surface Chemistry: According to an Exemplary Arrangement of the Present Specification To minimize the surface adhesion, the SPM particles and MMA surface are coated with non-sticky chemical coatings. For demonstration purpose, 0.1% w/v Casein (Adrich sigma) in PBS was used to coat a thin layer of Casein on MMA and the same Casein solution was used for SPM particle.

Examples

Some examples to demonstrate the applications of ONLM and on-chip particle focusing are presented herein below, according to exemplary arrangements of the present specification. It is noted that the biological species are not limited to Biotin/BSA or double strand DNA. Any biological species which can be functionalized on SPM particles and serve as the linkers to form aggregates or change the mobility or immobility properties of SPM particles can be used for the purposes of biological sensing.

Figure 7:
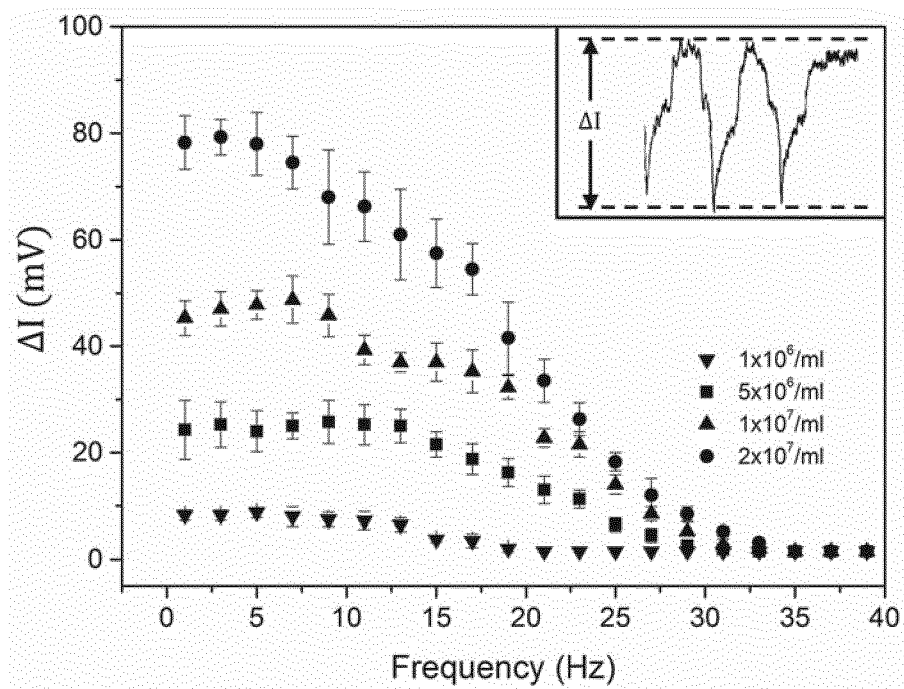
FIG. 7 shows signal Vpp output signal of ONLM vs. rotation frequency of external rotating magnetic field for certain concentration of 2.8 μm SPM particles. Because the immobility of SPM particles on surface of NLM/FNLM chip decrease as rotation frequency increases as the rotation frequency higher than particles critical frequency. Furthermore, the fraction of immobilized particles increases as the rotation frequency increases. It can be seen clearly from the figure that the output signals decrease from low frequency to high frequency until they reach to the minimum at which all SPM particles are immobilized when the frequency is higher than their immobilization frequency.

Demonstration of Detection of SPM Particles by ONLM, According to an Exemplary Arrangement of the Present Specification To demonstrate the performance of ONLM, the 2.8 µm dynabeads M270 (Streptavidin) were used in NLM separator. 200 µl of SPM particles in PBST ($10^7$/ml in concentration) were dispensed on MMA surface and 0.17 mm thick microscopic coverslip was used on top of sample suspension. One of electromagnets, the bottom electromagnet, which create rotating magnetic field around the NLM separator, was turned on to trap the SPM particles on MMA surface. After that, the rotating magnetic field was applied to drive the SPM particles on MMA. During the NLM transport of SPM particles, the ONLM was recording the signal output from photodetector in real time and the data processing was carried out after experiment. In the post analysis, the peak-to-peak voltage, $V_{pp}$, (as shown in inset in FIG. 7) of photodetector output was measured and analyzed. The time response of $V_{pp}$ was also analyzed to get frequency response of output. The time responses of output reflect the moving speed and mobility of SPM particles and it also can be easily converted to the response to rotation frequency of rotating magnetic field.

1. ONLM for Particles Countering, According to an Exemplary Arrangement of the Present Specification The quantity of SPM particles on an MMA vs. $V_{pp}$ of photodetector on ONLM was measured. The number of SPM particles was manually countered by using microscope before recording of $V_{pp}$ signal. Then the SPM particles were driven by rotating magnetic field at 1.0 Hz rotation frequency. At this low frequency, 100% of SPM particles were movable on MMA with speed of 8 μm/s. The result of $V_{pp}$, vs. the number of moving SPM particles on MMA was presented in FIG. 6. It can be clearly seen from FIG. 6 that the ONLM output is linearly proportional to the numbers of moving SPM particles on MMA. The relationship between number of particles, N, to output signal, $V_{pp}$ (mV), can be found in fitting curve, V=5.136+0.227N. Thus, the $V_{pp}$ signal is about 5.3 mV with only one single particle on MMA based on above relationship. The background noise, which is defined as the fluctuation of baseline of output signal ($V_{pp}$) of ONLM for NLM chip without any particle, is measured as about 3 mV. Therefore, the ONLM can potentially detect one single particle's movement on NLM chip. Similarly, with known type of particles and output signal of ONLM, the number of particles on MMA can also be countered by calibrated ONLM with known signal-number curves.

2. ONLM Response to Rotation Frequency of External Rotating Magnetic Field, According to an Exemplary Arrangement of the Present Specification is Described with Reference to FIG. 7 which shows changes of output signal, $V_{pp}$, of ONLM vs. rotation frequency of external rotating magnetic field for certain concentration of 2.8 μm SPM particles. The immobility of the SPM particles on surface of NLM/FNLM separator decreases as rotation frequency increases, as the rotation frequency higher than particles critical frequency. Furthermore, the fraction of immobilized particles increases as the rotation frequency increases. It can be seen clearly from the figure that the output signals $V_{pp}$ decrease from low frequency to high frequency until they reach to the minimum at which all SPM particles are immobilized when the frequency is higher than immobilization frequency of particles. Based on this fact and response curve, detection of different magnetic objects based on their difference of magnetic mobility can be easily carried out by ONLM.

3. Detection of Two Types of SPM Particle, According to an Exemplary Arrangement of the Present Specification Mixture of 2.8 μm and 1.0 μm SPM particles were investigated by using ONLM to discriminate those two particles in NLM separator.

Figure 8:
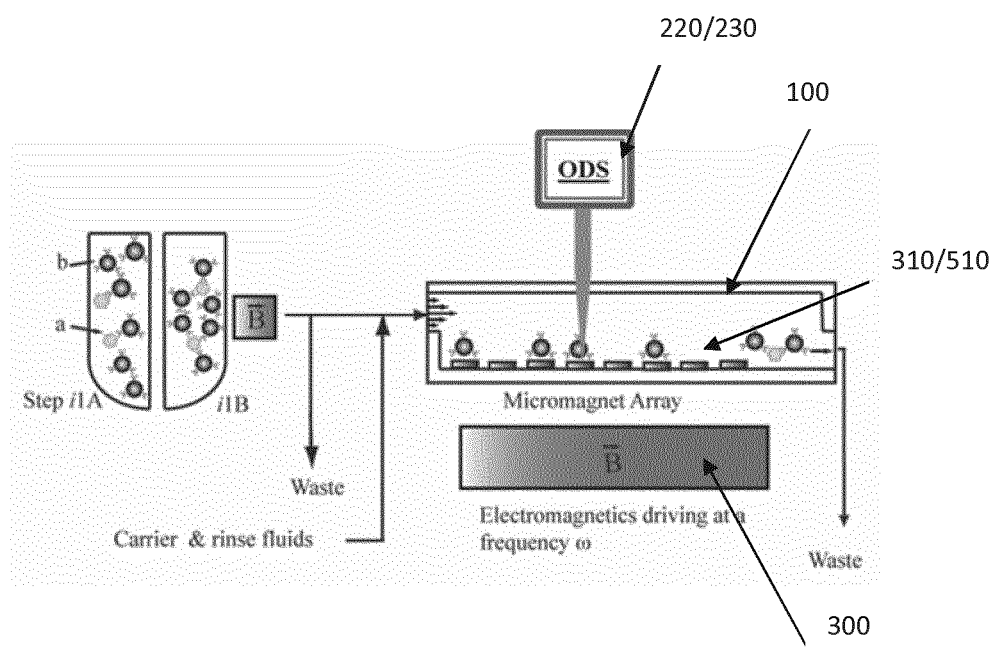
FIG. 8 shows a schematic view of micro-particle aggregates introduced into separator which have been detected by ONLM and separated by FNLM separator simultaneously according to an exemplary arrangement of the present specification.

4. Analysis of aggregates formed by Biotin/BSA in SPM particles sample according to an exemplary arrangement of the present specification The aggregates of 2.8 μm SPM particles were prepared by using different concentration of Biotin/BSA in PBST. In presence of Biotin/BSA in streptavidin particles, certain percentage of aggregates formed with Biotin/BSA as inter-particles linkers between SPM particles. As described previously, for concentration of $10^{-9}$, $10^{-11}$, and $10^{-13}$ moldm$^{-3}$ of Biotin/BSA, the percentage of aggregates were measured to be about 62.0%, 42.4%, 24.8%, and 8.4%, respectively The sample of aggregates with different concentration of Biotin/BSA were separated and detected by using NLM separator and ONLM. Referring to FIG. 8 a schematic view of the concept is shown, e.g., how SPM particle aggregates are introduced into separator then have been detected by ONLM and separated by FNLM separator simultaneously.

5. NLM Transport of Single Magnetic Particle and Magnetic Aggregates According to an Exemplary Arrangement of the Present Specification.

Figure 9:
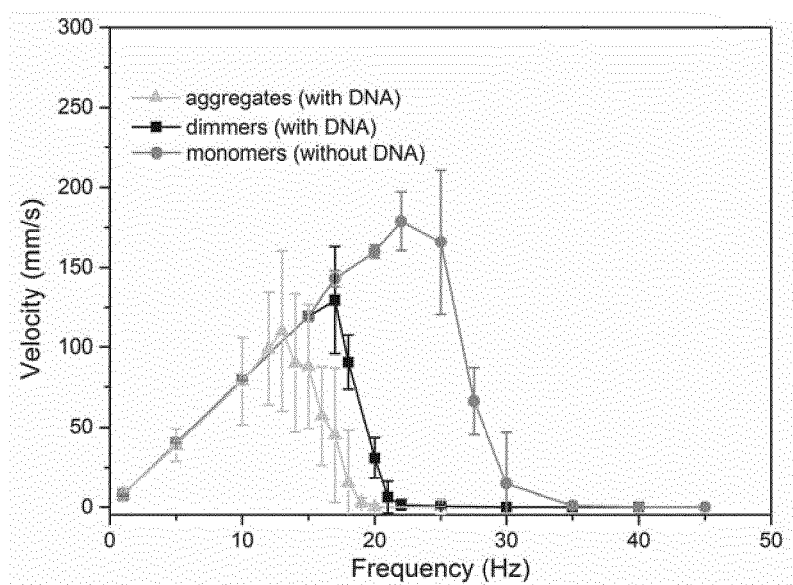
FIG. 9 NLM transport of single SPM particles and magnetic aggregates, which created by adding the biotin/BSA in the solution of same magnetic particles is illustrated. Compared with single particles, the magnetic aggregates have lower critical frequency and immobilization frequency. Accordingly the aggregates are shown to have been immobilized at relative lower rotation frequency compared with single particles.

NLM transport of single SPM particles and magnetic aggregates, which were created by adding the Biotin/BSA in the solution of same magnetic particles, is described with reference to FIG. 9. The average speed of particles on MMA in rotating field was measured and the results shown in FIG. 9. Compared with single particles, the magnetic aggregates have lower critical frequency and immobilization frequency making them more prone to be immobilized at relative lower rotation frequency compared with single particles.

Figure 6:
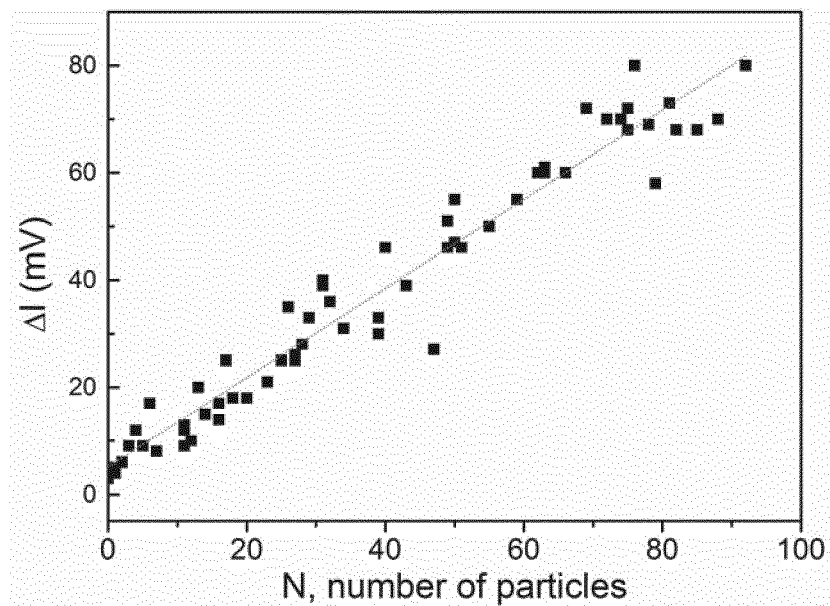
FIG. 6 shows Numbers of 2.8 μm SPM particles vs. Vpp signal outputs of ONLM as the particles travel in 1 Hz rotation frequency in NLM chip. The typical ONLM output has the shape as shown in inset. The inset shows the definition of Vpp signal. It can be clearly seen from FIG. 6 that the ONLM outputs is linearly proportional to the numbers of moving SPM particles on NLM chip. The background noise, which is defined as the fluctuation of baseline of output signal of ONLM for NLM chip without any particle, is measured as approximate 3 mV. Therefore, the ONLM can potentially detect one single particle's movement on NLM chip. Similarly, numbers of particles on NLM/FNLM chip can also be countered by calibrated ONLM with known signal-number curves.

Referring to FIG. 6 it has been noted that as the number of immobilized particles increased in high concentration of Biotin/BSA samples, the output signal $V_{pp}$ of the samples decrease in the full range of rotation frequency. Correspondingly, with calibrated curve, the output signal can be converted to the concentration of Biotin/BSA in suspension.

6. Sensing of Biological Materials According to an Exemplary Arrangement of the Present Specification a. Detection of Biotin/BSA Based on above described method according to the present specification, the different concentrations of Biotin/BSA were detected in the form of different ratios of magnetic aggregates on an MMA. Three concentrations of Biotin/BSA, $10^{-9}$, $10^{-11}$, and $10^{-13}$ moldm$^{-3}$, were used to form aggregates suspensions with different percentage of aggregates. The frequency response of ONLM signal was measured for those three types of samples as shown in FIG. 10(*a*). It can be clearly seen that with same concentration and volume of magnetic particles, the measured output signal from ONLM are different for different concentration of Biotin/BSA in a full range of rotation frequency. The samples with relative low concentration of Biotin/BSA have relative higher output at same rotation frequency, due to high percentage of movable aggregates. Moreover, the output signal for sample with high percentage of aggregates, i.e. high concentration of Biotin/BSA are more quickly decreased as the rotation frequency increased. This reflects the fact of that the sample with high ratio of aggregates are easier to be immobilized compared with lower ratio of aggregates samples. We compared the maximum outputs of $V_{pp}$ for all samples. The results were showed in FIG. 10(*b*). It can be seen from FIG. 10(*b*) that the higher concentrations of Biotin/BSA produce relative lower output signals than that of samples with lower concentrations of Biotin/BSA. It also shows that even at the concentration of Biotin/BSA as lower as $10^{-13}$ moldm$^{-3}$, there is still detectable difference of signal between aggregates sample and the sample without any Biotin/BSA. It proves that ONLM is capable of detect the difference of Biotin/BSA in term of different aggregates percentages in the magnetic particles. The signal outputs for different samples are almost linearly distributed. More specifically, at a concentration of Biotin/BSA is $10^{-13}$ moldm$^{-3}$, the output signal is 24.0 mV, which is 4.5 mV less than the signal from sample without any Biotin/BSA (32.7 mV). That value is much higher than detectable noise (3 mV) of ONLM with current settings. It implies that the ONLM is potentially can be used detect the concentration of Biotin/BSA lower than $10^{-13}$ moldm$^{-3}$. It also can be expected that with higher ratio of Biotin/BSA to magnetic particles in mixture and improved detectors, even trace of bio-analytes can be detected with relative high resolution.

b. Sensing of Double Strand DNA (dsDNA)

To demonstrate the sensing of dsDNA, different concentrations of dsDNA were bound on the SPM particles to form different percentages of sandwich structures (aggregates) as described above. The percentage of aggregates in sample suspension is highly associated with the concentration of dsDNA on the particles, as described before. As the percentage of aggregates increasing, the mobility of whole particle group on the MMA vs. the rotation frequency of rotating magnetic field decrease. Thus the output signal of ONLM decreases correspondingly. In this example, the concentrations of dsDNA from 0 to $10^{-7}$ moldm$^{-3}$ were tested in order to verify to sensitivity of ONLM for dsDNA sensing. The frequency response of ONLM signal was measured for the samples with different concentration of dsDNA are described with reference to FIG. 11(*a*). It can be clearly seen that the measured output signal of ONLM are different for different concentration of dsDNA in a full range of rotation frequency. The samples with relative low concentrations of dsDNA have relative higher output at same rotation frequency. It also can be seen that the output signal for sample with high percentage of aggregates, i.e. high concentration of dsDNA are more quickly decreased as the rotation frequency increased. As described similarly with the cases for Biotin/BSA, the fact is that sample with high percentage of aggregates are easier to be immobilized compared with that of lower percentage of aggregates. We compared the maximum outputs of all samples in order to see quantitatively the sensitivity of the detection; the results are described with reference to FIG. 11(*b*). Referring to FIG. 11(*b*) it is noted that the ONLM system of the present specification may be used to detect the difference of dsDNA in terms of different aggregates percentages in the magnetic particles. The signal outputs for different samples are largely linearly distributed. At concentration of dsDNA is $10^{-13}$ moldm$^{-3}$, the output signal is 26.7 mV, which is 4.6 mV less than the signal from sample without any dsDNA (31.3 mV). That value is higher than detectable noise (3 mV) of ONLM with current settings. It implies that the ONLM is potentially can be used detect the concentration of dsDNA lower than $10^{-13}$ moldm$^{-3}$. It also can imagine that with more precise biological functionalized technology and electronic readout, the background noise and measured signal can be further improved. That allows even more sensitive sensing of biological materials by using ONLM.

Demonstration of On-Chip Focusing of SPM Particles Using the Focusing MMA

Figure 12:
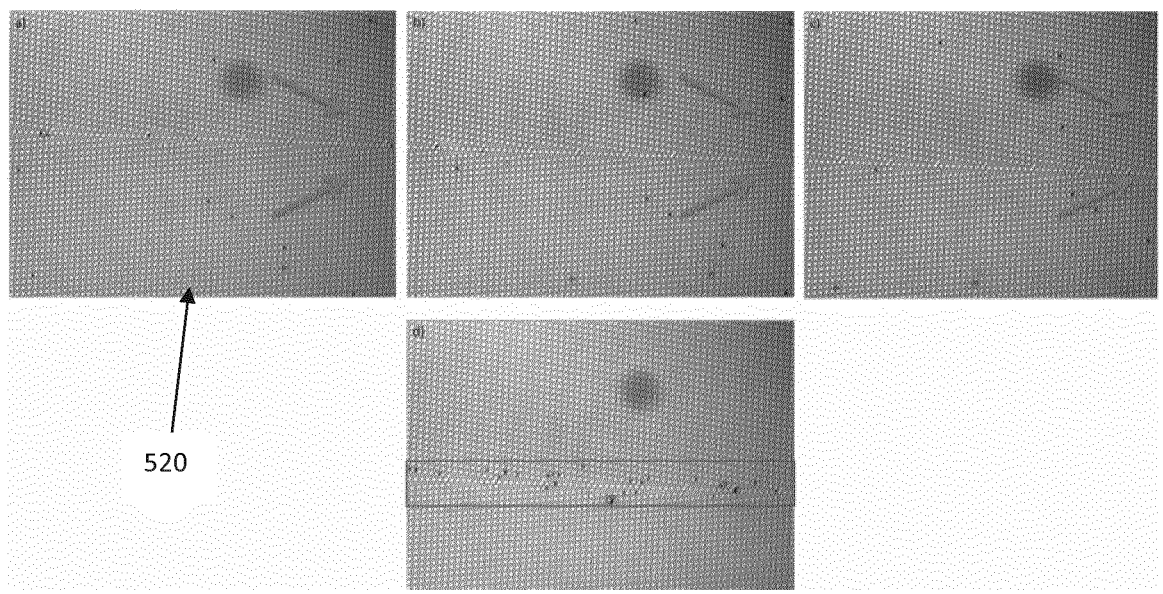
FIG. 12: The demonstration of the on-chip particle focusing using the focusing MMA. The particles travelling along an array of micro-magnets converge in the central line of the chip (FIGS. 12 a, b, and c) until they are all confined in the central region. Once the beads have entered the central region of the MMA they continue travelling along the chip and remaining in this region until the end of the magnets array.

Example 1: Focusing of 2.8 µm SPM Particles on the Focusing MMA According to an Exemplary Arrangement of the Present Specification To demonstrate on-chip focusing capability, 2.8 µm SPM particles were focused by using the focusing MMA (with design in FIG. 3(*c*)). The external magnetic field and the MMA were prepared with methods described earlier. 10 µl of 2.8 µm SPM particles suspension was dispensed on the left hand-side of the focusing MMA. The external magnetic field was switched on to hold the particles, and a glass coverslip was placed on top of the chip to uniformly distribute the PBS solution and to enable microscopic observation. Subsequently, the rotating magnetic field was applied and the beads were observed to move along the chip and converge in the central region of the magnets array. Referring to FIG. 12 screenshots acquired during the focusing process according to a method of the present specification are described. In FIGS. 12 (*a*)-(*c*), it is shown that particles move along micro-magnets lines with the angular orientation and eventually reach the central line of the magnets array at different horizontal positions depending on their starting point. When the particles reach the central region of the array they continue travelling along the central line until the end of the MMA (FIG. 12 (*d*)). This way, particles can be focused at rotation frequencies up to 13 Hz, which is much lower than their critical frequencies, without stalling.

Example 2: Focusing of 2.8 µm SPM Particles on the Tree-Like Hierarchy Structure Focusing MMA According to an Exemplary Arrangement of the Present Specification are Described with Reference to FIG. 13

Figure 13:
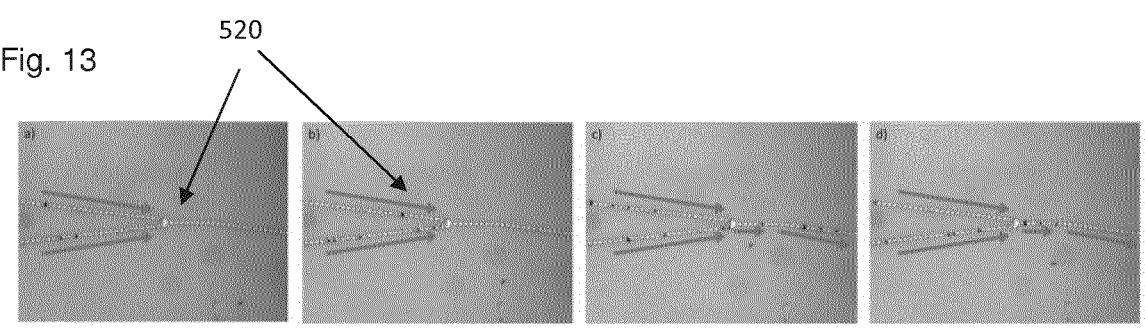
FIG. 13: The demonstration of the on-chip particle focusing using the focusing MMA with hierarchical structure. Incoming particles travel along the angularly aligned lines of micro-magnets towards the junction (FIGS. 13a and b). After passing the junction, the particles continue moving along the next line towards the next junction (FIGS. 13c and d). This process is repeated across the whole MMA until all the particles are focused in the line of magnets at the center of the focusing MMA.

A similar characterization was performed for the focusing MMA with the tree-like hierarchical structure. Starting from the dispensing region, the particles travelled along the sixteen angularly aligned micro-magnets lines towards the focusing junctions, as shown in FIG. 13 (*a*)-(*b*). The particles coming from two different converging lines reached the junction and continued travelling along the same path towards the next junction as shown in FIG. 13 (*c*)-(*d*). Thus, particles coming from different regions on the chip were focused and traveled along the same trajectories until they reached the end of the array.

Figure 14:
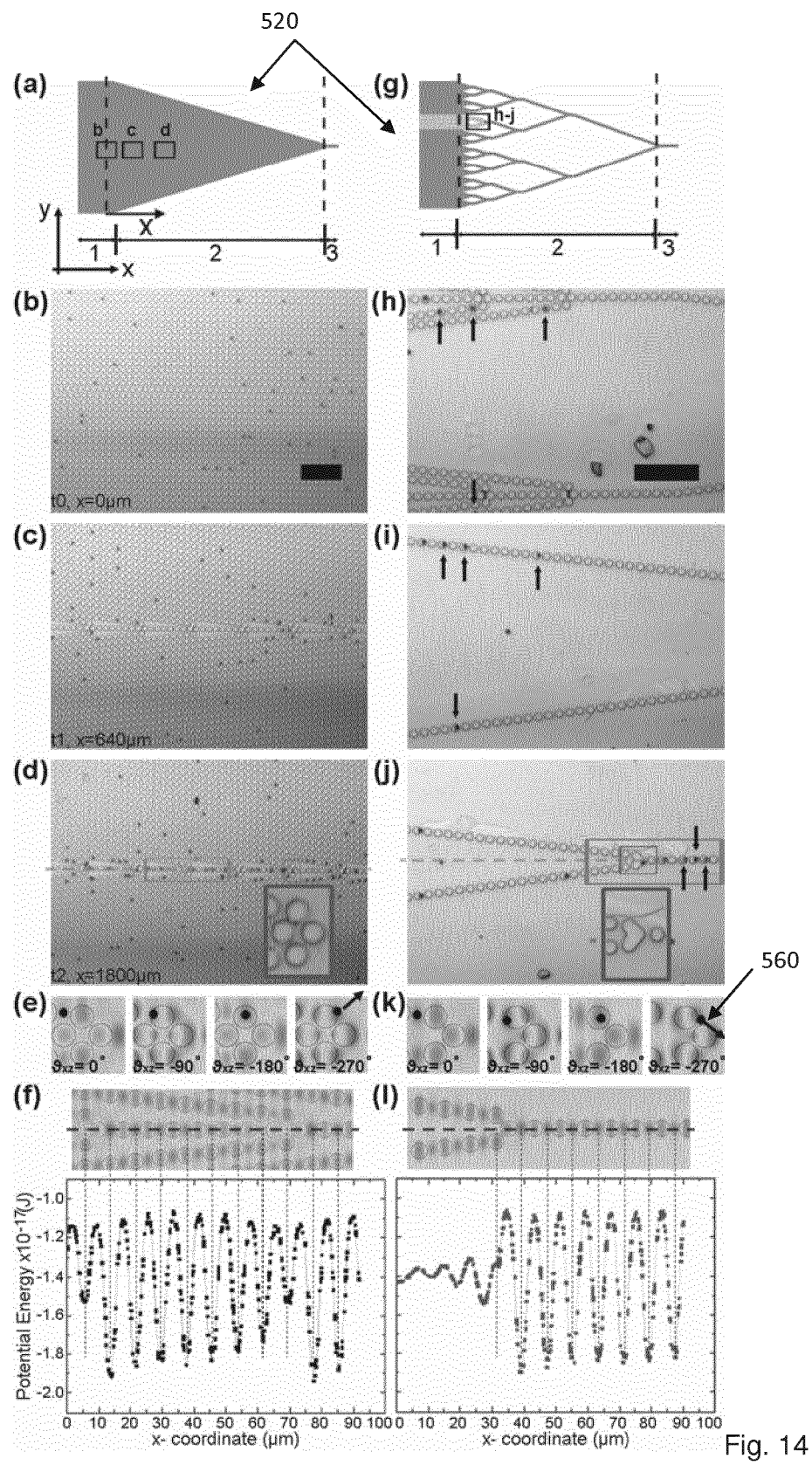
FIG. 14 Focusing MMA designs.
Figure 15:
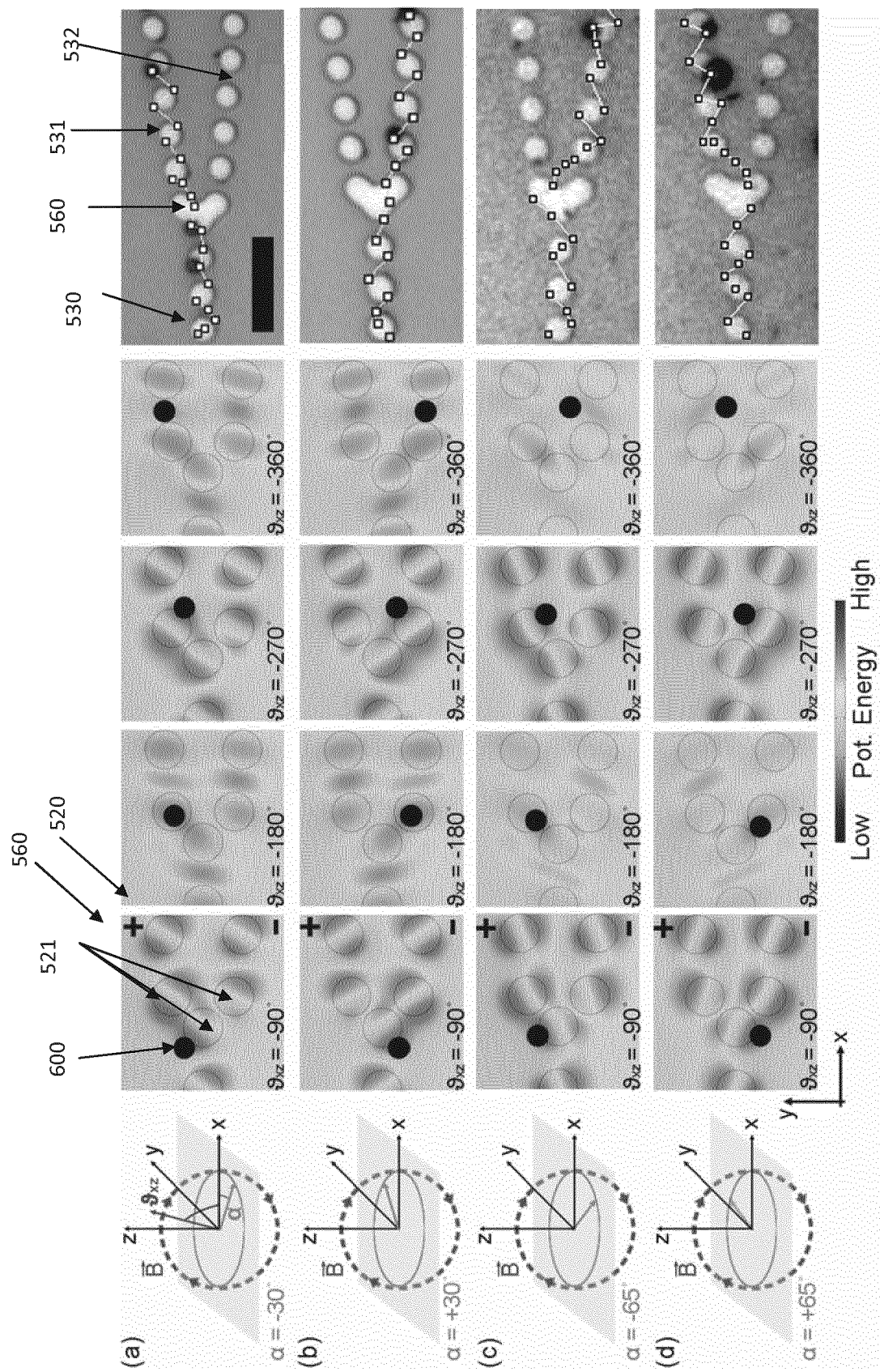
FIG. 15 shows Magnetic switching junctions according to an arrangement of the present specification—Schematics (left column) identify the orientation of magnetisation of the micromagnets, α, and the sense of rotation of the applied field, $\vartheta xz$. The finite element calculations were performed by imposing a micromagnet magnetisation of 80 kA/m and an external field with flux density of 30 G. The black circles represent the predicted positions of the beads for given $\vartheta xz$. Microscopic images (right column) were used to identify the motion of the beads over the array and their trajectories were illustrated using white dots (representing specific $\vartheta xz$) connected with yellow lines.
Figure 16:
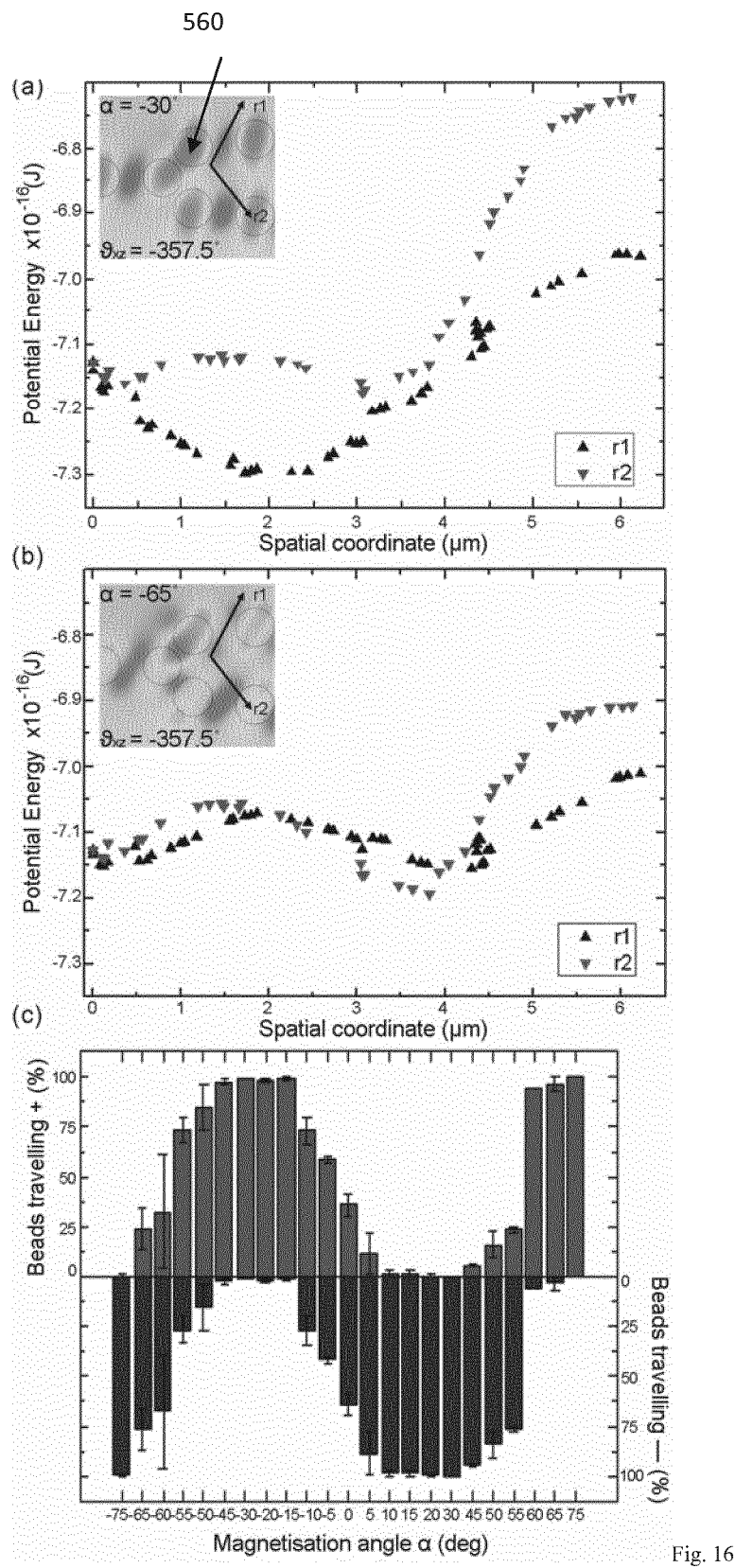
FIG. 16 show graphs relating to analysis of the switching behaviour of the tri-magnetic junction as a function of the orientation of magnetisation.
Figure 17:
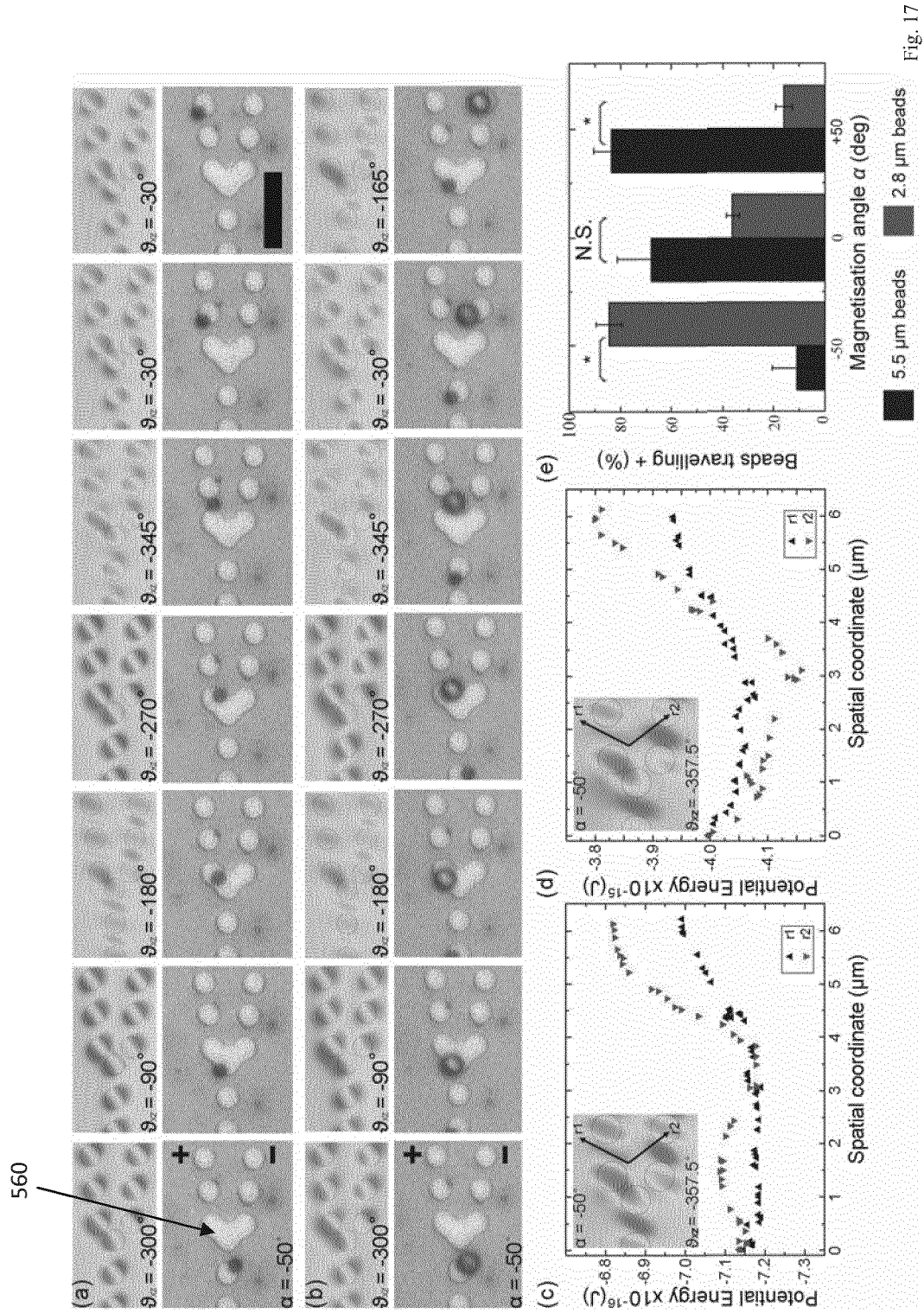
FIG. 17 SPM bead separation on a tri-magnet junction for a magnetisation angle α=−50°.

Reference is made to FIGS. 14 to 18 Micromagnet arrays 520 for on-chip focusing, switching, and separation of superparamagnetic beads and single cells are described. Two micromagnet array (MMA) arrangements that allow superparamagnetic (SPM) beads to be focused, sorted, and separated on-chip are described together with details of applications. Converging MMAs 520 according to an exemplary arrangement of the specification were used to rapidly collect the SPM beads from a large region of the chip and focus them into synchronized or single lines. The collection efficiency of the devices there application for on-chip analysis of populations of SPM beads P using a single-point optical detector is described. Referring to FIGS. 15-17 diverging MMAs 720 configured to control the transport of the beads and to separate them based on their size are described. The separation efficiency is controllable by configuration and control of the orientation of the magnetisation of the micromagnets relative to the external magnetic field and the size of the beads relative to that of micromagnets. By controlling these parameters and the rotation of the external magnetic field controlled transport of SPM bead-labelled single MDA-MB-231 cells was provided in an exemplary arrangement. The converging and diverging MMAs according to arrangements of the present specification allow magnetically-labelled cells to be efficiently isolated and then manipulated on-chip for analysis with high-resolution chemical and physical techniques.

Referring to FIGS. 14*a* and *g* two schematics that show two exemplary converging micromagnet array arrangements according to the present specification are described. Each of these MMAs 520 is comprised of three regions: Region 1 is configured, and in operation is used, to capture beads of a sample and comprises an MMA of rectilinear form. The MMA is comprised of 5 µm-diameter circular magnets with 8 µm centre-to-centre distance; Region 2 is configured, and in operation is used, to focus the beads of a sample. Region 2 is a focusing region and comprises lines 530 of magnets 521 arranged at an angle of substantially ±7° with respect to the x-axis (in the exemplary arrangement). The lines 530 converge into a single line 550 of micromagnets. The MMA further comprises a third sensing region—region 3. The sensing region 550 is comprised of a single or line row of magnets 531 and ideally is the location where an optical sensor would be placed. In the exemplary arrangement of FIG. 14*a*, region 2 is comprised of densely packed lines of magnets (FIG. 14*a*); whereas in the exemplary arrangement of FIG. 14*g*, region 2 is comprised of a tree-like structure in which the focusing process takes place in consecutive steps (FIG. 14*g*).

Referring to the Figures the properties of the two converging micro magnet array arrangements of FIGS. 14*a* and 14 *g* are described. The properties include focusing efficiencies, critical frequencies, and bead focusing velocities. The transport of the beads was monitored via optical microscopy (FIGS. 14*b-d* and 14*g-j*). Properties of the arrangement of FIG. 14*a* were measured by dispensing the beads on Region 1 and then following their motion through the MMA having placed the chip on a motorized stage translating at the same velocity of the beads. The beads first travelled across the rectilinear MMA in Region 1 until they met the converging lines of micromagnets in Region 2 (FIG. 14*b-c*). Once the SPM beads reached the central line of micromagnets they remained confined in that row (FIG. 14*d*) until they entered Region 3. Due to the geometry of the MMA, the beads reached the central region at different x-coordinates depending on their starting position, so that the percentage of focused beads increased with the distance from the beginning of Region 2, as it is clear from FIG. 14*b-d*. A similar behavior was observed for the arrangement of FIG. 14*g* with the SPM beads rapidly moving through Region 1 to be focused in Region 2 (FIG. 14*g-j*). Bead focusing efficiency was quantified by the ratio of beads passing through a particular focusing junction to the total number of beads dispensed on the left hand-side of the junction (light grey area in FIG. 14*f*), averaged over two different junctions (around 600 beads).

In the arrangement of FIGS. 14*a* and 14*g* in the exemplary method the percentage of beads recovered was 94.3±2.9 and 89.4±2.9%, respectively. The critical frequency of the beads was evaluated on each region of the converging array designs and was found to be indistinguishable, i.e., $\Omega_c$ was measured to be 20-22 Hz on both the arrangements of FIGS. 14*a* and 14*g* showing that the local magnetic field produced by a line and array of micromagnets is similar. This was confirmed by 3-D finite element modelling as presented in FIGS. 14*e* and 14*j*, that show the simulated magnetic field along the central line of magnets in design A and along the centre of a focusing junction in the arrangement of FIG. 14*g* (green dotted lines in FIGS. 14*d* and 14*i*). The field in correspondence of the connection between the tilted lines and the central straight line of magnets (FIG. 14*a*) is comparable to the field in correspondence of a focusing junction (FIG. 14*g*). In the arrangement of FIG. 14*a* the field presents a maximum in correspondence of the connection and then decreases from one connection to the next one (separated by 8 magnets, that is 64 μm) due to the increasing influence of the magnets along the tilted lines. This effect is not present on arrangement of FIG. 14*a* and the field remains constant after the junction. The measured critical frequency corresponded to a maximum bead velocity around 180 μm/s in Region 1 and along the tilted lines of magnets in both designs. However the speed of the focusing process was limited by the maximum velocity at which the beads were able to jump on the central row of magnets (arrangement of FIG. 14*a*) or to cross a focusing junction (arrangement of FIG. 14*g*), that was 88-96 μm/s for arrangement of FIG. 14*a* and slightly lower for arrangement of FIG. 14*g*.

Insight into the focusing process in the diamond and tri-magnet configurations was gained from finite element simulations of the potential energy distributions on these geometries as a function of $\vartheta_{xz}$, as presented in FIGS. 14*e* and *k*. The spatial arrangement of the diamond shaped micromagnets, presented in FIG. 14*e*, created an energy distribution that forced the beads towards the next line of tilted micromagnets at $\vartheta_{xz}$<270° (arrow points at the direction that the potential energy minimum moves as the external magnetic field is rotated). In contrast, at the tri-magnet junction the beads move across the micromagnets without encountering an energy barrier (FIG. 14*k*).

The converging MMA designs were further characterised by measuring the critical frequencies and velocities of uniform SPM beads. The critical frequency, $\omega_c$, was measured for all regions of the MMA designs and was found to be 20-22 Hz except for the diamond-shaped junction in design A and the tri-magnet junction in design B. This indicated that the local potential energy landscape produced by a single line of micromagnets was similar to that produced by a rectilinear continuous array of micromagnets. This observation was confirmed by the 3-D finite element simulations of the potential energy along the central line of magnets in design A and at the focusing junction in design B (green dotted lines in FIGS. 14*d* and 14*j*, respectively). The potential energy minima for design A (FIG. 14*f*) and design B (FIG. 14*l*) were similar in magnitude. Along the central line of design A, the potential energy minima with the lowest magnitude occurred where the tilted lines met the central line. The potential energy minima adjacent to this (in the +x-direction) had the highest magnitude, where the magnitudes of the subsequent minima decreased with increasing x with a periodicity of eight micromagnets (FIG. 14*f*). In design B, this effect was also present at the end of region 1 (FIG. 14*h*), but not when the micromagnets converged at the tri-magnet junction (FIG. 14*j*). In both design A and B, the measured $\omega_c$ corresponded to a maximum bead velocity of ca. 180 μm/s in region 1 and along the tilted lines of magnets. However, the speed of the overall focusing process was limited by the maximum velocity at which the beads were able to reach the central line (design A) or to cross a focusing junction (design B). The bead velocity at a diamond-shaped junction in design A was 88-96 μm/s and slightly lower at a tri-magnet junction in design B.

Magnetic Switch

In a reverse or opposite arrangement to that of FIG. 14 an MMA having a diverging configuration is described with reference to FIG. 15, in which a single line 730 of micromagnets if arranged to diverge into two lines 732 and 733 at a tri-magnet junction 750 (FIGS. 15*a* and 15*b*). When the applied field is rotating clockwise in the xz-plane, the beads travel along the single line 730 of micro-magnets in the positive x-direction.

FIG. 15 shows the motion of the SPM beads through a switching junction, where a single line of micromagnets diverges into two lines of micromagnets at the tri-magnet structure. The schematics on the left-hand side of FIG. 15 show the orientation of the micromagnet magnetisation in the xy-plane (α), as well as the orientation of the rotation of the external magnetic field ($\vartheta_{xz}$). When the magnetisation of the micromagnets was aligned with the x-axis, it was observed that the beads randomly selected one of the two diverging lines of micromagnets (data not shown), which we designate as + or − according to the angle they make with the x-axis. However, when the micromagnets were magnetised at an angle α with the x-axis, a preferential switching direction was imposed to the beads. FIGS. 15a, b, c, and d present four specific cases where α=−30°, 30°, −65°, and 65°, respectively. Tuning the orientation of the magnetisation of the micromagnets induced a preferential switching behaviour of the beads at the tri-magnet junctions. To gain insight into this behaviour, finite element calculations were performed on the switching junction for the different values of α. FIG. 15 presents the bead trajectories and potential energy landscapes for different α angles and $\vartheta_{xz}$, with the darkest regions in simulations corresponding to the potential energy minima. Black circles of the size of the SPM beads have been placed in the area of minimum potential energy for each α and $\vartheta_{xz}$. For α<0, the beads jumped from the bottom of one micromagnet to the top of the adjacent one as the external field was rotated (i.e., as $\vartheta_{xz}$ decreased). Accordingly, the beads moved across the top of the tri-magnet junction, and for small magnitudes of α, e.g., α=−30°, they had a tendency to select the +line of micromagnets, as presented in FIG. 15a. Note that bead trajectories are superimposed on the microscopic images (last column) to demonstrate this transport process. An opposite switching behaviour was observed when the magnetisation of the micromagnets was positively tilted, e.g., α=+30°, where the beads selected the −direction after crossing the junction (FIG. 15b). This switching behaviour was modified for higher magnitudes of α, i.e., the beads moved onto the −line of micromagnets for α=−65° (FIG. 2c) and onto the +line of micromagnets for α=+65° (FIG. 15d). This behaviour was interpreted as the result of the formation of an asymmetric potential energy distribution on the MMA at $\vartheta_{xz}$=−360°.

In correspondence of the junction the beads will randomly select one of the two possible paths (designated as + or − depending on the angle with the x-axis of the chip) if the orientation of the magnetization of the micromagnets is parallel to the x-direction. However, if the orientation of the magnetization of the micromagnets is tilted by an angle α in the xy-plane, a preferential direction in the motion of the beads is induced. When the magnetization is tilted by a negative α angle the trajectory of the beads rotates accordingly, and they translate across the chip jumping from the bottom of one magnet to the top of the adjacent one, as shown in FIG. 15a for α=−30°. Thus, the beads approach the tri-magnet junction from the top and continue travelling along the +direction. An opposite behaviour is observed when the magnetization of the micromagnets is tilted by a positive α angle, with the beads jumping from the top of one magnet to the bottom of the adjacent one, as shown in FIG. 15b for α=+30°, and remaining confined in the −direction after the junction. Therefore, by tuning the orientation of the magnetization of the micromagnets it is possible to switch the behavior of the beads in correspondence of the junction. The graph in FIG. 15c shows the percentage of beads travelling along the +direction for different α angles, averaged over 10 different junctions on 2 chips, with 20 beads analyzed per junction. This characterization was performed with commercially available 2.8 μm beads. As it is possible to see from the graph, the efficiency of the switch increases with α up to ±45°, with almost all the beads travelling along the − and +direction, respectively. Above ±45° the beads started inverting their behavior jumping along the opposite path after crossing the junction. The behavior was completely inverted above ±60°. This phenomenon was attributed to two factors: the increased diversion in the trajectory of the beads and the reduced energy barrier between the magnetic field maxima along the two directions.

FIGS. 16a and b present finite element calculations of the magnetic potential energy for a 2.8 μm diameter bead with χ=0.17, evaluated at the tri-magnet junction along the two possible trajectories, i.e., $\vec{r}_1(+)$ and $\vec{r}_2(-)$, for α=−30° and −65°, respectively. The potential energy was evaluated at $\vartheta_{xz}$=−357.5°, which was the approximate angle at which the beads were observed to choose one of the two possible trajectories. For α=−30° (FIG. 16a) the beads saw a lower potential energy profile along the $\vec{r}_1$ direction compared to the $\vec{r}_2$ direction. Thus, the force attracting the beads in the $\vec{r}_1$ direction ($-\partial U_m/\partial \vec{r}_1$) was higher than the force attracting the beads in the $\vec{r}_2$ direction ($-\partial U_m/\partial \vec{r}_2$). Thus, in this case the beads travelled along the $\vec{r}_1$ direction and continued along the +path. For α=−65° (FIG. 16b), the beads saw a deeper and closer potential energy minimum in the direction relative to the $\vec{r}_1$ direction. Accordingly, the beads travelled along the $\vec{r}_2$ direction, provided that they could overcome the short-range energy barrier that is formed along this trajectory. It was observed that this energy barrier imparted a frequency dependent switching behaviour to the switching process, i.e., beads moving at low speed (external driving frequency ω<1 Hz) travelled along $\vec{r}_1$, whereas beads moving at high speed (ω≥1 Hz) travelled along $\vec{r}_2$. Similar behaviour was observed for positive values of α.

FIG. 16c presents the percentage of beads travelling along the two micromagnet paths as a function of a, based on data collected over 10 different junctions on two separate chips, with at least 20 beads analysed per junction. The external driving frequency was 1 Hz, corresponding to a bead's velocity of 8 μm/s. The switching efficiency (defined as the percentage of beads selecting the expected path) for the +path increased for decreasing negative values of α, and was effectively 100% for −45°<α<−15°. Conversely, the percentage of beads taking +path decreased for increasing positive values of α, with minimum values obtained for 15°<α<45°. Further increasing |α| resulted in the inversion of the turning behaviour, such that the beads started to move to the opposite path after crossing the junction. Thus, for −65°<α<−45° the switching efficiency decreased with an increasing fraction of beads moving onto the −direction. The opposite behaviour was observed for 45°<α<60°, with an increasing fraction of beads moving onto the +direction. The switching efficiency increased for even higher |α|, i.e., for α<−65°, the percentage of beads taking the −path was >95%, and for 60°<α, the percentage of beads taking the +path was >90%. However, at such high angles, the motion of the beads across the MMA was not smooth and the transport efficiency was reduced.

The switch process is controlled by controlling the threshold magnetization angle depending on the properties of the SPM beads such as size and magnetization. The arrangement was operated in an exemplary method of the present specification with commercially available 5 μm beads (Spherotech, Chicago, Ill.), that have a 4.5% iron content (compared to the ~10% of the 2.8 μm beads). For these beads the threshold α angle was found to be around ±50°. This fact allowed to implement on-chip size selective separation for a particular range of magnetization angles.

FIGS. 17a and 17b present the motion of 2.8 and 5 μm beads across the tri-magnet junction for α=−50° demonstrating that the smaller magnetic particles travel in the +micromagnet path while the larger magnetic particles travel into the −micromagnet path. Size separation has been tested with $10°<\alpha<70°$ with the highest sorting efficiency achieved at $\alpha$ magnitudes between 45° and 55°. FIG. 17d presents the results of size selection of this system for the 2.8 and 5 μm beads moving across a tri-micromagnet junction for $\alpha=-50°$, 0° and 50°. These results can be used to calculate a separation efficiency $\varepsilon=1-f_{5\ \mu m}-f_{2.8\ \mu m}$, where $f_{5\ \mu m}$ and $f_{2.8\ \mu m}$ are the fraction of 5 μm and 2.8 μm beads not travelling along the expected direction. The efficiencies were found to be 85.0±12.3%, 26.6±18.8%, 60.6±7.8% for $\alpha=-50°$, 0° and 50°, respectively. The different efficiencies were attributed to local imperfections of the MMA. Additional modelling of the local magnetic field on the MAA was performed using finite elements calculations to gain insight into the mechanism of separation of the SPM beads. FIG. 17c presents the results of a set of calculations on the diverging micromagnet array as the orientation of the external magnetic field, $\vartheta_{xz}$, is rotated from 0°, to −360°. Coloured areas have high local magnetic fields into which the SPM beads are drawn, i.e., low magnetic potential energy. Several observations can be made from these calculations. First, that local magnet field moves in the positive x-direction as the external magnetic field is rotated in a clockwise orientation. Second, the $\alpha=-50°$ orientation of the micromagnet moment results in the oscillation of the highest magnetic field from the positive to negative side of the micromagnets as $\vartheta_{xz}$ varies from −90° to −270°. It appears the 2.8 μm beads follow the local field maximum after crossing the junction and travelled along the +direction, whereas the 5 μm beads jump to a second field maxima with higher magnitude located along the opposite path and travelled along the −direction. In summary, our novel design enabled us to set a preferential direction for the direction of the bead movement on the MMA, and to separate two distinct bead populations.

Example

Programmed Manipulation of Single Cells

Figure 18:
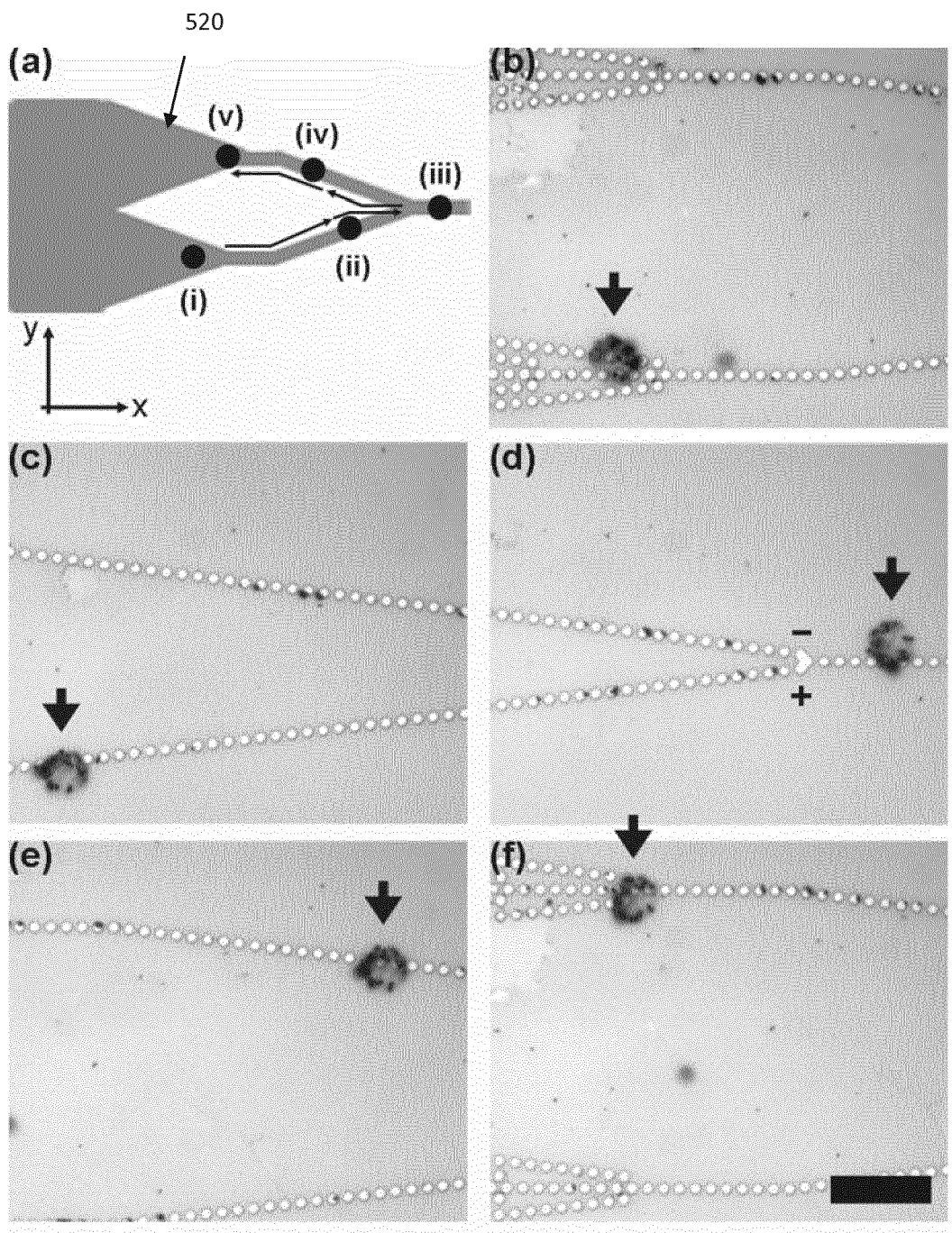
FIG. 18 showing an exemplary arrangement according to the present specification providing programmed transport of a single MDA-MB-231 cell labelled with 1 μm SPM beads.
Figure 19:
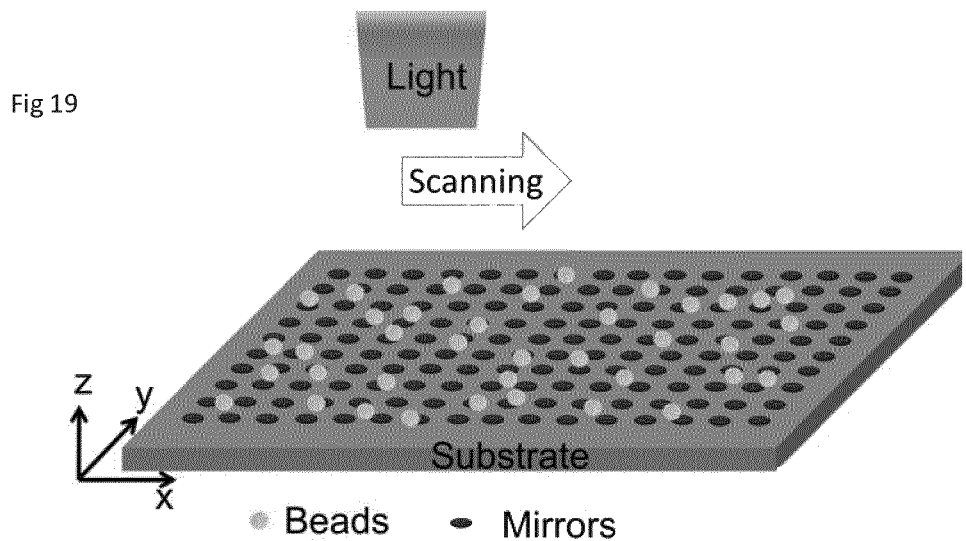
FIG. 19 in an alternative arrangement a Chromium micromirror array is used on silicon substrate and produce a highly reflective micro-mirror array on substrate. The particles (not limited by magnetic particles) were dispensed randomly on the substrate. Without using magnetic field to move particles, the laser beam from optical detection system scans the whole detection area in sequence by using motorized x-y stage. Therefore, high sensitive detection, as similar as that by using MMMA, can also be achieved.
Figure 20A:
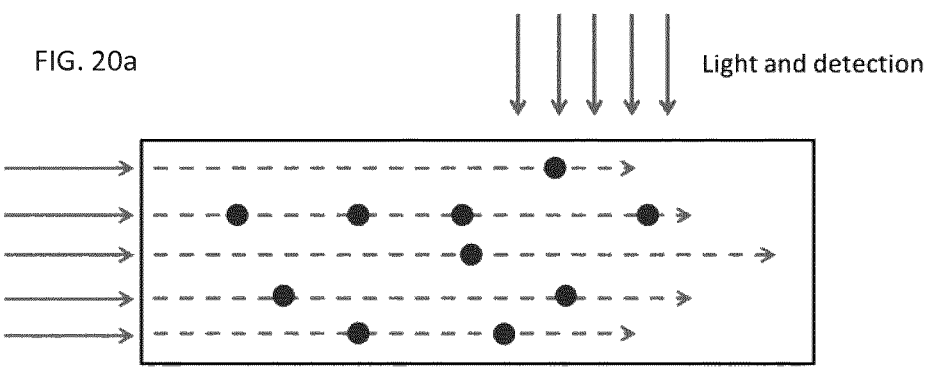
FIG. 20, in an alternative method without micro-magnet/mirror array (MMMA), particles are introduced into flow chamber by flow and then optically detected by a laser beam above the flow chamber. The detection resolution is limited by three factors: 1. To sensitively detect the particles, laser beam needs to be focused on the particles. However, without particle focusing, the particles distribute randomly in each laminar flow layers in vertical direction. Therefore, it's difficult to focus laser on all particles; 2. without discrete micro-mirror array on the bottom of flow chamber, it's found that the detection signal to noise ratio is low; 3. without micro-mirror array, the particles moving speed are difficult to know.
FIG. 20b, with MMMA on the bottom of detection chip, combined with magnetic capturing, the particles can be focused on MMMA to achieve more sensitive optical detection. Due to periodic MMMA, the motion of particles can be precisely monitored during detection. The signal to noise ratio of detection is also dramatically improved compared with that of previous method.
Figure 20B:
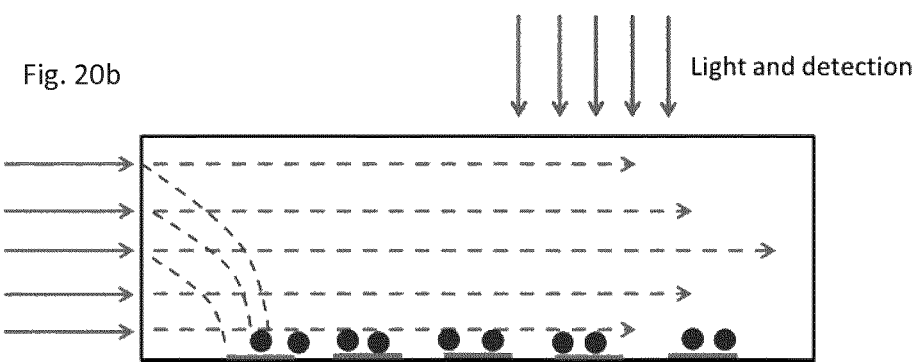
Figure 21:
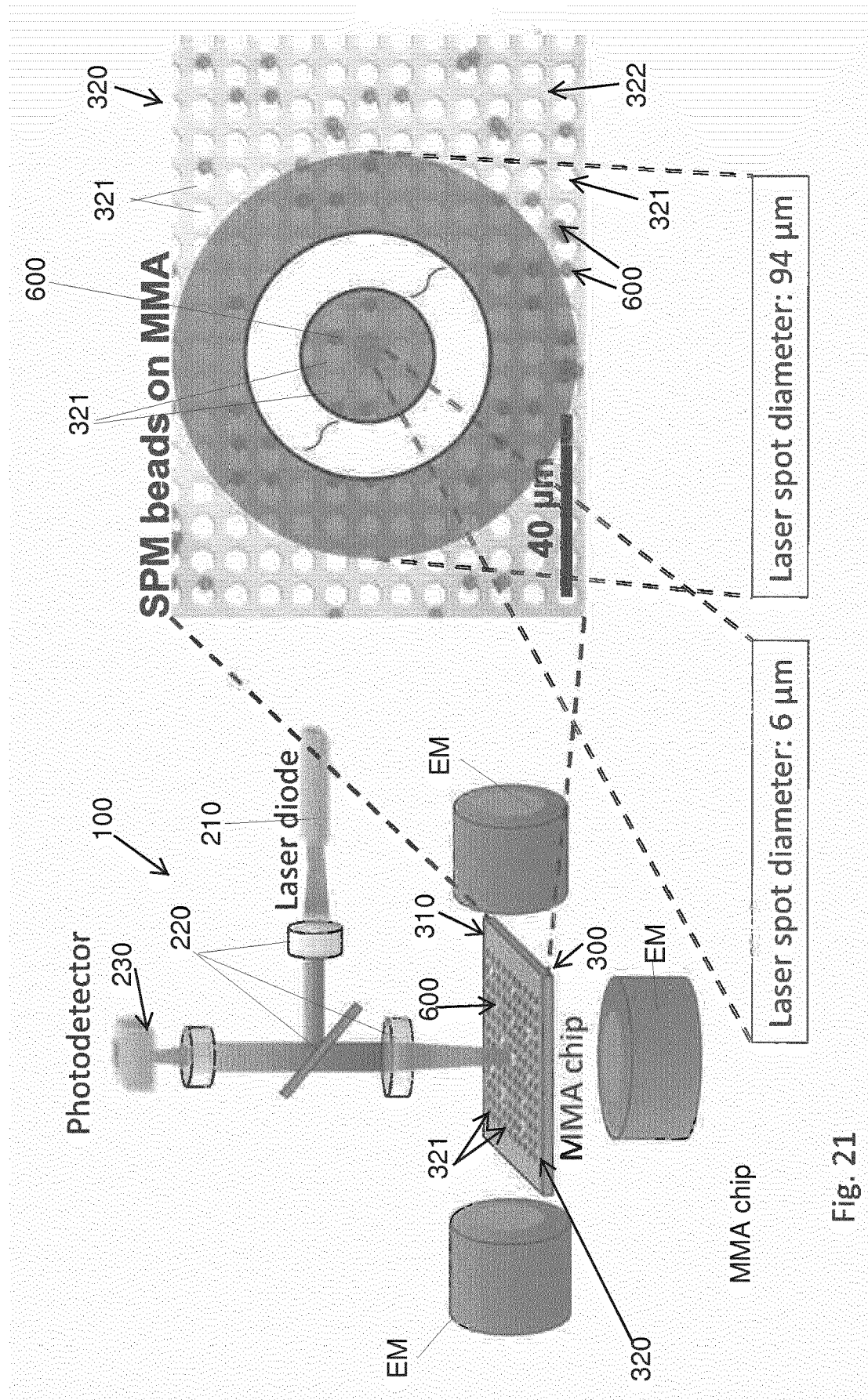
FIG. 21 As shown in the figure on the left side, light from laser diode is collimated and focused on the micromagnets array (MMA chip) where all the suspended beads are travelling using non-linear magnetophoresis principle. Depending on the distance of the collimator from the laser diode and divergence angle of the laser beam, different laser spot sizes can be achieved. For the experiments, a highly divergent 635 nm laser diode and a lowly divergent DPSS 532 nm laser diode have been used to achieve laser spot diameter of approximately 94 µm and 6 µm respectively. When an external magnetic field is applied using the electromagnet, beads start moving across the magnetic field. The change in intensity in the graph above represents the exact periodic behaviour of the signal.
Figure 23A:
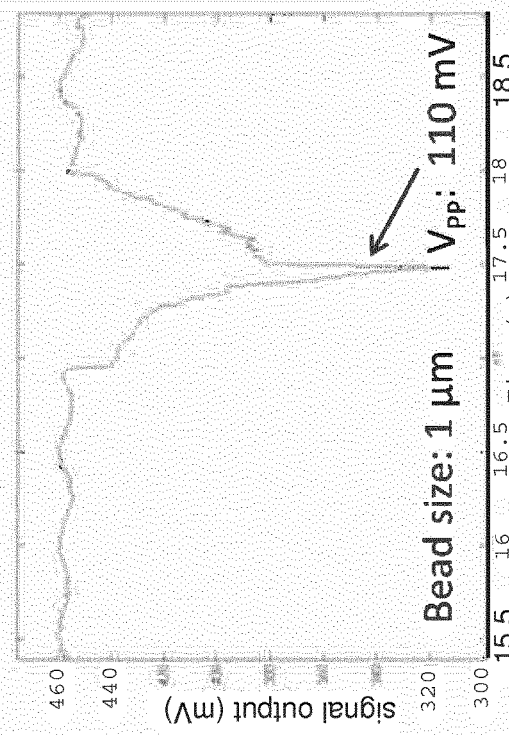
FIG. 23 Graphs above show comparison of different peak to peak signal for different size of SPM beads. It proves the sensitivity of the opto-magnetophoretic device by detecting as small as 0.5 µm bead with higher signal to noise ratio.
Figure 23B:
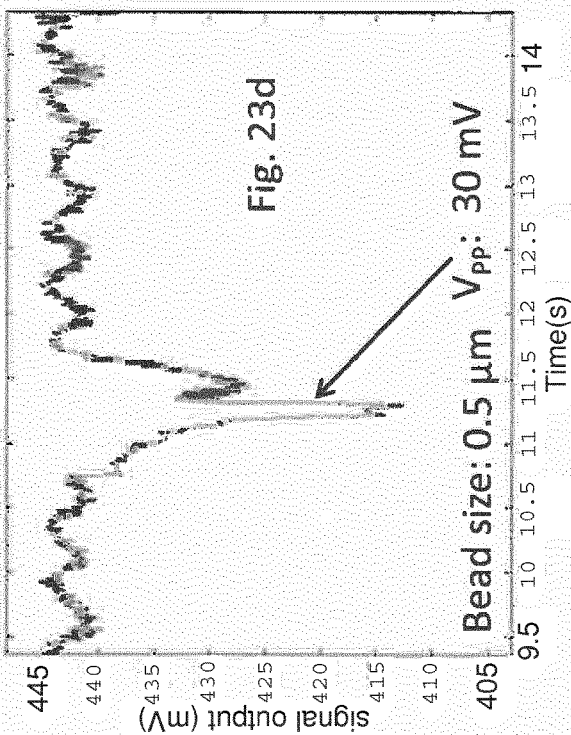
Figure 23C:
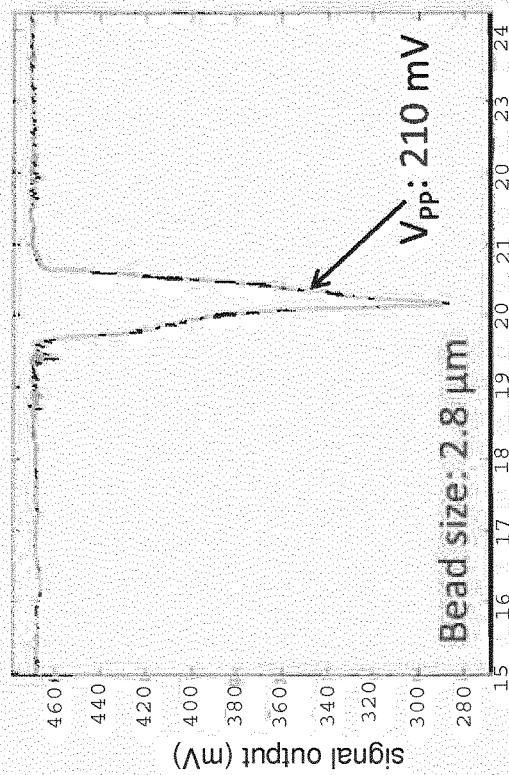
Figure 23D:
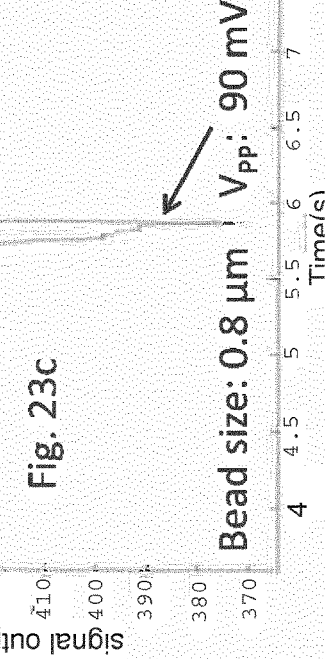
Figure 24:
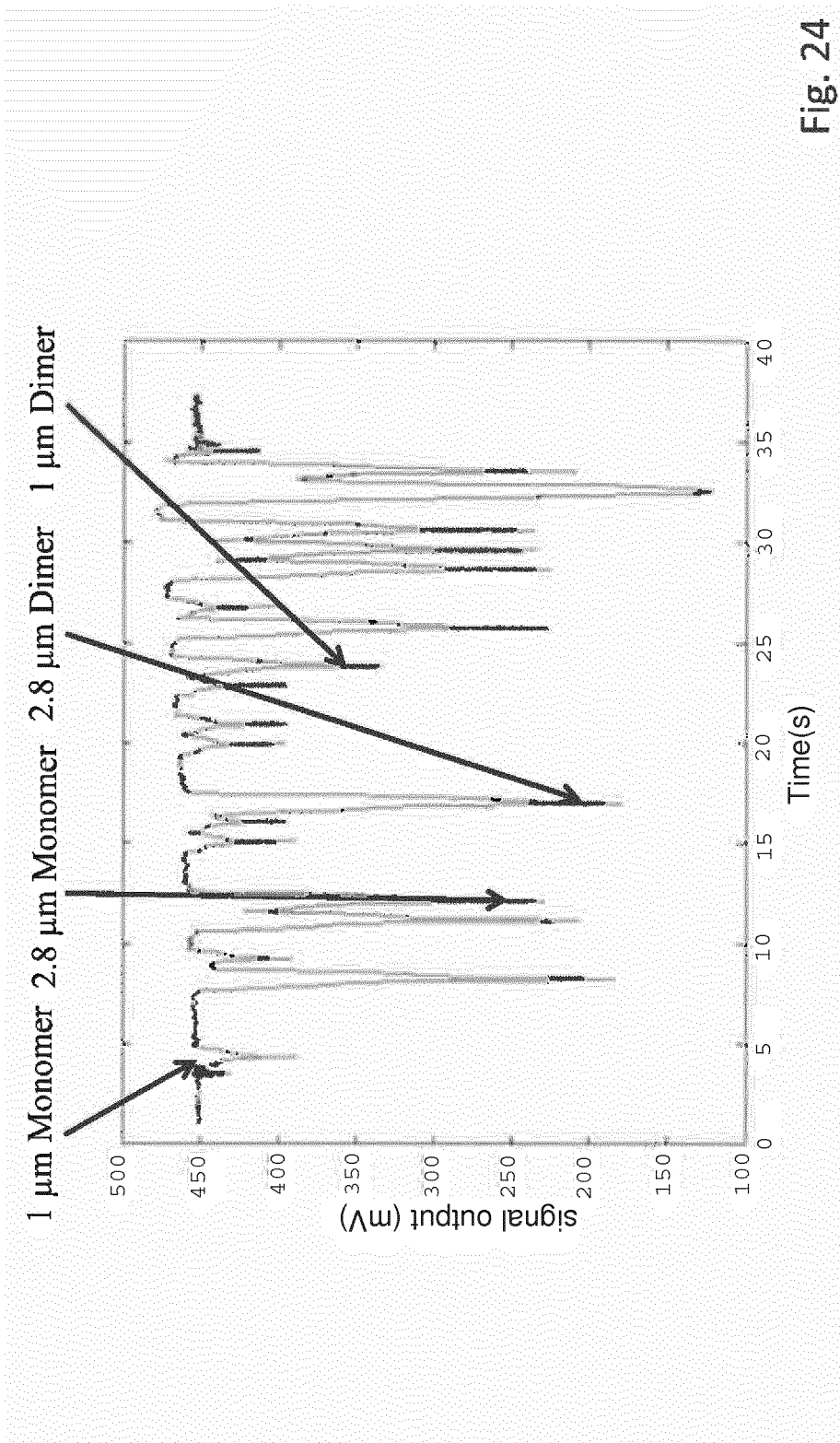
FIG. 24 is an illustration of an arrangement using a smaller spot size: 1 µm and 2.8 µm SPM beads FIG. 25 Larger spot size: Signal comparison at different driving frequencies the optical signal for different sizes of beads at different driving frequency in order to understand if we are able to observe the critical frequency and immobilization frequency. We know from the theory that as the frequency increases the velocity of the beads should increase and the signal pulse width should decrease which can also be noticed in the signal above. On the signal below black and red line represents the frequency vs signal peak measurement for 1µ and 2.8µ beads respectively Based on this we are able to know the immobilization of Two beads and that produces an effective detection system for NLM separation.
Figure 26A:
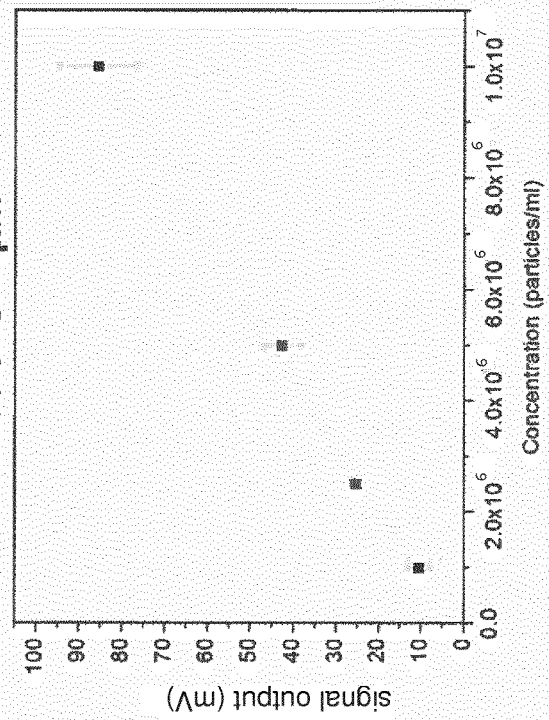
FIG. 26 Larger spot size: Comparison of beads with different sizes.
Figure 26B:
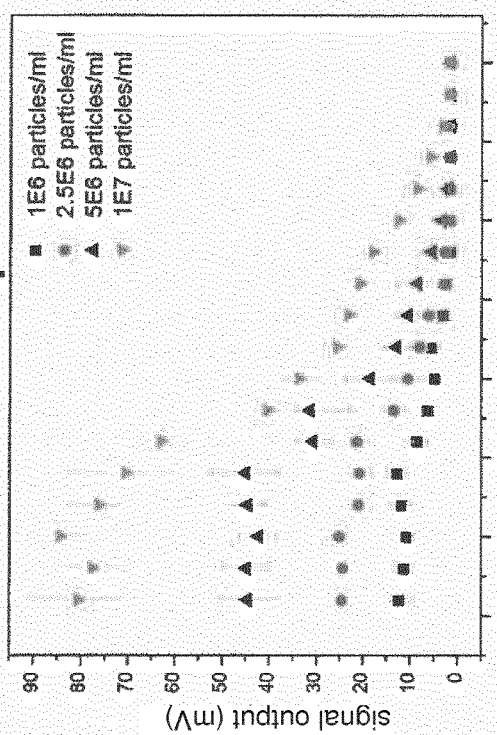
Figure 26C:
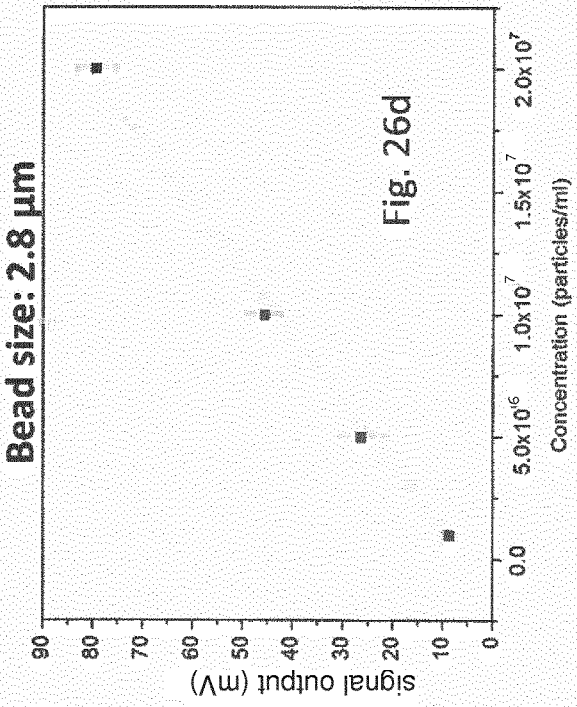
Figure 26D:
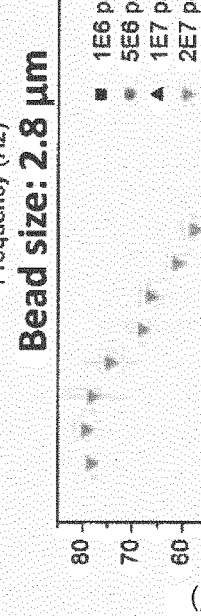

The capacity to control the direction of SPM bead motion may be used to transport beads and biological samples labelled with SPM beads to specific regions on a LOC device according to a method and system of the present specification. In an exemplary arrangement, as described with reference to FIG. 18, the controlled transport of MDA-MB-231 breast carcinoma cells labelled with 1 μm magnetic beads. These cells were specifically labelled with the SPMs using beads functionalized with an antibodies against the cell membrane protein CD9 or tetraspanin. FIG. 18a presents a schematic of the design of the experiment in which the cell was moved along a line of micromagnets from point i to ii using an external magnet field rotation in a clockwise orientation. At point iii the orientation of the external magnetic field rotation was reversed and bead moved along the +line of micromagnets through points iv and v.

FIG. 18b-f presents the sequential steps of the cell manipulation. In this example, the labelled MDA-MB-231 cell was transported in the y-direction by using the focusing capacity of a converging MAA and then the separating capabilities of a diverging MAA. The magnetisation of the MAA was $\alpha=-30°$. As predicted from the SPM bead separation results, the large SPM bead labelled cell crossed the junction by taking the preferred +direction. This experiment demonstrated the transport of individual cells from one region of the chip to another by simply adjusting the orientation of rotation of the external magnetic field for a programmed magnetization angle of the MMA. This feature may be incorporated in more complex networks of micromagnets to direct magnetically-labelled cells to any arbitrary position in the xy plane, e.g., to specific regions of the chip for subsequent biological analyses.

MMA arrangements for the focusing of SPM beads using two converging MMA designs and the separation of SPM beads using a diverging MMA design. On-chip focusing and transport of a magnetically labelled cell was also showed. The focusing MAA enables the concentration of large number of cell-SPM bead complexes into a single, synchronised line permitting rapid analysis based on the use of a single optical detector. The separation of cells labelled with one or more antibody functionalised SPM bead would make possible to isolate rare cells types from complex mixtures such as blood without exposing them to harsh separation conditions. In principle, local magnetic fields may be applied to specific regions of LOC devices to provide means to locally concentrate, separate, analyse and even modify cells attached to SPM beads. This suggests that these tools will allow us to direct SPM beads and biological specimen to desired regions on the chip for chemical reaction or analysis independently of the local hydrodynamic conditions. Chips configured taking account of these principles provide allow highly sensitive, multiplexed bioassays to be performed on rare species in complex media, such as, viruses, bacteria, or cells.

An Exemplary Arrangement According to the Present Specification is Provided as Follows: It Will be Appreciated that Different Suitable Alternative Arrangements May Also be Provided.

Chip fabrication. The micromagnet arrays were fabricated through standard photolithographic process in a Class 100 cleanroom using S1813 positive photoresist (Shipley Microposit, Marlborough, Mass.) irradiated with ultraviolet light (365 nm) at a dose of 60 mJ. The micromagnets were created via electron-beam metal deposition (Kurt J. Lesker Company, Hastings, UK). The structure of the micromagnets consisted of an initial 10 nm layer of chromium, followed by a 100 nm layer of cobalt, and another 10 nm layer of chromium. The bottom chromium layer enhances the adhesion of the magnets to the silicon substrate and the top layer protects the cobalt from oxidation. After the lift-off, the wafer was spin-coated with a 600 nm layer of spin-on-glass (Filmtronics, Butler, Pa.) and cured at 300° C. for 3 h in a furnace under nitrogen environment. The micromagnets were then magnetized using 11 kiloGauss impulse magnetizer (ASC Scientific, Carslbad, Calif.). Experimental setup. A magnetic field rotating in a plane orthogonal to the axis of motion of the beads was generated by three electromagnets arranged along mutually orthogonal axes. The solenoids were composed by 570 coils surrounding a cylindrical iron core (ASTM A536 ductile iron) 150 mm long and with diameter 60 mm. The sinusoidal signal necessary for a rotating field was created by a two channel function generator (Tektronix, Beaverton, Oreg.) that produced two sinusoidal waves with a 90° phase difference. Two programmable amplifiers (Kepco, Flushing, N.Y.) were used to amplify the signal and to supply it to the electromagnets for generating a magnetic field with components of 30 G in the x-direction and 60 G in the z-direction that was used consistently in all experiments. Imaging was performed using an epi-illumination optical microscope (Zeiss Axioskop2, Welwyn Garden City, UK) equipped with a 20× objective and an high-speed camera (Axiocam, Hsm, Zeiss).

Bead functionalization. The antibody functionalization was performed on 1 μm carboxylated beads synthesized in our laboratory. The beads were re-suspended in MES buffer (2-(N-morpholino-ethanesulfonic acid) pH 6.1, at a concentration 108 beads/ml. The beads were washed three times with MES buffer. A magnet rack was used to hold the beads during the washing steps. After being washed the beads were re-suspended in 500 µl MES buffer. 10 mg EDC (1-Ethyl-3-(3-dimethylaminopropyl-carbodiimide) were dissolved in 1 ml MES buffer, and 10 mg sulfo-NHS (N-Hydroxysuccinimide) were as well dissolved in 1 ml MES buffer. 290 µl of the EDC solution and 290 µl of the NHS solution were added to the beads and they were briefly sonicated (three times 1 s sonication with 3 s intervals). Then the solution was incubated for 15 min at room temperature on a rotating rack. After the incubation the beads were washed once and re-suspended in 500 µl MES buffer. 50 µl of antiCD9 antibody (HansaBioMed, Tallinn, Estonia) having a concentration of 1 mg/ml was added to the beads. The solution was then incubated for 1 h at room temperature on a rotating rack and then moved at 4° C. for an overnight incubation. The next day the beads were washed twice with PBST, re-suspended in 1 ml PBS buffer and stored at 4° C.

Cell targeting. MDA-MB-231 breast carcinoma cells were cultured in Dulbecco's Modified Eagle Medium (DMEM) supplemented with 1% Penicillin/Streptomycin and 10% foetal bovine serum. The cells were seeded in a T25 culturing flask and placed in a C02 supplied incubator at 37° C. Cells up to passage 5 were used in the experiments. For the labelling procedure the cells were detached from the culture flask using trypsin-EDTA (Gibco, Carlsbad, Calif.). The suspension was placed in a 15 ml tube and centrifuged at 900 rpm for 3 min to form a cell pellet. The culturing medium was replaced with PBS buffer and the cells were counted using a hemocytometer. The cell suspension was diluted and samples containing 105 cells in 1 ml PBS buffer were prepared. $5\times10^6$ magnetic beads were added to the each sample. The cells and the beads were incubated for 1 h at room temperature on a rotating wheel. After the incubation the microcentrifuge tubes containing the cells and the beads were brought to direct contact with a permanent magnet for 1 minute, followed by a brief vortex shake. This step was to increase the binding probability. The binding was assessed by comparing antibody-coated beads with non-coated beads. When non-coated beads were used almost no binding between the beads and the cells was observed, whereas cells were covered with anti-CD9 coated beads Referring to FIGS. 19 to 28, various arrangements according to the present application of the light source for the detection system are described. The light source of the arrangements of the present application may be for example a laser source. It will be appreciated that more than one light source maybe provided just as it is has been described that more than one detector may be provided. The illumination is controllable to support different settings and different detected signal as required. A larger laser spot size is used for example to support detection across the substrate or for example the micro-magnet array of the substrate or a micro-magnet array of the substrate.

Larger spot size: Comparison of beads with different sizes
Larger spot size: Comparison of beads with different magnetization
Larger spot size: Calibration curves
Linear relationship for the optical signal vs number of particles passing through the laser spot Calibration curves can be used for optical signal data evaluation
A smaller laser spot size may be used for example to support detection at a particular point on the substrate.

Smaller Spot Size
Higher sensitivity in terms of bead size up to 0.5 µm
Higher Resolution with distinct signal for 0.8 µm and 1 µm sizes of beads
Distinct signal for monomer and aggregates for the same sized beads
Achievable throughput:
   1 µm: 18000 beads/hour ($\omega_c$=5 Hz)
   2.8 µm: 90000 particles/hour ($\omega_c$=25 Hz)
Larger Spot Size
Higher sensitivity in terms of analyte/bead concentration
Higher throughput by simultaneous and quicker analysis of same sized beads
Distinct signal for different concentration of the same sized beads
Separation of SPM beads with biological targets can be optically monitored, reaching sensitivity up to femto-molar range.
Achievable throughput:
   1 µm: 198000 beads/hour ($\omega_c$=5 Hz)
   2.8 µm: 990000 particles/hour ($\omega_c$=25 Hz)
It will be appreciated that the system may include multiple light sources and multiple detectors arranged in the various configurations.

Applications and Advantages

The non-linear magnetophoretic (NLM) separation system is a high resolution separation technology and is capable of sorting of SPM particles and their biological attachments based on their hydrodynamic and magnetic properties.

In an NLM separator, the SPM particles are separated on periodic micro-magnets array (MMA) in external rotating magnetic field. The travelling magnetic wave created by combination of local magnetic field and external magnetic field manipulates the SPM particles move in surrounding fluid, which exert opposite hydrodynamic forces on moving particles, at different mobility in programmable rotation frequency of rotating field.

The moving speed of SPM particles is linearly proportional to rotation frequency of rotating field at low rotation frequencies. But at the rotation frequency higher than a critical frequency for particles, the moving speed of particles starts to diverge with rotation frequency and decreases as the rotation frequency increased. Finally, the particles are immobilized completely on MMA at their immobilization frequency. The critical and immobilization rotation frequency is closely associated with magnetic moment and hydrodynamic drag factor of particles. Different particles configurations have different critical and immobilization frequencies on the same MMA, fluid, and rotating magnetic field. By attaching biological analytes, such as antibodies, cells, DNAs, and bacteria, etc., on the SPM particles, the hydrodynamic drag factor of particles can be changed or the bonding aggregates of particles can be formed. In both scenarios, the critical and immobilization frequency of bio-functionalized particles or aggregates will vary compared with original particles. Based on that, bio-separation can be performed with relative high efficiency, due to almost infinite resolution of nonlinear magnetophoresis. Flow enhanced NLM (FNLM) is a further enhanced version of NLM technology. In an FNLM separator, the micro-fluidic flow chip has been used to house the MMA to introduce a laminar flow instead of static fluid in NLM separator. The laminar flow provides additional hydrodynamic forces on separated particles and sweeps them downstream with flow in controlled manner. By using this method, large amount of particles can be separated more quickly, efficiently, and continuously compared with NLM separation. High performance separation process can be carried out in microfabricated NLM/FNLM micro-chip without using additional imaging device.

The present arrangement which provides an integrated detection and NLM/FNLM separation system and provides a quick, efficient, sensitive, non-damage, inexpensive, and portable method to detect the moving particles and their biological attachments in NLM/FNLM separator.

The present invention uses integrated optical detector, laser, and analyzer to build an effective optical detection system integrated with and based on NLM transport of SPM particles or objects (ONLM) to monitor and analyze the particles properties on NLM/FNLM separator.

An adjustable laser is provided to illuminate the substrate or the surface of MMA, on which the SPM particles are dispensed, and the detector detects the reflective light from the MMA. The MMA of an exemplary arrangement of the present specification comprises of periodic metal (Chromium coated Cobalt) micro-magnets, configured accordingly to act like an array of micro-mirrors and can reflect the incidence light back to the detector with high reflectivity. In contrast, the magnetic particles are generally optically dark with much lower reflectivity compared with metal micro-magnets array. The presence of SPM particles on MMA can affect the intensity of reflective light to the photodetector. The sizes and the number of particles on MMA, the optical properties of particles, fluid properties in NLM/FNLM chip, and the surface conditions of MMA can affect the output of photodetector in the ONLM system. Such information can be obtained by analyzing the calibrated signal from ONLM. It is known that the magnetic mobility of specific SPM particles in NLM/FNLM can be well controlled by rotating magnetic field and surround fluid. As particles moving on the micro-magnet or micro-mirror array, the reflective light from mirrors array may be modulated by moving particles. The modulated outputs of photodetector on ONLM provide an effective way to sense the behavior and properties of SPM particles in an NLM/FNLM separator system. In NLM/FNL separator, different particles have different critical and immobilization frequencies in rotating field. Moreover, the proportion of immobilized particles at certain rotation frequency is different for different particles. By analyzing the signal intensity and frequency response of ONLM outputs, the information about the critical and immobilization frequency, which are associated with magnetic moment and size of SPM particle, numbers of particles, and optical properties of particles, can be acquired. The integrated ONLM combining with NLM/FNLM separator provides an effective way for sensing of magnetic particles and their biological bound attachments in additional of separation of those objects in NLM/FNLM separator simultaneously.

In an exemplary arrangement of an ONLM system according to the present specification there may be provided at least a single wavelength solid laser source, and a silicon photodetector, which is sensitive to the laser, an objective lens, which focuses the laser to the micro-mirrors array and collects the reflective light to the photodetector, and data acquisition card and processing software. Alternatively, a halogen light source and switching mirrors, CCD camera, and optical beamsplitter may also be used for imaging and visualization. The NLM/FNLM is provided with an optical transparent window above the micro-mirrors array for clear laser and reflective light pass. The ONLM system is integrated and aligned with an NLM/FNLM separator. In addition, the broad wavelength of incident light or multiple numbers of lasers can be used for sensing of multiplex particle and biological analytes, which also can be fluorescently labeled. To achieve highest sensitivity, array of photodetectors or multiple photodetectors also can be used in ONLM. As a result, the suitable beamsplitter and optical mirrors may need to be properly fitted in ONLM.

As described above in an alternative arrangement on-chip particle focusing MMA 520 may be used to focus large number of particles to a fixed detection area 550 on the MMA for an efficient high throughput detection of the particles. The typical focusing MMA is a variant of regular lattice-like MMA. It has angularly aligned micro-magnets lines instead of a lattice-like arrangement of micro-magnets in the regular MMA.

The focusing MMA 520 comprises multiple micro-magnets lines or tree-like hierarchical structure for multi-step focusing. The focusing MMA can be easily integrated with an optical detector similar to the regular MMA chip. The integrated focusing MMA provides a powerful tool for efficient focusing and detection of SPM particles or biologicals attached to the particles on the MMA without requiring a hydrodynamic flow or any modification in the chip or the fluidic chamber.

It is noted that the preferred diameters of SPM particles are typically from sub μm to tens μm, which are comparable with dimensions of metal micro-magnets and act as suitable modulators for highest sensing resolution.

The present invention can be applied to detect not only magnetic micro-particles, but also macromolecules, e.g., DNA, RNA, proteins, and antibodies, as well as cells, e.g., stem cells, erythrocytes and white blood cells, and pathogens, e.g., viruses, and bacteria.

The system and method of the present specification accordingly finds many analytical, diagnostic, and medical applications.

The present invention is described in greater detail herein below with reference to the drawings, particular structures of configuration, physical properties, materials, and application examples.

Advantageously an Optical detection system based on NLM transport of SPM particles (ONLM) is provided integrated with an NLM (FNLM) separation system. An improved detection of SPM particles and biological materials is supported. Advantageously, the system includes bio-compatible, inexpensive, fast, sensitive, easy to use, and multiplex detection. Suspensions of a mixture of SPM particles and biological attachment can be qualitatively or quantitatively measured by using an ONLM device according to the present specification. In addition, a modified MMA can be used to achieve on-chip particle focusing for manipulating and detection of a large amount of particles efficiently. Moreover, the system provides a portable, sensitive, and inexpensive diagnosis instrument for point of care applications.

The methods and systems according to arrangements of the present specification have been described with reference to particular examples for purpose of clarity and understanding. It should be appreciated that certain modifications and improvements can be practiced within the scope of the appended claims and their equivalents.

A system combining detection and separation functionality together is often highly demanded in practice. The present lab-on-a-chip technology is capable of integrated on-chip focusing, optically sensing, and separating the micro-particles and biological analytes simultaneously making it advantageous for analytical and clinic use. The present invention combines high resolution magnetic separation and optical detection together by means of lab-on-a-chip technology i.e. miniaturized instrument with high precision. It delivers fast, inexpensive, simple, multiplex, portable, high resolution of separation and detection, and high throughput for point-of-care application. Advantageously a simple, fast, relatively inexpensive system for multiplex biological separation and sensing simultaneously is provided. The arrangement of the system and method of the present specification provides on chip detection of different size or concentration of magnetic particles attached to different biomolecules and their clusters when they are separated in real time. In the reflection arrangement of an exemplary arrangement, a monochromatic laser illuminates the highly reflective periodic micro-magnets array surface and generates a signal with an amplitude representing the number of particles in the field of view of the photodetector.

Advantageous MMA arrangements for focusing and separating SPM beads based on non-rectilinear array geometries are provided. The MMAs were arranged and configured to collect beads dispensed on an array and organize them, for detection, for example in single files, thus facilitating the integration of the NLM separation and transport technology with optical or magnetic detection systems. The diverging arrays advantageously enabled programmable control over the trajectory of the beads. A tri-magnet junction for example may be provided to induce a preferential direction for the bead motion by tuning the orientation of the MMA magnetization, thus enabling "magnetic switch" functionality. The size dependent switching behavior of the SPM beads at the tri-magnet junctions according to the specification may be utilized for rapid and continuous separation of different bead populations without the need for changing the external magnetic field rotation frequency or hydrodynamic flow. The bead focusing and guiding capabilities of the device were used to control the transport of a magnetically-labelled analyte.

EXAMPLES AND EXEMPLARY APPLICATIONS OF THE SYSTEMS of the present specification Further examples and exemplary applications of the systems and method of the specification are described with reference to FIGS. 29 to 49.

Figure 37:
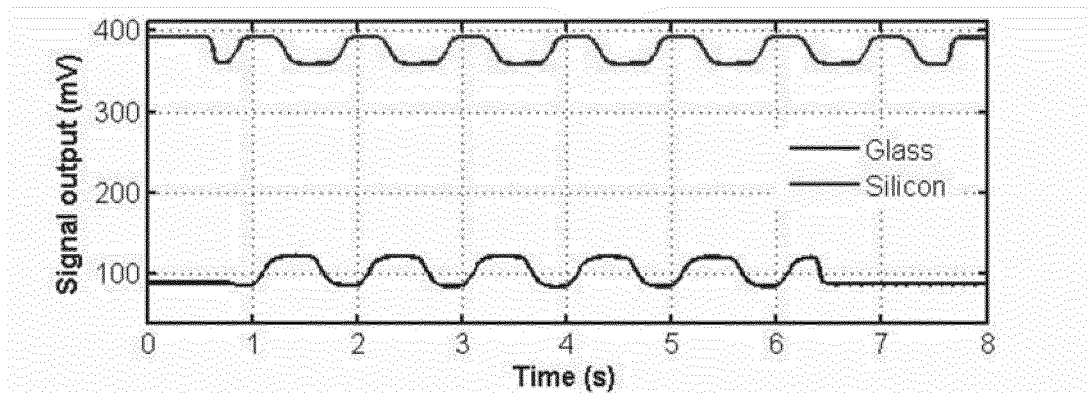
Figure 38:
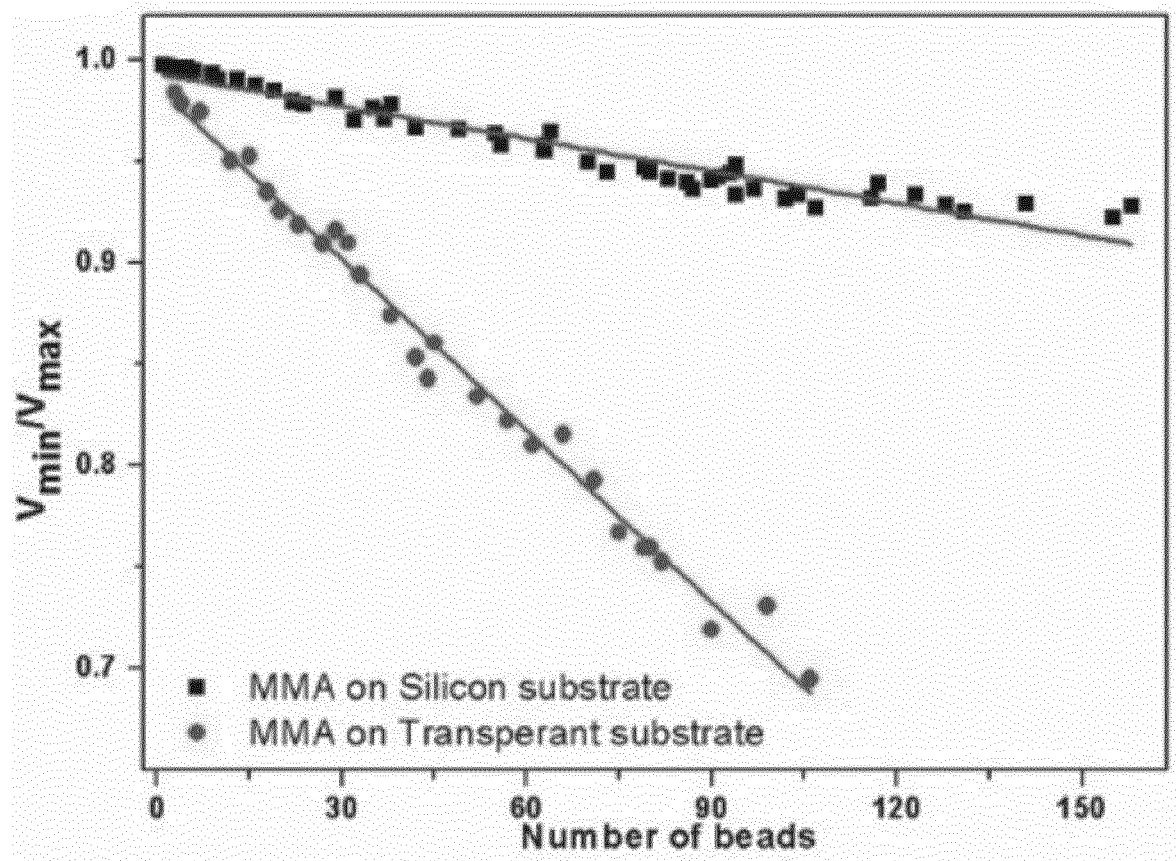
FIG. 38 Comparison of normalized Vmin/Vmax for silicon and glass substrates using FOV3 configuration.
Figure 43:
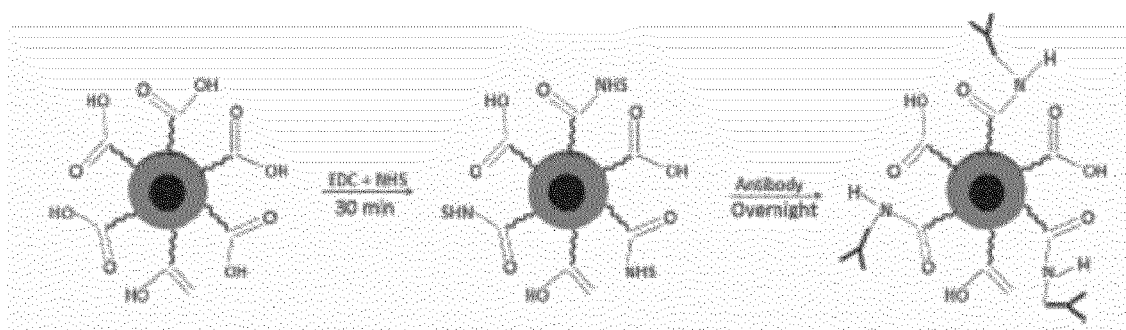
FIG. 43 Schematics of antibody functionalization: Y represents either antirat (goat) or antiherpes (rabbit) antibody.
Figure 44:
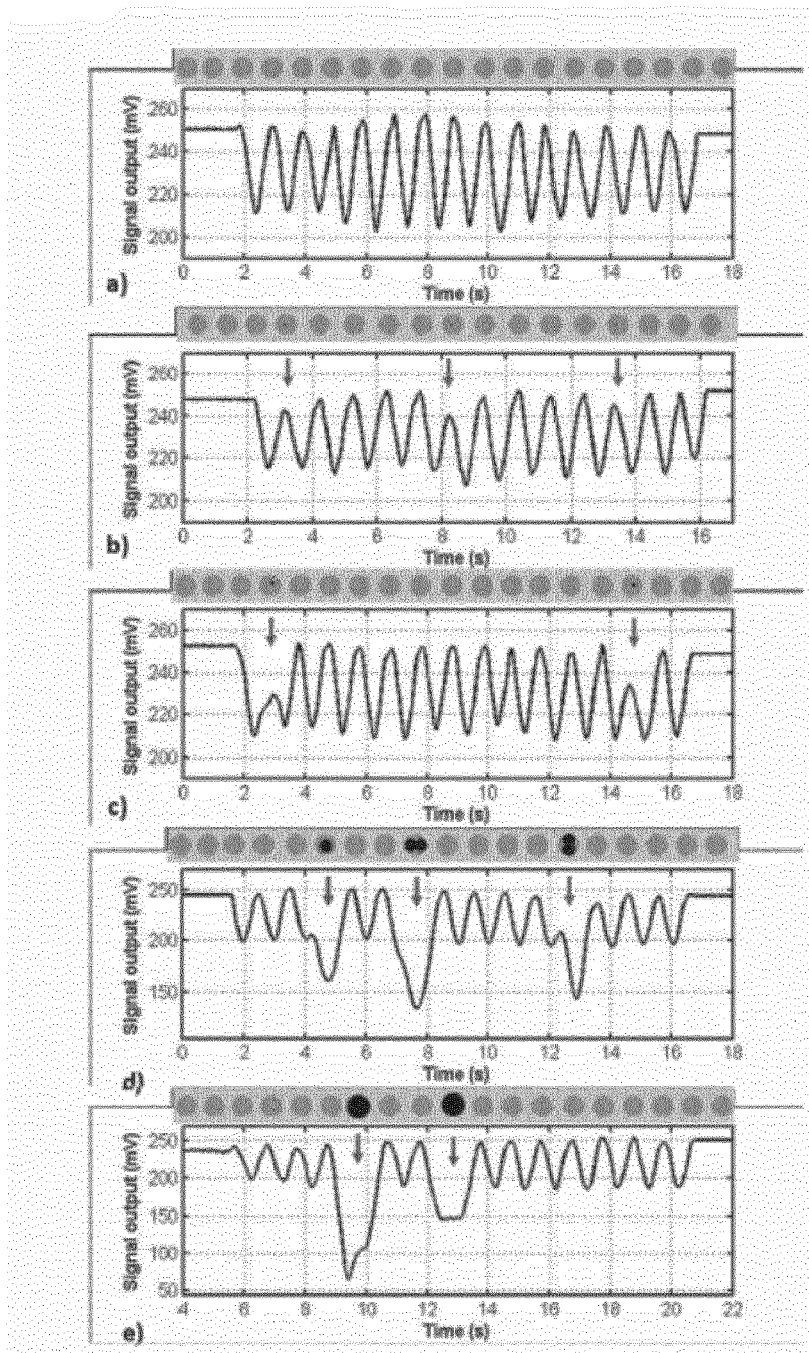
FIG. 44 Optical scanner signal characterization for beads captured on the micromagnets: a) No beads, b) 0.57 m, c) 1 m, d) 2.8 m, and e) 5.6 m diameter. Scanning is performed at motor speed of 8 m/s. Red arrows show relative position of the beads on MMA schematics.
Figure 47:
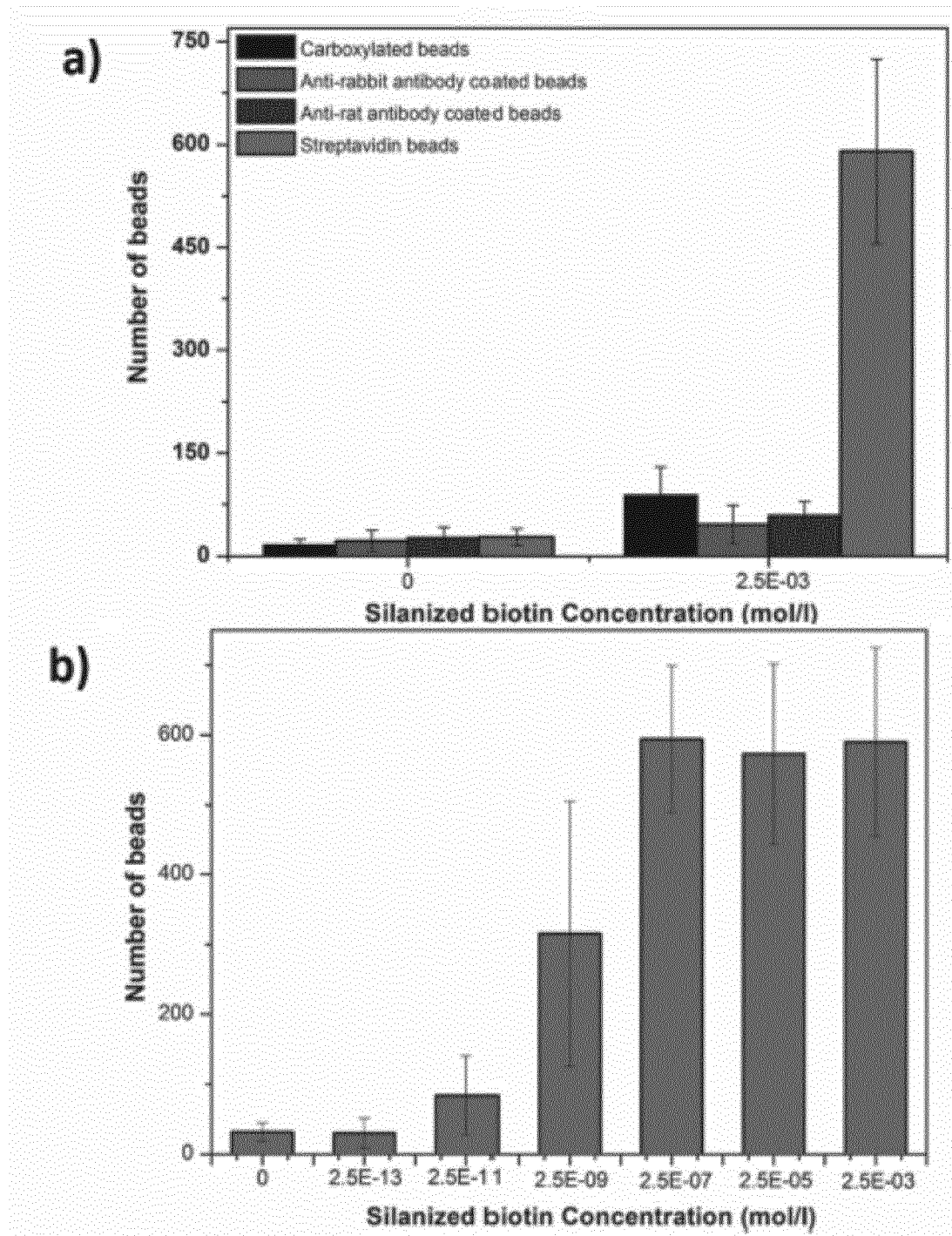
FIG. 47 Optical scanner a) Specificity analysis, b) Surface saturation analysis.

Referring to FIGS. 1 and 37 to 38 A method to increase the sensitivity of the optical detection system was described and tested. The output of the photodetector depends on the reflectance of both the substrate and the micromagnets. In order to verify the effect of substrate reflectance, an array of micromagnets was fabricated on a glass substrate using the procedure described earlier. The signal response for an exemplary case based on 100 beads on silicon and on glass substrate. Moreover, the signal responses were measured for different populations of beads on both MMA chip with silicon and glass substrates. Referring to FIG. 38, the slope of the signal decreases faster for glass substrate, showing a higher sensitivity, as compared to silicon substrate. Sensitivity may be further enhanced in that the micromagnets array could be fabricated using materials with higher reflectance.

The opto-magnetophoretic system has been presented which enables the tracking of SPM beads traveling on MMA chips for faster analysis, simultaneous detection and low volume intake. The system was tested for signal-to-noise ratio, limit of detection and frequency response for four different FOVs (fields of view) to track 2.8 micron beads. The effect of the composition of the SPM beads on MMA have been investigated by tracking their movement as a function of the frequency of the external magnetic field. The signal amplitude changed as a function of bead population and size of field of view. Due to the different reflectance values of the silicon substrates and the micromagnets, the unique phase-locked signal of the beads have been investigated. Numerical simulations show a close match with the experimental results, making the developed algorithm a tool to predict the signal response estimate unknown populations of beads quantitatively. This system allows to monitor the dynamics of micron/sub-micron diameter SPM beads without any expensive, difficult and complicated experimental equipment, especially because the dynamics of such beads are not well observable under the optical microscope. Calibration curves were created for the simultaneous detection of multiple beads traveling through an MMA chip surface and also frequency response was optically characterized 2.8 micron beads to ascertain the maximum achievable speed. The manipulation of multiple beads combined with real-time detection with single-bead resolution opens the possibility to perform on-chip assays. Force dynamics can be studied automatically opens wide range of possibilities for detection.

In FIG. 29 region (iii), a periodic variation in the signal corresponds to applied two-dimensional rotating magnetic field which induces the beads to oscillate around the micromagnets (when the beads are positioned on the micromagnets, the light hitting the high reflectance micromagnets is blocked, producing a low amount of light) reaching the photodetector, denoted as Vmin. In FIG. 29 region (iv), in the presence of a two-dimensional rotating magnetic field, the beads follow the periodically traveling potential energy minima and generate a periodically varying signal. Here, signal amplitude varies at each frequency cycle corresponding to the total number of beads in the field-of-view. Further, in regions (v) and (vi), the signal is similar to region (ii) and (i) respectively.

The arrangement of the specification provides an improved approach in optical detection to determine the number of beads and their size quantitatively in an automated manner.

FIG. 30 a) demonstrates that detection of size as well as different number of beads is possible with very high precision and accuracy when only one micromagnet was illuminated. On the other hand, FIG. 30 b) represents the example for the configurations where multiple micromagnets are illuminated. As different populations of beads travel on the substrate, they scatter different amount of light. In other words, as the number of beads in the field-of-view change, both Vmin and Vmax change. Further, the normalized signal amplitude Vmin/Vmax can be used to determine different populations of beads. Several conclusions were derived based on the primary observations. First, the difference between a random and a systematic distribution of the beads is distinguishable and the signal value depends on several parameters such as substrate reflectance, area of illumination, intensity of illumination and the inherent properties of the photodetector. Second, the signal is phase-locked with the external rotating magnetic field. Also, at any time point, the signal corresponds to their synchronized positions around or on the micromagnets.

Third, the amplitude of the periodic signal is directly proportional to the number of beads for that particular frequency cycle. On the other hand, the pulse width remains constant for a particular rotating field frequency as all the beads spend the same amount of time while crossing the high reflectance micromagnets. These observations are key to demonstrate the direct correlation between number of beads and the signal amplitude.

Phase-locked Regime—Further, the signal response was studied for different FOVs and for different numbers of beads to determine the experimental limit of detection, sensitivity, resolution and dynamic range of the system. In order to link the measured signal amplitude to the corresponding number of beads, the number of beads was determined using the optical microscope. It was clear that the normalized signal amplitude, Vmin/Vmax, decreased with the increase in the number of beads. The signal-to-noise ratio to detect a single bead decreased with an increase in FOV from 37, 10, 0.57 and 0 dB for FOV 1, 2, 3 and 4, respectively. The limit of detection (LoD) is defined as the minimum number of beads required to generate a signal-to-noise ratio (SNR) greater than one (the noise amplitude was 1.5 mV with corresponding Vmin/Vmax=0.997). For this system the sensitivity was found to be a single bead for FOV1/2, two beads for FOV3, and twenty-eight beads for FOV4. The sensitivity is defined as the slope of the red lines in FIG. 31. For FOV1, 2, 3 and 4, sensitivity is 0.13, 0.01, 1E-03 and 5E-05 respectively. It would appear that the smaller FOV system must be used if single bead sensitivity is required. To determine the resolution of the detection system, the relative intensity change was measured between two nearest populations. The minimum detectable difference between two bead populations is one bead for FOV1, two beads for FOV2, four beads for FOV3 and thirty-two beads for FOV4. In these measurements, the resolution was not only limited by the optical detector noise but also by non-specific adhesion of beads and bead aggregations due to dipole-dipole interaction in highly densebead populations. Further, the magnitude of the dynamic range in terms of number of beads appears to be zeroth, first, second and third order for FOV1, 2, 3 and 4 respectively. Using this information, the opto-magnetophoretic system can be tuned according to the requirements of the application.

Figure 32:
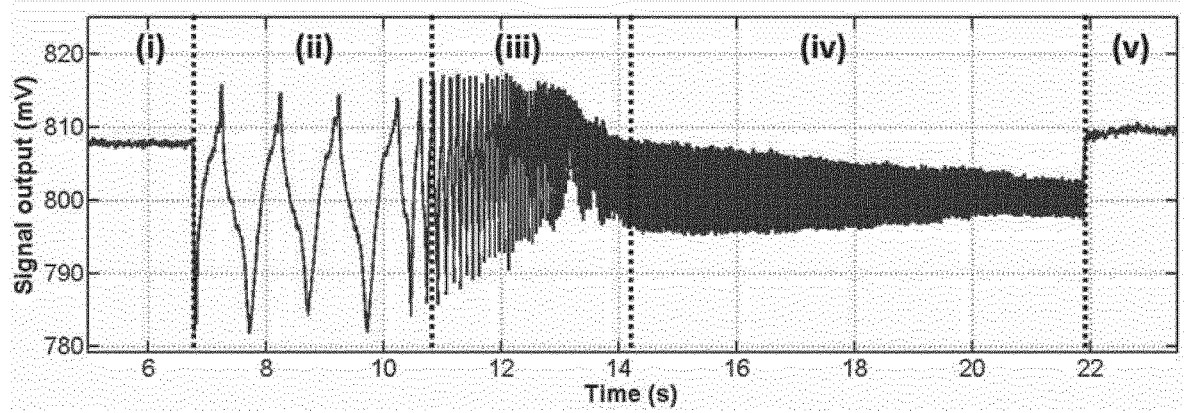
FIG. 32 Optical signal using FOV3 configuration for multiple 2.8 micron SPM beads traveling simultaneously across a MMA as the frequency of the external magnetic field is varied from 0 to 100 Hz. The five regions correspond to external magnetic field frequencies of i) ω=0 Hz, ii) 0<ω<ωc Hz, iii) ωc<ω<ωi Hz, iv) ω>ωi Hz, and v) ω=0 Hz.

For a complete characterization of SPM beads in the NLM system, all four optical configurations were further tested at different frequencies of the external rotating magnetic field keeping the population of beads constant. FIG. 32 presents the photodetector signal for SPM beads traveling on a MMA chip as the external magnetic field is rotated at frequencies increasing from 0 to 100 Hz. Five distinct regimes of signal can be identified that are linked to the motion of the beads on the MMA chip at different rotation frequencies of the magnetic field. In the absence of the external magnetic field, i.e., $\omega=0$ Hz, the signal was determined by the Brownian motion of the beads on the MMA chip and by the noise inherent to the optical systems of this type, as shown in regions (i) and (v) of FIG. 32.

When a low frequency external field was applied to the MMA chip, a periodically varying photodetector signal was generated due to the synchronized movement of the beads across the micromagnet and the silicon surface, which has varying levels of reflectance. For each rotation of the external field, the signal goes through a maximum (Vmax) and a minimum (Vmin), which represents their positions on the MMA chip at $\theta xz=0$_ and $\theta xz=180$ degrees, respectively. The SPM beads reside over the higher reflectance micromagnets at $\theta xz=180$ degrees which results in a lower level of reflected light. The absolute value of Vmax and Vmin is also closely linked to the total number of beads in the field of illumination of the optical detector. As the frequency of the external magnetic field increases, several amplitudes of the signal can be detected. As the frequency increases, the beads moved in phase with the external magnetic field until it reaches its critical frequency, $\omega c$, at which point the beads began to slip out of the traveling potential field and this corresponds to region (iii) in FIG. 32. As the frequency is increased further, at immobilization frequency, $\omega i$, the beads were not able to follow the traveling potential energy landscape and they oscillate around micromagnet. It has previously been reported that it is very difficult to numerically predict the transport behavior of SPM beads for $\omega > \omega c$.53.

The behavior of the beads in the presence of a one-dimensional rotating magnetic field at varying frequencies is presented, both experimentally and numerically, for various beads populations.

Figure 33:
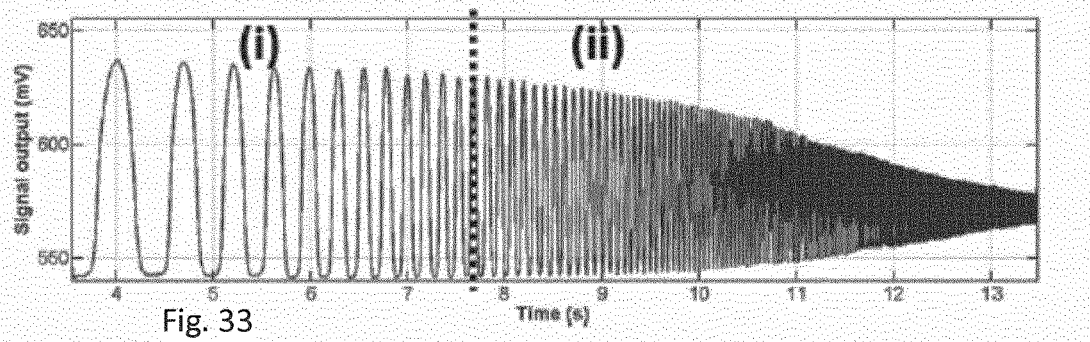
FIG. 33 Optical signal using FOV3 configuration for multiple 2.8 micron SPM beads oscillating simultaneously around the micromagnets as the frequency of the external magnetic field is varied from 0 to 100 Hz.

FIG. 33 shows b) shows an example of the simulated signal for 100 beads oscillating around the magnets using FOV3, at frequencies ranging from 1 Hz to 100 Hz. To compare the simulated signal with the experimental signal, 100 beads were located and actuated at frequencies of the external magnetic field ranging from 1 Hz to 100 Hz.

Figure 34:
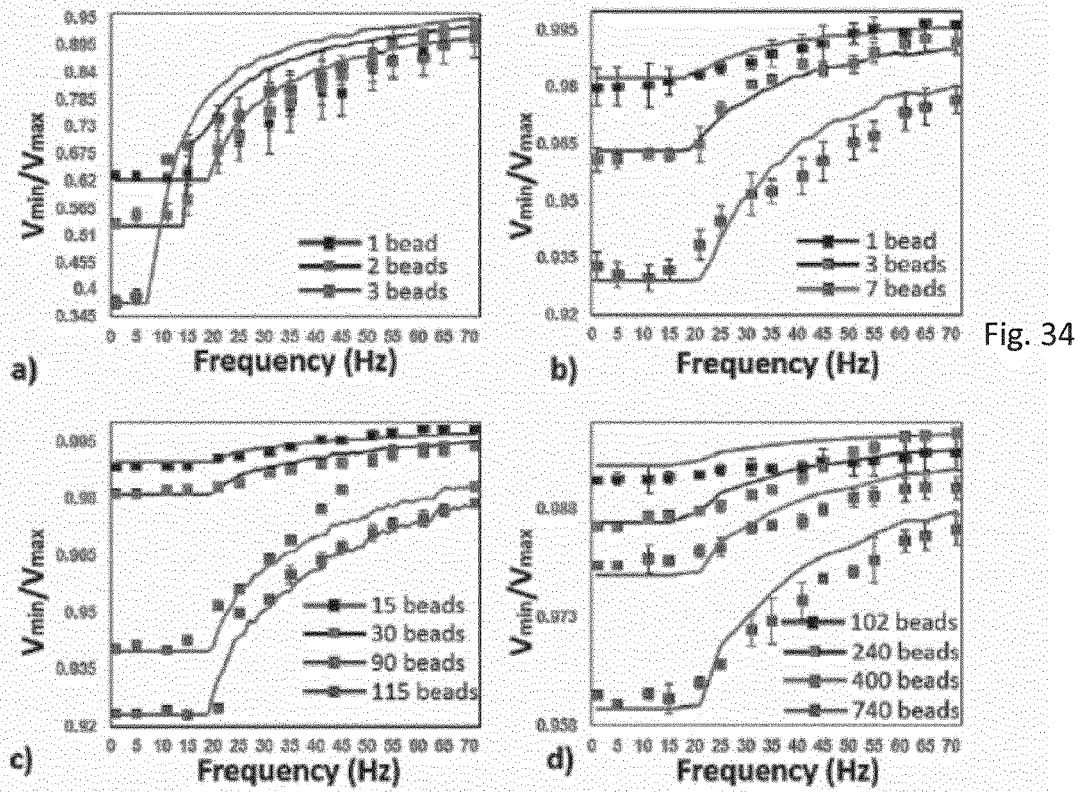
FIG. 34 Experimental and theoretical normalized signal for populations of beads for varying for: a) FOV1, b) FOV2, c) FOV3 and d) FOV4 for various population of beads. Colored lines represent theoretical results with chosen critical frequencies of 19 Hz, 13 Hz and 7 Hz for monomers, dimers and trimers respectively.

FIG. 34 $a$) represents the behavior of beads using FOV1. Due to the low-divergence of the Gaussian laser beam, the laser was tightly focused on a single micromagnet. Thus, a slight variation in the position of the beads could lead to a large variation in signal response. Also, different populations of beads (i.e. dimer, trimer, tetramer etc.) on a single magnet have different critical frequencies due to the increased hydrodynamic drag corresponding to their hydrodynamic radius. As the laser beam spreads for FOV2, FOV3 and FOV4 in FIGS. 34 $b$), $c$) and $d$) respectively, it enables simultaneous detection of the beads oscillating synchronously. Here, because the beads are trapped in their given potential energy minima around the magnet, Vmin/Vmax represents the normalized oscillation amplitude at any rotation frequency of external rotating magnetic field.

Figure 35:
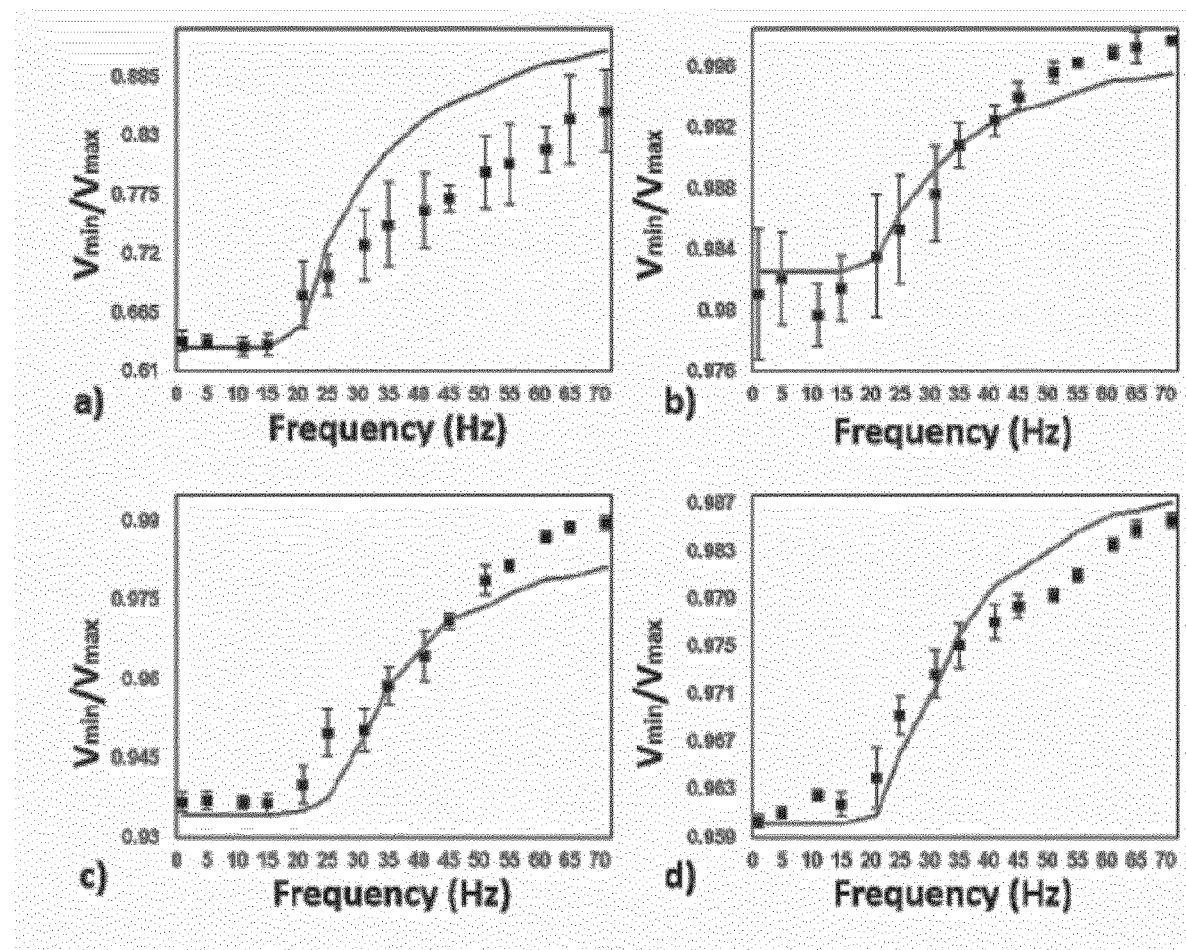
FIG. 35 Experimental determination of the normalized signal for populations of beads for as a function of the frequency of rotation of the external magnetic field. a) FOV1 for 1 bead, b) FOV2 for 1 bead, c) FOV3 for 100+/−5 beads and d) FOV4 for 750+/−20 beads. This required that beads were dispensed for each frequency in order to ensure approximately same population of beads within implemented field of view and to avoid previously reported aggregation at higher frequencies. Each data point is mean and standard deviation of three individual measurements. The red lines present the theoretical prediction.

Finally, the optical responses of different populations of beads on the MMA chip was measured at higher frequencies to determine if there was a maximum velocity for which the optical signal could be used to determine the number of beads. FIG. 35 presents the normalized signal amplitude at varying frequencies for particular populations of beads using four different optical configurations. It is clear that Vmin/Vmax stayed constant until the critical frequency was reached, after which it increased from a constant value towards unity. The critical frequency was easily defined as the frequency for which Vmin/Vmax diverges from its constant value and for all configurations it was found to be 19+/−2 Hz. The variation in critical frequency can be attributed to the coefficient of variation in external magnetic field uniformity, susceptibility and size of bead, and shape of the micromagnets. The maximum velocity of the beads for which the low frequency limit can use used was $\omega d/2\pi$. This determined the maximum velocity of the bead to be 152 microns/s.

A large standard deviation in Vmin/Vmax, observed in FIGS. 35 $a$) and $b$), can be attributed to a densely spread Gaussian beam in the illuminated area. Here, a minor variation in bead position generated a remarkable difference in signal responses. On the other hand, in FIGS. 35 $c$) and $d$), the Gaussian beam was homogeneous. The difference may primarily attributed to the asynchronous behavior of the beads.

Figure 36:
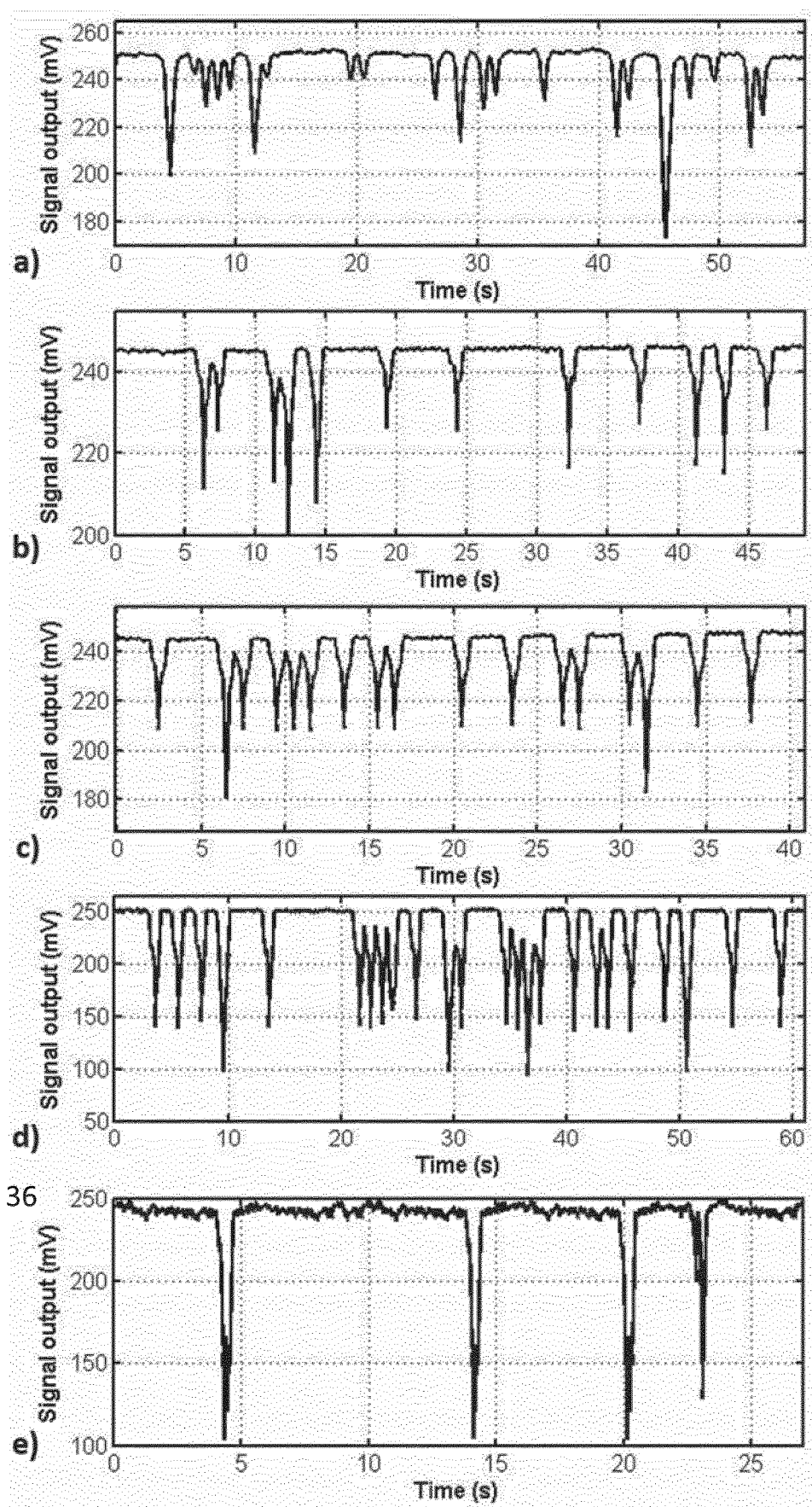
FIG. 36 shows Signal output of photodetector for di_erent size of the beads for FOV1 optical configuration. a) 0.55 microns, b) 0.87 microns, c) 1 micron, d) 2.8 microns and e) 5.6 microns FIG. 37 Comparison of signal with different substrate reflectance for 100 beads using FOV3 configuration.

As shown in the FIG. 36, Vmin/Vmax for different size of the beads are clearly distinguishable. Also, for a particular size of the beads, it is possible to discriminate monomers from their aggregates with high sensitivity.

Referring to FIGS. 39 to 41—The system may be applied for rapid and sensitive detection of analytes using magnetic bead aggregation (MBA) assay is presented in this section using novel opto-magnetophoretic system. The system as described works on a basic principle that periodically traveling aggregates of beads on a MMA chip scatter different amounts of light as compared to their non-aggregated state. The amplitude of the normalized photodetector signal corresponds to the concentration of analytes in the solution. In an exemplary application of use, the system was used to detect biotinylated bovine serum albumin (bBSA) and double stranded DNA from herpes simplex virus 1. In a total assay time of less than 30 minutes, a limit of detection lower than 300 fM and 10 pM have been demonstrated for detection of bBSA and dsDNA, respectively.

In an example, the system and method was used to demonstrate how the opto-magnetophoretic system automates and enhances the sensitivity and throughput of detection to a dramatic scale. The detection of bBSA was carried out. Here, the aggregation of beads was achieved via a strong biotin-streptavidin interaction known for being the strongest non-covalent bond (KD 10-15M) and high binding force (200 pN). Here, the FOV3 configuration was used for the simultaneous detection of multiple beads while retaining the sensitivity to a single bead level. Prior to dispensing the beads on the MMA chip, each solution was concentrated to a tenth of its original volume to increase the signal to noise ratio in detection. Also, the buffer was replaced from PBS to PBS+0.5% casein (Sigma-Aldrich, USA) to reduce the non-specific adhesion to the surface and concentrated to desire concentration to achieve high sensitivity. The signal was recorded for each analyte concentration and the normalized signal amplitude was averaged over 10 cycles for each frequency ranging from 1 Hz to 40 Hz. It was found in the example that the normalized amplitude (Vmin/Vmax) of variation per cycle (Vmin/Vmax) was directly proportional to the number of beads for a blank solution with no analytes. On the other hand, (Vmin/Vmax) did not give any information regarding the number of beads for solution containing analytes. However, there were differences in the values of (Vmin/Vmax) depending on the aggregation state of the sample. The higher the percentage of aggregates, the lesser the magnitude of the signal. Moreover, it should be noted that aggregations in the samples were achieved at the cost of their dispersity in the solution. This complicates theoretical prediction of experimental results. This observations were thoroughly investigated for detection of bBSA and dsDNA in the following sections.

FIG. 40 *a*) presents the normalized signal response for the reaction of bBSA concentrations varying from 3×10-15M to 3×10-9 with 0 M (blank) as external frequency increases from 0 to 35 Hz. Three features of the frequency response of the streptavidin-biotin MBA assay are worth further discussion. At low frequencies ($\omega \leq 7$ Hz), the normalized (Vmin/Vmax) increases as the bBSA concentrations increase. For each individual concentration, (Vmin/Vmax) remains constant until $\omega = 7$ Hz, which suggests that the setup can be used in the future to mimic the performance of the flow cytometer. At $\omega > 7$ Hz, the beads enter the phase-slipping regime, where the behavior is somewhat difficult to predict. It was observed that the non-specific interaction between beads resulted in an increased number of aggregates. It should also be noted that the non-linear signal response has different slopes depending on the state of aggregation in the solution. In other words, the value at which the signal is no longer distinguishable from the noise is different for different concentrations of analyte in solution. One of the advantages of opto-magnetophoretic system to detect bead aggregation is that once the beads are suspended on the MMA chip, the intramolecular bonds are not affected by the external magnetic force, making the system suitable for faster detection. The limit of detection of the dsDNA MBA assay was 3×10-13 M.

Referring to FIG. 41 the detection of dsDNA from herpes simplex virus was carried out in a sandwich-based MBA assay. FIG. 41 *a*) presents the normalized signal response for the reaction of varying hybridized dsDNA concentrations varying from 1×10-15 to 1×10-7M for varying external field frequencies from 0 to 35 Hz. Observations similar to those made during the detection of bBSA can be made. As the concentration of dsDNA in the solution increased, the percentage of aggregates as well as (Vmin/Vmax) increased as shown in FIG. 41 *b*). It has been mentioned in the literature that in an MBA assay the beads do not form just dimers but also trimers and higher-order aggregates. The size limit measured by the BD Accuri C6 flow cytometer is 16 m. This means that higher-order aggregates above 6 beads cannot be measured with the flow cytometer and are not recognizable. On the other hand, the opto-magnetophoretic device involves sheath-less actuation which does not affect the morphology of the aggregates. In the example testing it was observed that aggregates larger than 4 beads did not move in conventional manner, i.e. their displacement over time was slow. The reason for such their asynchronous and slow movement even at lower frequencies could be attributed to the increased drag force due to their large hydrodynamic radius. The limit of detection of the dsDNA MBA assay was 1×10-11M.

The optical detector of the example in accordance with the arrangements of the specification was been tested for detection of SPM bead aggregates in conjunction with an opto-magnetophoretic device. For both bBSA and dsDNA samples, opto-magnetophoretic device produces a similar time-varying periodic signal response, i.e. as the percentage of aggregates in the solution increases, the normalized signal amplitude increases as well. The limit of detection for bBSA and dsDNA MBA assays are 300 fM and 10 pM respectively. In the current experiments, the lower limit of detection is highly affected by non-specific adhesion on the surface as well as the reflectance difference between the micromagnets and the substrate. MMA chips based on transparent substrates could significantly increase the signal-to-noise ratio. Desirable features of this separation and detection system include bio-compatible, inexpensive, fast, sensitive, easy to use, multiplex detection, and real time sensing and separation. This system can advantageously be automated and miniaturized to produce a portable, sensitive, and inexpensive diagnosis instrument for point of care application.

Further examples of arrangements related to the pattered arrangement of for example FIG. 5 are provided.

For the example system and methods reference is made to FIGS. 34 to 49.

An MMA chip was fabricated. Before being functionalized with silanized-biotin, the chip was hydroxylated at 100 degrees C. for 30 min. The number of analytes that a substrate can accommodate depends on the total number of receptor available binding sites and the amount of area required per analyte. The minimum amount can be determined by mass transport and bead density limitations. If the number of receptor cites on the substrate are less than the number of analytes, it impacts the assay sensitivity.

The detection of SPM beads captured on the MMA chip was achieved using the same optical detection setup as in the opto-magnetophoretic system. Instead of using a steady illumination source, the laser was scanned across the MMA chip in a programmable manner. Prior to detection, force differentiation using the NLM setup was carried out to separate non-specifically interacting beads. External rotating magnetic field frequency of 1 Hz was chosen in order to avoid non-specific aggregation of beads with specifically captured beads on the surface. Scanning experiments were performed with individual motor speeds of 120 microns/s to scan micromagnets in raster manner, e.g., line by line. Focusing in the Z-axis was achieved manually at each step to ensure high signal to noise ratio. The overall time required for the detection is less than one minute to scan a total chip surface area of approximately 600 microns×400 microns in five steps.

In the absence of beads, the output voltage generates a maximum signal corresponding to the high reectivity of micromagnets, denoted as Vmax, and it can be calculated as follows:

$$V_{max} = R\, G\Omega I_{x,y}[S_{si}R_{si} + S_m R_m]$$

When the beads are captured on the micromagnets, the output voltage is given by:

$$V_{min} = RG\Omega I_{x,y}[S_{si}R_{si} + (S_m\zeta(t) - NS_P)R_m + NS_P R_P]$$

$$\frac{V_{min}}{V_{max}} = 1 - \frac{NS_P(R_S - R_P)}{S_{si}R_{si} + S_m R_m}$$

Which shows a linear relationship between (Vmin/Vmax) and the size and number of beads. It is clear from the equation that (Vmin/Vmax) is 1 in the absence of any bead and it decreases as the number of beads increases. It should be noted that V (t) is affected by the noise which is a limiting factor for the sensitivity and the resolution of the system. Moreover, the non-uniform shape of the micromagnets significantly increases the standard deviation of the signal. For 0.85 m, 1 m, 2.8 m and 5.6 m bead diameters, the normalized values (Vmin/Vmax) are 0.973+/−0.022, 0.913+/−0.081, 0.899+/−0.091, 0.601+/−0.179 and 0.468+/−0.293, respectively. For the following experiments in this chapter, beads with 2.8 microns in diameter are used.

An exemplary model streptavidin-biotin molecular recognition system has been tested for specificity using four types of beads, namely, streptavidin functionalized, carboxyl functionalized, anti-rat antibody functionalized and anti-rabbit antibody functionalized beads. As shown in FIG. 5 the SPM beads are dispensed and captured on the micromagnets.

Figure 49:
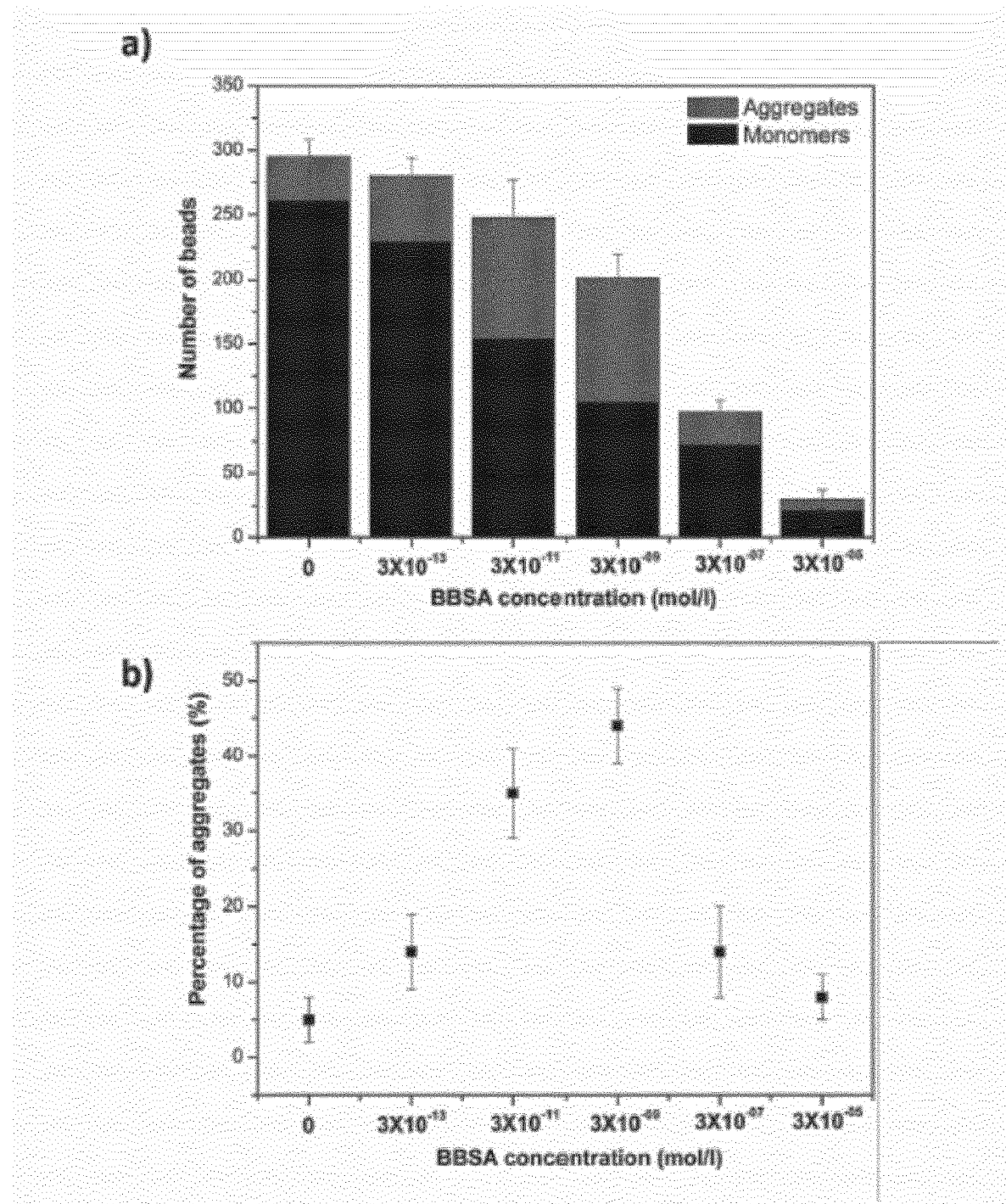
FIG. 49 Detection of the bBSA molecule using surface based assay: a) flow cytometry results b) optical scanner results. Mean and SD are for three samples.

In the exemplary arrangement and method once the beads are captured by the micromagnets, NLM transport at 1 Hz was used to separate the beads which did not interact. It should be noted that, each bead sample type was dispensed individually and the samples were not mixed for clear distinction between specific and non-specific interaction. The number of beads was counted using microscope for several fields of view (the largest field of view used in this study is 0.4 mm2 in size) after all the travelling beads were moved out of the observation area. For the first set of experiments, 2.5×10-3 M of Silanized biotin was covalently grafted on several MMA chips to test the specificity of the assay. At this concentration and considering an incubation time of 2 h and a mass transfer coefficient of 0.001 m/s, the number of molecules that can come in contact with the surface can be estimated to be $10^7$ molecules/nm$^2$ which is sufficient to saturate the surface. As Silanized-biotin molecules do not interact with each other, non-adhered molecules are washed away when cleaned with water. The recorded signal responses using optical scanner for four types of beads are shown in FIG. 45. Due to steric hindrance or the presence of beads already captured at certain site on the surface, the beads might be captured away from the center of the micromagnet. In that case, Vmax would be different depending on the presence of the bead either on the cobalt micromagnet, on the silicon substrate or somewhere in-between. The position of the bead can be predicted precisely by spotting the position of (Vmin) due to the periodically varying signal. Comparing the FIG. 46 *a*) with FIGS. 46 *b*), *c*) and *d*), it is clear that the number of captured streptavidin beads are very high as compared to the other bead types due to strong hydrophobic interaction between biotin and streptavidin molecules. FIGS. 46 *b*), *c*) and *d*) emphasize non-specific interaction on Silanized-biotin functionalized surface. FIG. 49 *a*) presents the results showing number of beads with different functional groups captured on si-biotin functionalized and non-functionalized MMA surfaces.

Figure 48:
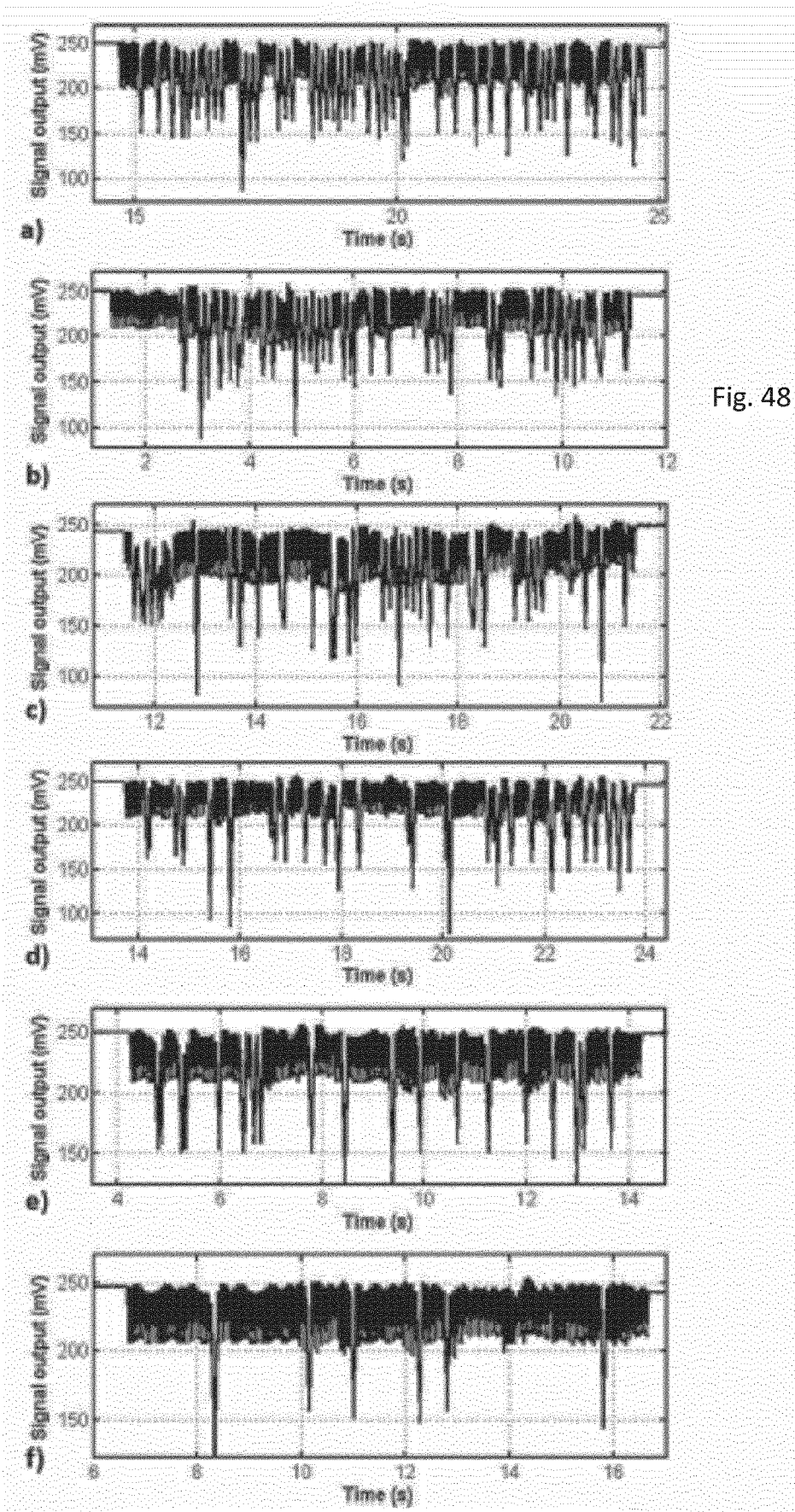
FIG. 48 Detection of bBSA using optical scanner: a) blank, b) $3 \times 10^{-13}$ M, c) $3 \times 10^{-11}$ M, d) $3 \times 10^{-09}$ M, e) $3 \times 10^{-07}$ M, f) $3 \times 10^{-05}$ M, Scanning is performed at 120 microns/s.

By keeping the same concentration for each bead type, the optical scanner measurement ensured that the number of beads captured on each surface corresponds to either specific biotin-streptavidin interaction or non-specific adhesion to the surface. In FIG. 48 *a*), the population of streptavidin beads on a functionalized surface is distinguishable as compared to the number of beads of other bead types on both types of surfaces. For the second experiment, different concentrations of Silanized-biotin, ranging from 2.5×10-03 M to 2.5×10-13 M, were covalently grafted on MMA chip as explained in the detection scheme in the experimental section. FIG. 48 *b*) represents the results showing a way to improve sensitivity using the biotin-streptavidin model by detecting and counting the captured streptavidin beads on different biotin functionalized surface with different concentrations. The number of captured beads was observed to increase as the concentration of Silanized-biotin increased from 2.5×10-13 M to 2.5×10-05 M. It should be noted that for higher concentrations such as 2.5×10-07 M and 2.5×10-05 M, the number of available sites of biotin to capture the streptavidin beads saturate and thus serve as the upper limit of detection. The lower limit of detection is defined as three times the standard deviation of the blank. Thus, the limit of detection for these measurements is approximately 100 fM. Furthermore, the detection of bBSA was carried out using a double sandwich assay. In other words, the detection of bBSA takes place in three steps in this exemplary arrangement and application of the system. First two steps are same as described in the protocol of the MBA assay. Once the samples are prepared with different concentrations of bBSA, 10 micro litres of each sample solution is dispensed on the functionalized surface with Silanized-biotin. FIG. 48 presents the optical scanner signal for different concentrations of the captured streptavidin beads on the MMA chips. It is clear that as the concentration of bBSA increases, the number of beads interacting with the biotinylated surface decreases. For example, FIG. 48 *a*) shows that in the absence of any bBSA molecule, all the streptavidin sites are available to interact with the biotinylated substrate. In the presence of bBSA, the number of streptavidin binding sites decreases corresponding to the concentration of bBSA.

Further, bBSA-functionalized beads do not interact with the biotinylated surface and are separated using NLM. This can be noticed as a decrease in the number of spikes in FIG. 48 *b*)-*f*). It has been reported that the time scale for bead sample preparation affects the formation of bead aggregates. From the flow cytometry analysis for the prepared bBSA samples (see FIG. 49 *a*)) Here, the sensitivity of the assay is determined by the affinity of the molecular recognition system used. As the number of available sites on the streptavidin beads decreases with the increase in bBSA concentration, the number of beads interacting on the surface reduces due to active steric repulsion between a biotin molecule adhered on bead and a biotin molecule tethered on MMA chip. This can be clearly observed for 3×10-07 M and 3×10-05 M of concentrations. Moreover, to obtain dose-response curve for bBSA, the mean and standard deviations of the number of beads captured on the Silanized-biotin coated surface were compared as shown in FIG. 49. As the concentration of bBSA in the solution increased, the total number of beads that are captured on the substrate decreased. The reason for the decrease in the total number of beads can be attributed to the number of available streptavidin binding sites as well as to a decrease in the dispersity of the beads in the dispensing solution. The limit of detection for this assay is 300 fM. For solutions with high concentration of bBSA, blocking is observed to be decreasing as bBSA start to saturate bead surface. Thus, the available binding sites decrease with an increase in bBSA concentration.

These measurements clearly show that the effect of different concentrations of bBSA can be quantitatively measured using the proposed technique. This paves the way for further studying of biologically specific ligand-receptor systems to determine the concentration of analytes present in the sample above the Hook effect.

According to the arrangement of the specification, advantageously, a setup for magnetic immunoassays has been developed that is able to automatically quantify the number of beads attached to a surface. The feasibility of this technique was shown by studying the specific interaction between streptavidin functionalized beads and the Silanized-biotin functionalized surface. The presented results constitute several key achievements. Our optical scanner has been used as an integrated and automated readout device, capable of providing low-noise and reproducible measurements of the dynamics of SPM beads captured on the micromagnets. Even though the maximum detection rate is limited by alignment/focusing issues in the current bulky set-up, it can be tuned by using a combination of objective lenses with different numerical aperture or increased sizes of the micro-magnets (up to ten fold). In addition, a more sophisticated data treatment approach, based on improved evaluation algorithms, may further reduce the limit of detection and increase the dynamic range of the readout for the enumeration of rare-cells or surface based assays. The magnetic bead capturing assay has been demonstrated to show the potential of the proposed setup as a diagnostic tool by detecting tethered biotin molecules with streptavidin-functionalized SPM beads. The same principle can be used to capture antigens in cells and tissues and to detect and separate biomolecules from complex mixtures. The setup is generic and can be used to detect numerous biomarkers by functionalizing beads and the solid surface with appropriate receptors.

Further advantages include simplicity, potential for miniaturization, sensitivity and detection rates, the optical scanner setup could be used to develop a relatively inexpensive and portable biosensor.

The invention claimed is:

1. An integrated bio-separation and optical detection system for detection of analytes in a sample based on non-linear magnetophoretic separation, the sample being prepared with functionalized superparamagnetic (SPM) particles provided for binding with selected target analytes, the system comprising:
a separation chip comprising at least one micro-magnet array comprising a plurality of spaced apart micro-magnets, the at least one micro-magnet array being disposed on a substrate and comprising a capture region, a focusing region, and a detection region;
the capture region comprising a plurality of micro-magnets in a rectilinear arrangement;
the focusing region comprising a converging micro-magnet array comprising (i) micro-magnets arranged in lines at an angle of 5 to 30 degrees to a major axis and the lines of micro-magnets of the focusing region being substantially parallel while converging to the detection region, or, (ii) micro-magnets arranged in lines in a tree-like structure converging in consecutive steps to the detection region; and
the detection region comprising a single row of reflective micro-magnets including a reflective metal defining micro-sized mirrors on the substrate with the substrate having a lower reflectivity compared to the reflectivity of the micro-magnets of the detection region, wherein the micro-magnets comprise one or more of (i) Chromium, and (ii) Cobalt with a layer of Chromium on the Cobalt;
a non-linear magnetic (NLM) separator, the NLM separator having external magnets controllable and configured to apply a rotating magnetic field to a surface of the chip to effect separation of the sample provided thereto by non-linear magnetophoresis, wherein the superparamagnetic particles and aggregates thereof are translated over surfaces of the chip, including surfaces of the substrate and the reflective micro-magnets, under an influence of the rotating magnetic field and the field of the fixed micro-magnets of the at least one micro-magnet array,
wherein a rotation frequency of the rotating magnetic field applied by the external magnets of the NLM separator is varied during the course of the separation to effect movement, capture, and separation of the SPM particles on the substrate; and
characterized in that the system further comprises
an integrated optical detector comprising a light source and a detector having a field of view, the light source configured to illuminate a surface of the substrate, and the detector configured to detect light reflected from the substrate at the field of view and configured to generate output signals including an initial light output signal of light reflected from the substrate before the sample is introduced, and to generate separation light output signals of light reflected from the surface of the substrate during the course of the separation, as modulated by SPM particles, aggregates, clusters and target analytes of the sample being translated over the surface of the substrate, such that separation light output signals are representative of the particles, aggregates, clusters and target analytes that are transported through the field of view during the course of the separation, and
a data acquisition and processing computer configured to receive as input (i) parameters of the separation including dimensions, number, and optical properties of the SPM particles, and dimensions and optical properties of the aggregates, clusters and target analytes; (ii) the initial light output signal from the detector indicative of properties of the substrate surface, and (iii) the separation light output signals from the detector, the inputs being analyzed by the data acquisition and processing computer to detect a difference between the initial light output signal and the separation light output signals to obtain information about the SPM particles, aggregates, clusters and target analytes of the sample, and to identify presence, number, and concentration of SPM particles, aggregates, clusters and target analytes of the sample.

2. The system of claim 1 wherein the data acquisition and processing computer receives as input the frequency of rotation of the applied magnetic field during the course of the separation.

3. The system of claim 1 wherein the data acquisition and processing computer receives as input details of the at least one micro-magnet array.

4. The system of claim 1 wherein the data acquisition and processing computer receives as an input, an initial output signal of the optical detector based on light interaction with the substrate prior to the sample being introduced to the substrate, and, separation output signals based on light interaction with the substrate during a runtime of the separation.

5. The system of claim 1 wherein the data acquisition and processing computer is configured to analyze a frequency and intensity spectrum of the output signal of the optical detector to differentiate target biological materials attached to the SPM particles in suspension in the sample.

6. The system of claim 1 wherein the light source comprises a monochromatic laser configured to illuminate the at least one micro-magnet array.

7. The system of claim 1 wherein a frequency response of the output signal of the optical detector changes as dimensions of the SPM particles change and optical properties of particles change.

8. The system of claim 1 wherein a frequency response of output signal of the optical detector can also be changed due to different immobility of samples with different proportion of aggregates.

9. The system of claim 1 wherein an intensity of light detected by the optical detector is dependent on micro-magnet array surface properties, fluid, and number of microparticles P, dimension of particles, and optical properties of the particles.

10. The system of claim 1, wherein light detected from the micro-magnet array is periodically modulated during the separation by motion of the SPM particles on the at least one micro-magnet array such that output signal of the detector is modulated by motion of the SPM particles on the at least one micro-magnet array by controlling the rotation frequency of rotating magnetic field.

11. The system of claim 1, wherein the inputs include magnetic properties of the SPM particles and hydrodynamic drag factors and rotation frequency.

12. The system of claim 1 wherein the data acquisition and processing computer is configured to analyze SPM particle differences in dimensions, optical properties, and non-linear magnetophoresis (NLM) transport, wherein mixture of different SPM particles can be detected by opto-non-linear magnetophoresis (ONLM) because frequency response of ONLM is different between different SPM particles.

13. The system of claim 1 wherein the optical detector comprises an optical detector located above the at least one micro-magnet array to detect light reflected from the substrate or from the at least one micro-magnet array.

14. The system of claim 1 wherein the optical detector comprises a photodetector located below the at least one micro-magnet array to detect light transmitted through the substrate or through the at least one micro-magnet array.

15. The system of claim 1 wherein the micro-magnets of the detection region comprise a transparent cover layer comprising a Silicon dioxide or polymer material.

16. The system of claim 1 wherein the at least one micro-magnet array comprises micro-magnets separated by gaps.

17. The system of claim 1, configured such that when SPM particles move during separation to gaps between adjacent micro-magnets, an intensity of light reflected from the at least one micro-magnet array to the detector is at a maximum.

18. The system of claim 1 configured such that when SPM particles move directly over or onto a top of micro-magnets as a phase of rotating magnetic field is changed, an intensity of reflective or reflected light is decreased to minimum.

19. The system of claim 1 wherein during separation the SPM particles are moved on the at least one micro-magnet array in controlled manner by controlled application of different rotation frequencies of the rotating magnetic field during a runtime of the separation.

20. The system of claim 1 having a light source adjustable to achieve a laser spot diameter of between approximately 94 μm and 6 μm on the substrate.

* * * * *